US011066679B2

(12) United States Patent
Kotin et al.

(10) Patent No.: US 11,066,679 B2
(45) Date of Patent: Jul. 20, 2021

(54) CLOSED-ENDED LINEAR DUPLEX DNA FOR NON-VIRAL GENE TRANSFER

(71) Applicants: University of Massachusetts, Boston, MA (US); Voyager Therapeutics, Inc., Cambridge, MA (US)

(72) Inventors: Robert M. Kotin, Bethesda, MD (US); Sylvain Cecchini, Westborough, MA (US)

(73) Assignees: University of Massachusetts, Boston, MA (US); Voyager Therapeutics, Cambridge, MA (US)

(*) Notice: Subject to any disclaimer, the term of this patent is extended or adjusted under 35 U.S.C. 154(b) by 189 days.

(21) Appl. No.: 16/081,337

(22) PCT Filed: Mar. 3, 2017

(86) PCT No.: PCT/US2017/020828
§ 371 (c)(1),
(2) Date: Aug. 30, 2018

(87) PCT Pub. No.: WO2017/152149
PCT Pub. Date: Sep. 8, 2017

(65) Prior Publication Data
US 2019/0032083 A1  Jan. 31, 2019

Related U.S. Application Data

(60) Provisional application No. 62/406,913, filed on Oct. 11, 2016, provisional application No. 62/394,720, filed on Sep. 14, 2016, provisional application No. 62/303,047, filed on Mar. 3, 2016.

(51) Int. Cl.
| | | |
|---|---|---|
| C12N 15/86 | (2006.01) | |
| C12N 15/09 | (2006.01) | |
| C12N 15/63 | (2006.01) | |
| C12N 15/66 | (2006.01) | |
| C07K 14/005 | (2006.01) | |
| C12N 15/64 | (2006.01) | |
| A61P 11/12 | (2006.01) | |
| A61P 27/02 | (2006.01) | |
| A61P 3/08 | (2006.01) | |
| A61P 7/04 | (2006.01) | |
| A61P 1/16 | (2006.01) | |
| A61P 3/00 | (2006.01) | |
| A61K 48/00 | (2006.01) | |

(52) U.S. Cl.
CPC ............ *C12N 15/86* (2013.01); *A61K 48/005* (2013.01); *A61K 48/0075* (2013.01); *A61P 1/16* (2018.01); *A61P 3/00* (2018.01); *A61P 3/08* (2018.01); *A61P 7/04* (2018.01); *A61P 11/12* (2018.01); *A61P 27/02* (2018.01); *C07K 14/005* (2013.01); *C12N 15/09* (2013.01); *C12N 15/63* (2013.01); *C12N 15/64* (2013.01); *C12N 15/66* (2013.01); *A61K 48/00* (2013.01); *C12N 2710/14043* (2013.01); *C12N 2750/14122* (2013.01); *C12N 2750/14143* (2013.01); *C12N 2750/14151* (2013.01)

(58) Field of Classification Search
CPC ........ C12N 15/09; C12N 15/63; C12N 15/64; C12N 15/66; C12N 15/86; C12N 2310/531; C12N 2750/14143
USPC ........... 435/6.1, 6.11, 91.1, 91.31, 455, 458; 536/23.1, 24.5
See application file for complete search history.

(56) References Cited

U.S. PATENT DOCUMENTS

| | | | |
|---|---|---|---|
| 4,683,195 A | 7/1987 | Mullis et al. | |
| 5,316,908 A | 5/1994 | Carlson et al. | |
| 5,658,548 A | 8/1997 | Padhye et al. | |
| 8,241,622 B2 | 8/2012 | Englehardt et al. | |

FOREIGN PATENT DOCUMENTS

| | | | |
|---|---|---|---|
| JP | 2004-508041 A | 3/2004 | |
| WO | WO 2012/123430 A1 | 9/2012 | |
| WO | WO-2012123430 A1 * | 9/2012 | ............... A61P 25/16 |

OTHER PUBLICATIONS

Hickman etal, Molecular Cell, vol. 13, pp. 403-414. (Year: 2004).*
Chiorini, JA, J. Virology, vol. 68, No. 11, pp. 7448-7457. (Year: 1994).*
Extended European Search Report for Application No. EP 17760963.3, dated Aug. 14, 2019.
Bohenzky et al., Sequence and symmetry requirements within the internal palindromic sequences of the adeno-associated virus terminal repeat. Virology. 1988;166(2):316-327. doi:10.1016/0042-6822(88)90502-8.
Gonçalves, Adeno-associated virus: from defective virus to effective vector. Virol J. 2005;2:43. Published May 6, 2005. doi:10.1186/1743-422X-2-43.
Li et al., Production and characterization of novel recombinant adeno-associated virus replicative-form genomes: a eukaryotic source of DNA for gene transfer. PLoS One. 2013;8(8):e69879. Published Aug. 1, 2013. doi:10.1371/journal.pone.0069879.
Mccarty, Self-complementary AAV vectors; advances and applications. Mol Ther. 2008;16(10):1648-1656. doi:10.1038/mt.2008171.
Samulski et al., Rescue of adeno-associated virus from recombinant plasmids: gene correction within the terminal repeats of AAV. Cell. 1983;33(1):135-143. doi:10.1016/0092-8674(83)90342-2.

(Continued)

*Primary Examiner* — Jane J Zara
(74) *Attorney, Agent, or Firm* — Wolf, Greenfield & Sacks, P.C.

(57) ABSTRACT

Aspects of the disclosure relate to a nucleic acid comprising a heterologous nucleic acid insert flanked by interrupted self-complementary sequences, wherein one self-complementary sequence is interrupted by a cross-arm sequence forming two opposing, lengthwise-symmetric stem-loops, and wherein the other of the self-complementary sequences is interrupted by a truncated cross-arm sequence. Methods of delivering the nucleic acid to a cell are also provided.

16 Claims, 21 Drawing Sheets

Specification includes a Sequence Listing.

(56) References Cited

OTHER PUBLICATIONS

Cataldi et al., Hairpin-end conformation of adeno-associated virus genome determines interactions with DNA-repair pathways. Gene Ther. Jun. 2013;20(6):686-93. doi: 10.1038/gt.2012.86. Epub Nov. 15, 2012.
Cheng et al., Molecular weight determination of plasmid DNA using electrospray ionization mass spectrometry. Nucleic Acids Res. Jun. 1, 1996;24(11):2183-9.
Chiorini et al., Sequence requirements for stable binding and function of Rep68 on the adeno-associated virus type 2 inverted terminal repeats. J Virol. Nov. 1994;68(11):7448-57.
Glauser et al., Four-dimensional visualization of the simultaneous activity of alternative adeno-associated virus replication origins. J Virol. Oct. 2005;79(19):12218-30.
Hickman et al., The nuclease domain of adeno-associated virus rep coordinates replication initiation using two distinct DNA recognition interfaces. Mol Cell. Feb. 13, 2004;13(3):403-14.
Virag et al., Producing recombinant adeno-associated virus in foster cells: overcoming production limitations using a baculovirus-insect cell expression strategy. Hum Gene Ther. Aug. 2009;20(8):807-17. doi:10.1089/hum.2009.092.
Yan et al., Inverted terminal repeat sequences are important for intermolecular recombination and circularization of adeno-associated virus genomes. J Virol. Jan. 2005;79(1):364-79.

\* cited by examiner

FIG. 1A

Symmetric ITRS         Asymmetric Terminal Palindromes (ATP)

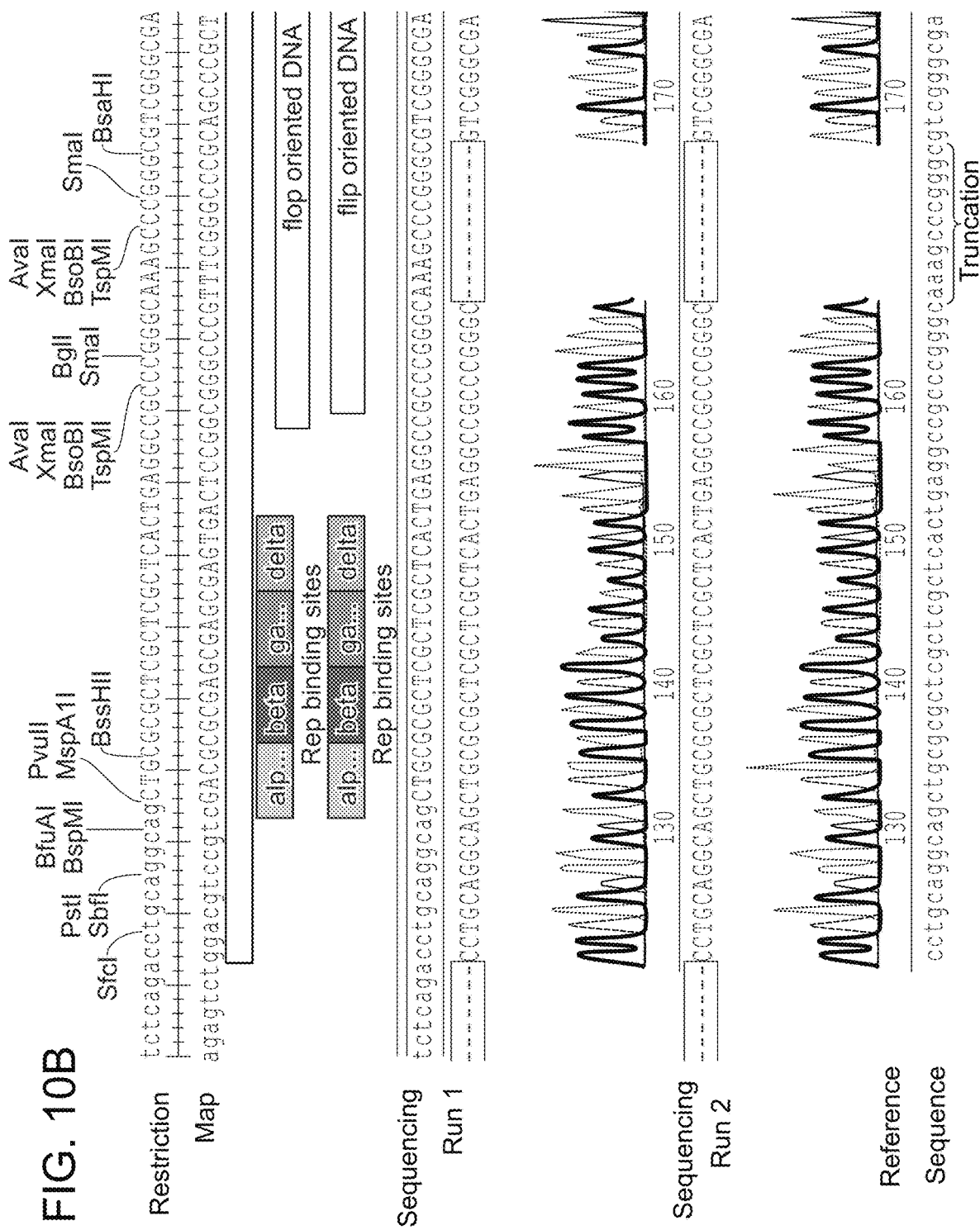

FIG. 10B (continued)

SEQUENCE LISTING

<160> NUMBER OF SEQ ID NOS: 14

<210> SEQ ID NO 1
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 1
gctcgctcgc tc                                                          12

<210> SEQ ID NO 2
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 2
cgggcgacca aaggtcgccc gacgcccggg ctttgcccgg gc                         42

```
<210> SEQ ID NO 3
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 3
gcccgggcaa agcccgggcg tcgggcgacc tttggtcgcc cg                            42

<210> SEQ ID NO 4
<211> LENGTH: 145
<212> TYPE: DNA
<213> ORGANISM: Artificial Sequence
<220> FEATURE:
<223> OTHER INFORMATION: Synthetic Polynucleotide

<400> SEQUENCE: 4
ttggccactc cctctctgcg cgctcgctcg ctcactgagg ccgggcgacc aaaggtcgcc         60
cgacgcccgg gctttgcccg ggcggcctca gtgagcgagc gagcgcgcag agagggagtg        120
gccaactcca tcactagggg ttcct                                              145

<210> SEQ ID NO 5
<211> LENGTH: 145
<212> TYPE: DNA
<213> ORGANISM: Artificial Sequence
<220> FEATURE:
<223> OTHER INFORMATION: Synthetic Polynucleotide

<400> SEQUENCE: 5
aaccggtgag ggagagacgc gcgagcgagc gagtgactcc ggcccgctgg tttccagcgg         60
gctgcgggcc cgaaacgggc cgccggagt cactcgctcg ctcgcgcgtc tctccctcac        120
cggttgaggt agtgatcccc aagga                                              145

<210> SEQ ID NO 6
<211> LENGTH: 145
<212> TYPE: DNA
<213> ORGANISM: Artificial Sequence
<220> FEATURE:
<223> OTHER INFORMATION: Synthetic Polynucleotide

<400> SEQUENCE: 6
aggaacccct agtgatggag ttggccactc cctctctgcg cgctcgctcg ctcactgagg         60
ccgggcgacc aaaggtcgcc cgacgcccgg gctttgcccg ggcggcctca gtgagcgagc        120
gagcgcgcag agagggagtg gccaa                                              145

<210> SEQ ID NO 7
<211> LENGTH: 145
<212> TYPE: DNA
<213> ORGANISM: Artificial Sequence
<220> FEATURE:
<223> OTHER INFORMATION: Synthetic Polynucleotide

<400> SEQUENCE: 7
tccttgggga tcactacctc aaccggtgag ggagagacgc gcgagcgagc gagtgactcc         60
ggcccgctgg tttccagcgg gctgcgggcc cgaaacgggc cgccggagt cactcgctcg        120 ctcgcgcgtc tctccctcac cggtt                                              145
```

```
<210> SEQ ID NO 8
<211> LENGTH: 144
<212> TYPE: DNA
<213> ORGANISM: Artificial Sequence
<220> FEATURE:
<223> OTHER INFORMATION: Synthetic Polynucleotide

<400> SEQUENCE: 8
aggaaccctA gtgatggagt tggccactcc ctctctgcgc gctcgctcgc tcactgaggc      60
cgcccgggca aagcccgggc gtcgggcgac ctttggtcgc ccggcctcag tgagcgagcg     120
agcgcgcaga gagggagtgg ccaa                                            144

<210> SEQ ID NO 9
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 9
cccgtgcggg cccaaagggc ccgc                                             24

<210> SEQ ID NO 10
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 10
gcccgctggt ttccagcggg ctgcgggccc gaaacgggcc cgc                        43

<210> SEQ ID NO 11
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 11
cgggcccgtg cgggcccaaa gggcccgc                                         28

<210> SEQ ID NO 12
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 12
gcccgggcac gcccgggttt cccgggcg                                         28

<210> SEQ ID NO 13
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 13
cgtgcgggcc caaagggccc gc                                               22
```

```
<210> SEQ ID NO 14
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 14
gcgggccgga aacgggcccg ctgcccgctg gtttccagcg ggc                              43
```

CLOSED-ENDED LINEAR DUPLEX DNA FOR NON-VIRAL GENE TRANSFER

RELATED APPLICATIONS

This application is a National Stage Application of PCT/US2017/020828, filed Mar. 3, 2017, entitled "CLOSED-ENDED LINEAR DUPLEX DNA FOR NON-VIRAL GENE TRANSFER", which claims the benefit under 35 U.S.C. 119(e) U.S. Provisional Application 62/303,047, filed on Mar. 3, 2016, entitled "CLOSED-ENDED LINEAR DUPLEX DNA FOR NON-VIRAL GENE TRANSFER", U.S. Provisional Application 62/394,720, filed Sep. 14, 2016, entitled "CLOSED-ENDED LINEAR DUPLEX DNA FOR NON-VIRAL GENE TRANSFER", and U.S. Provisional Application 62/406,913, filed Oct. 11, 2016, entitled "CLOSED-ENDED LINEAR DUPLEX DNA FOR NON-VIRAL GENE TRANSFER", the entire contents of each application which are incorporated herein by reference.

BACKGROUND

Current gene delivery vectors have several drawbacks. Both viral and bacterial-derived gene delivery vectors can induce the innate and adaptive immune responses of a patient. For example, plasmid DNA (pDNA) and mini-circle DNA (mcDNA) vectors, typically have prokaryotic patterns of DNA methylation that are not present in eukaryotic DNA. Additionally, lipopolysaccharides (LPS) and other bacterial-derived molecules are recognized in vertebrate cells by the innate immune response pattern recognition receptor (PRR) as pathogen-associated molecular patterns (PAMPs), leading to activation of cellular genes in response to the invasive microbial pathogen. Plasmid DNA conformationally is uniquely bacterial; the closest mammalian structure is the mitochondrial genome, or duplex circular DNA, which compartmentalized in the organelle, is not exposed to the cytosolic PRRs. In another example, recombinant adeno-associated viruses (rAAVs) can induce a T-cell response to processed capsid antigens or be neutralized by circulating immunoglobulins and non-Ig glycoproteins. Viral vectors also have limited transgene carrying capacity and are labor intensive, expensive, and time consuming to produce. Accordingly, improved compositions and methods for gene delivery are needed.

SUMMARY

The disclosure relates, in some aspects, to the discovery that replication of nucleic acids encoding a heterologous nucleic acid insert flanked by certain types of asymmetric termini (e.g., asymmetric interrupted self-complementary sequences) results in covalent linkage of the asymmetric termini (e.g., asymmetric interrupted self-complementary sequences) and leads to the production of a novel conformation of closed-ended linear duplex DNA (ceDNA). In some embodiments, nucleic acids having asymmetric interrupted self-complementary sequences can be readily produced (e.g., in large quantities) while avoiding scale up issues associated with other gene therapy vectors (e.g., viral based vectors). This result is surprising in view of reports that symmetry is required in the internal palindromic region for purposes of propagation of similar nucleic acids.

In some embodiments, nucleic acids having asymmetric interrupted self-complementary sequences, as disclosed herein, may have improved genetic stability compared with other gene therapy vectors (e.g., nucleic acids having symmetric interrupted self-complementary sequences). In some embodiments, nucleic acids having asymmetric interrupted self-complementary sequences, as disclosed herein, may have improved safety profiles compared with other vectors (e.g., nucleic acids having symmetric interrupted self-complementary sequences). For example, in some embodiments, administration of nucleic acids having asymmetric interrupted self-complementary sequences may be less likely to result in insertional mutagenesis compared with other vectors (e.g., nucleic acids having symmetric interrupted self-complementary sequences) due to the asymmetric nature of the construct.

In certain embodiments, nucleic acids having asymmetric interrupted self-complementary sequences that are engineered to express a transcript (e.g., a transcript encoding a protein or functional nucleic acid) may have improved expression compared with other vectors (e.g., nucleic acids having symmetric interrupted self-complementary sequences) because the asymmetric nature of the constructs makes them less likely to interact in cells with certain enzymes (e.g., helicases, such as, RecQ helicases) that can reduce the transcriptional capacity of such vectors.

In some embodiments, administration of a nucleic acid having asymmetric interrupted self-complementary sequences, as described herein, is less likely to induce an immune response in a subject compared with administration of other gene therapy vectors (e.g., plasmid DNA vectors and viral vectors). Therefore, in some embodiments, a nucleic acid described herein can be administered to a subject on multiple occasions (e.g., in the context of long-term gene therapy) without inducing a substantial immune response that would prevent or inhibit expression and/or activity of a gene product encoded by the nucleic acid.

In some aspects, the disclosure provides a nucleic acid comprising a heterologous nucleic acid insert flanked by at least one interrupted self-complementary sequence, each self-complementary sequence having an operative terminal resolution site and a rolling circle replication protein binding element, wherein the self-complementary sequence is interrupted by a cross-arm sequence forming two opposing, lengthwise-symmetric stem-loops, each of the opposing lengthwise-symmetric stem-loops having a stem portion in the range of 5 to 15 base pairs in length and a loop portion having 2 to 5 unpaired deoxyribonucleotides.

In some embodiments, interrupted self-complementary sequences are derived from a one or more organisms or viral serotypes, including from parvoviruses, dependovirus, etc. For example, in some embodiments, a nucleic acid comprises a first interrupted self-complementary sequence derived from an AAV2 serotype and a second interrupted self-complementary sequence derived from an AAV9 serotype. In another non-limiting example, a nucleic acid as described by the disclosure may comprise a first interrupted self-complementary sequence from an AAV2 serotype and a second interrupted self-complementary sequence from a parvovirus (e.g., parvovirus B19). In some embodiments, interrupted self-complementary sequences are derived from the same organism or viral serotype but have different lengths, or combinations of the foregoing. In some embodiments, the nucleic acid comprises a second interrupted self-complementary sequence that is interrupted by a truncated cross-arm sequence. For example, in some embodiments, a nucleic acid comprises a first self-interrupted self-complementary sequence derived from an AAV2 serotype that is 145 base pairs in length, and a second interrupted self-complementary sequence derived from an AAV2 serotype that is shorter than 145 base pairs in length (e.g., a truncated cross-arm sequence).

In some aspects, the disclosure provides a nucleic acid comprising a heterologous nucleic acid insert flanked by interrupted self-complementary sequences, each self-complementary sequence having an operative terminal resolution site and a rolling circle replication protein binding element, wherein one self-complementary sequence is interrupted by a cross-arm sequence forming two opposing, lengthwise-symmetric stem-loops, each of the opposing lengthwise-symmetric stem-loops having a stem portion in the range of 5 to 15 base pairs in length and a loop portion having 2 to 5 unpaired deoxyribonucleotides, wherein the other of the self-complementary sequences is interrupted by a truncated cross-arm sequence.

In some embodiments, the interrupted self-complementary sequence(s) are in the range of 40 to 1000 nucleotides in length. In some embodiments, the interrupted self-complementary sequence(s) are in the range of 100 to 160 nucleotides in length.

In some embodiments, the cross-arm sequence has a Gibbs free energy (ΔG) of unfolding under physiological conditions in the range of −12 kcal/mol to −30 kcal/mol. In some embodiments, the cross-arm sequence has a Gibbs free energy (ΔG) of unfolding under physiological conditions in the range of −20 kcal/mol to −25 kcal/mol.

In some embodiments, each of the opposing lengthwise-symmetric stem-loops have a stem portion in the range of 3 to 15 base pairs in length. In some embodiments, each of the opposing lengthwise-symmetric stem-loops have a stem portion in the range of 8 to 10 base pairs in length.

In some embodiments, each loop portion has 2 to 5 unpaired deoxyribonucleotides. In some embodiments, each loop portion has three deoxyribonucleotides.

In some embodiments, one loop portion has three deoxythymidines and the other loop portion has three deoxyadenosines.

In some embodiments, the rolling circle replication protein binding element is a Rep binding element (RBE). In some embodiments, the RBE comprises the sequence 5'-GCTCGCTCGCTC-3' (SEQ ID NO: 1).

In some embodiments, the operative terminal resolution site comprises a sequence 5'-TT-3'. In some embodiments, the 3' end of the operative terminal resolution site is 15 to 25 nucleotides from the 5' end of the rolling circle replication protein binding element.

In some embodiments, the truncated cross-arm sequence forms two opposing, lengthwise-asymmetric stem-loops. In some embodiments, one of the opposing, lengthwise-asymmetric stem-loops has a stem portion in the range of 8 to 10 base pairs in length and a loop portion having 2 to 5 unpaired deoxyribonucleotides. In some embodiments, the one lengthwise-asymmetric stem-loop has a stem portion less than 8 base pairs in length and a loop portion having 2 to 5 deoxyribonucleotides. In some embodiments, the one lengthwise-asymmetric stem-loop has a stem portion less than 3 base pairs in length. In some embodiments, the one lengthwise-asymmetric stem-loops has a loop portion having 3 or fewer deoxyribonucleotides. In some embodiments, the truncated cross-arm sequence has a Gibbs free energy (ΔG) of unfolding under physiological conditions in the range of 0 kcal/mol to −22 kcal/mol.

In some embodiments, the heterologous nucleic acid insert is engineered to express a protein or functional RNA. In some embodiments, the heterologous nucleic acid insert is a promoterless construct as a substrate for gene editing. In some embodiments, the promoterless construct provides a substrate for TALENS, zinc finger nucleases (ZFNs), meganucleases, Cas9, and other gene editing proteins. In some embodiments, the promoterless construct is flanked by nucleic acid with homology to cell DNA to promote homologous recombination into the cell genome. In some embodiments, the construct is flanked by nucleic acid with homology to cell DNA to promote homologous recombination into the cell genome.

In some embodiments, the nucleic acid is in the range of 500 to 50,000 nucleotides in length. In some embodiments, the nucleic acid is in the range of 500 to 10,000 nucleotides in length. In some embodiments, the nucleic acid is in the range of 1000 to 10,000 nucleotides in length. In some embodiments, the nucleic acid is in the range of 500 to 5,000 nucleotides in length.

In some aspects, the disclosure provides a composition comprising a plurality of nucleic acids as described by the disclosure. In some embodiments, the plurality of nucleic acids is linked end-to-end. In some aspects, the disclosure provides a composition comprising a nucleic acid as described by the disclosure and a pharmaceutically acceptable carrier.

In some aspects, the disclosure provides a composition comprising: a monomeric nucleic acid comprising a single subunit; and, at least one multimeric nucleic acid comprising two or more subunits, wherein each subunit of the monomeric nucleic acid and of the at least one multimeric nucleic acid comprises a heterologous nucleic acid insert flanked by interrupted self-complementary sequences, each self-complementary sequence having an operative terminal resolution site and a rolling circle replication protein binding element, wherein one self-complementary sequence is interrupted by a cross-arm sequence forming two opposing, lengthwise-symmetric stem-loops and the other of the self-complementary sequences is interrupted by a truncated cross-arm sequence. In some embodiments, each multimer has at least one, and in some cases only one, self-complementary terminal palindrome.

In some embodiments, the at least one multimeric nucleic acid is a comprises two subunits. In some embodiments, multimeric nucleic acid has no more than two subunits. In some embodiments, the two subunits are linked in a tail-to-tail configuration, or head-to-head configuration, or a head-to-tail configuration.

In some aspects, the disclosure provides host cell comprising the nucleic acid as described by the disclosure. In some embodiments, the host cell further comprises a rolling circle replication protein that selectively binds to the rolling circle replication protein binding element of the nucleic acid.

In some embodiments, the disclosure provides a method of delivering a heterologous nucleic acid to a cell, the method comprising delivering to the cell a nucleic acid as described by the disclosure.

In some aspects, the disclosure provides a method of delivering a heterologous nucleic acid to a subject, the method comprising delivering to the subject a nucleic acid as described by the disclosure, wherein the delivery of the nucleic acid does not result in eliciting an acquired immune response against the nucleic acid in the subject. In some embodiments, the immune response is a humoral response. In some embodiments, the immune response is a cellular response.

In some embodiments, the heterologous nucleic acid is delivered on multiple occasions to the subject. In some embodiments, the number of occasions in which heterologous nucleic acid is delivered (e.g., administered) to the subject is in a range of 2 to 10 times. In some embodiments, the number of occasions in which heterologous nucleic acid is delivered to the subject is hourly, daily weekly, biweekly, monthly, quarterly, semi-annually, or annually. In some embodiments, the number of occasions in which heterologous nucleic acid is delivered to the subject is the number of occasions as required to maintain a clinical (e.g., therapeutic) benefit.

In some aspects the disclosure provides a method of delivering a heterologous nucleic acid to a subject, the method comprising delivering a host cell as described by the disclosure to the subject. In some embodiments, the host cell is a blood cell. In some embodiments, the host cell is a progenitor (e.g., hematopoietic stem cell, HSC), myeloid, or lymphoid cell. In some embodiments, the host cell is delivered on multiple occasions. In some embodiments, the frequency at which the host cell is delivered on multiple occasions is determined by the half-life of the host cell. In some embodiments, the host cell is delivered on multiple occasions to achieve (e.g., achieve and maintain) therapeutic benefit.

In some aspects, the disclosure provides a method of preparing nucleic acids, the method comprising: (i) introducing into a permissive cell a nucleic acid encoding a heterologous nucleic acid insert flanked by at least one interrupted self-complementary sequence, each self-complementary sequence having an operative terminal resolution site and a rolling circle replication protein binding element, wherein the self-complementary sequence is interrupted by a cross-arm sequence forming two opposing, lengthwise-symmetric stem-loops, each of the opposing lengthwise-symmetric stem-loops having a stem portion in the range of 5 to 15 base pairs in length and a loop portion having 2 to 5 unpaired deoxyribonucleotides; and, (ii) maintaining the permissive cell under conditions in which a rolling circle replication protein in the permissive cell initiates production of multiple copies of the nucleic acid.

In some embodiments, the method further comprises the step of purifying the multiple copies of the nucleic acid. In some embodiments, the purification comprises contacting the nucleic acid with a silica gel resin.

In some embodiments, the rolling circle replication protein is selected from the group consisting of wild-type AAV Rep 78, AAV Rep 52, AAV Rep 68, and AAV Rep 40. In some embodiments, the set of rolling circle replication proteins include at least one from AAV Rep 78 and AAV Rep 68, and one from AAV Rep 52 and AAV Rep 40. In some embodiments, rolling circle replication proteins are functionally equivalent derivatives of wild-type AAV Rep proteins including truncated proteins or fusion proteins.

In some embodiments, the permissive cell is not a mammalian cell. In some embodiments, the permissive cell is an insect or other invertebrate-species cell line, yeast cell line, or bacterial cell line. In some embodiments, the permissive cell is used for production, e.g., *Spodoptera frugiperda* larva. In some embodiments, occluded recombinant *Autograph californica* multiple nucleopolyhedrosis virus (AcMNPV) have been used to infect *S. frugiperda* larvae for recombinant protein production, for example via a current good manufacturing practice (cGMP) process for protein production in larvae.

In some embodiments, the rolling circle replication protein is encoded by a helper virus vector, optionally wherein the helper virus vector is *Autograph californica* multiple nucleopolyhedrosis virus (AcMNPV) vector or a baculovirus expression vectors (BEV).

In some aspects, the disclosure provides a method of preparing nucleic acids, the method comprising: introducing into a permissive cell a nucleic acid comprising a heterologous nucleic acid insert flanked by interrupted self-complementary sequences, each self-complementary sequence having an operative terminal resolution site and a rolling circle replication protein binding element, wherein one self-complementary sequence is interrupted by a cross-arm sequence that forms two opposing, lengthwise-symmetric stem-loops, wherein the other of the self-complementary sequences is interrupted by a truncated cross-arm sequence, wherein the permissive cell expresses a rolling circle replication protein, but does not express viral capsid proteins capable of packaging replicative copies of the nucleic acid into a viral particle; and maintaining the permissive cell under conditions in which the rolling circle replication protein in the permissive cell replicates the nucleic acid.

In some aspects, the disclosure provides a method of preparing nucleic acids, the method comprising: introducing into a permissive cell a nucleic acid comprising a heterologous nucleic acid insert flanked by interrupted self-complementary sequences, each self-complementary sequence having an operative terminal resolution site and a rolling circle replication protein binding element, wherein one self-complementary sequence has been determined to be interrupted by a cross-arm sequence that forms two opposing, lengthwise-symmetric stem-loops, wherein the other of the self-complementary sequences has been determined to be interrupted by a truncated cross-arm sequence, wherein the permissive cell expresses a rolling circle replication protein, but does not express viral capsid proteins capable of packaging replicative copies of the nucleic acid into a viral particle; and maintaining the permissive cell under conditions in which the rolling circle replication protein in the permissive cell replicates the nucleic acid.

In some embodiments, the method further comprises isolating the replicated nucleic acid from the permissive cell.

In some aspects, the disclosure provides a method of analyzing a nucleic acid, the method comprising: obtaining a nucleic acid preparation comprising nucleic acid replication products isolated from a permissive cell, wherein the permissive cell comprises a nucleic acid comprising a heterologous nucleic acid insert flanked by interrupted self-complementary sequences, each self-complementary sequence having an operative terminal resolution site and a rolling circle replication protein binding element, wherein one self-complementary sequence is interrupted by a cross-arm sequence that forms two opposing, lengthwise-symmetric stem-loops, wherein the other of the self-complementary sequences is interrupted by a truncated cross-arm sequence, wherein the permissive cell expresses a rolling circle replication protein, but does not express viral capsid proteins capable of packaging replicative copies of the nucleic acid into a viral particle, and wherein the rolling circle replication protein binds to the rolling circle replication protein binding element of the nucleic acid and replicates the nucleic acid to produce nucleic acid replication products; and determining a physiochemical property of one or more replication products.

In some embodiments, the physiochemical property is the nucleotide sequence of one or each self-complementary sequence.

In some embodiments, the physiochemical property is the extent of multimerization of one or more replication products. In some embodiments, the physiochemical property is the stoichiometry of monomeric and/or multimeric forms of the replication product in the nucleic acid preparation.

In some embodiments, the physiochemical property is the susceptibility of one or more replication products to digestion with a restriction endonuclease.

In some embodiments, the physiochemical property is the polarity of monomers in a dimeric form of the replication product, wherein the polarity is head-to-head, head-to-tail or tail-to-tail.

In some embodiments, the physiochemical property is the molecular weight of one or more replication products or of a fragment of a replication product. In some embodiments, the molecular weight is of a fragment of the one or more replication products that comprises one or each self-complementary sequence. In some embodiments, the molecular weight is determined based on electrophoretic mobility. In some embodiments, the molecular weight is determined based on mass spectroscopy.

In some embodiments, the molecular weight is of a fragment of the one or more replication products, and wherein prior to determining the molecular weight the fragment is amplified by a reaction comprising primer extension by a polymerase. In some embodiments, the reaction comprising primer extension is a polymerase chain reaction.

BRIEF DESCRIPTION OF DRAWINGS

Figure 1A:
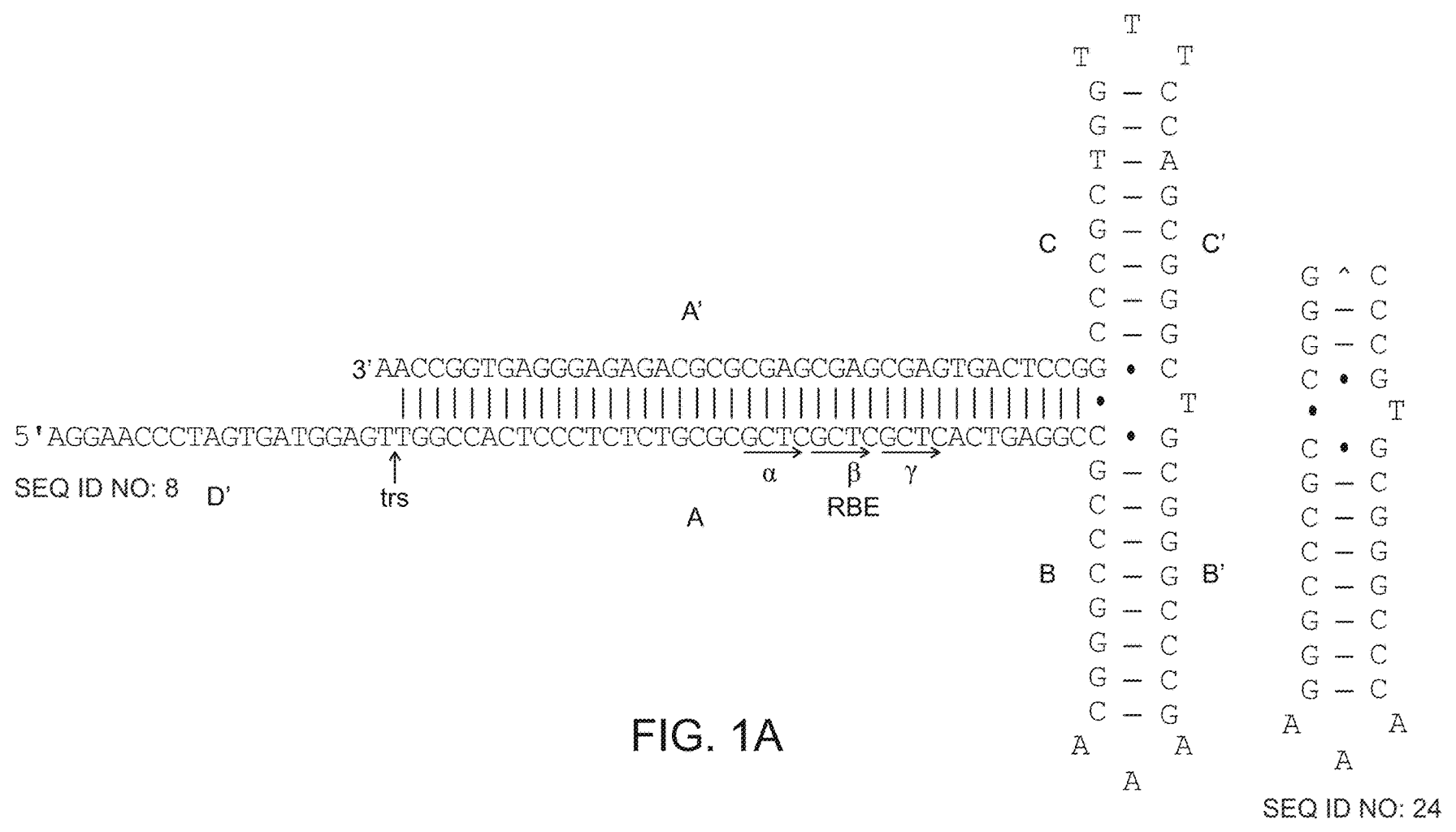

FIG. 1A shows the theoretical secondary structure of AAV2 ITR based on maximizing the stability and decreasing the Gibb's free energy (ΔG, negative values indicate spontaneous formation).

FIG. 2A shows several non-limiting examples of nucleic acids having symmetric termini (left box) and several non-limiting examples of nucleic acids having asymmetric termini (e.g., ceDNA) (right box). FIG. 2B shows asymmetric terminal regions induce alteration of nucleic acid nicking and strand separation induced during viral replication, resulting in formation of closed-ended duplex DNA molecules (right).

FIG. 8A shows a flat mount of GFP fluorescence on a mouse retina. FIG. 8B shows GFP fluorescence in a cross section of the retina. FIG. 8C shows GFP fluorescence and glial cell staining in a cross section of the retina. FIG. 8D shows GFP fluorescence in mouse retina after delivery of ceDNA (e.g., ceDNA having asymmetric interrupted self-complementary sequences) by sub-retinal electroporation (top) and intravitreal injection (bottom).

FIG. 9A shows staining for GFP expression at 3 wks and 20 wks post-injection; similar GFP expression was seen at 3 wks and 20 wks. FIGS. 9B and 9C show immunohistochemistry (IHC) with antibodies (Abs) against Iba1 (FIG. 9B) and MHCII (FIG. 9C); at 3 wks, no MHCII or Iba1 antigen was detected in the brain sections.

FIGS. 10A-10B show results of a sequence analysis of the plasmid DNA interrupted self-complementary sequences.

DETAILED DESCRIPTION

Figure 1B:
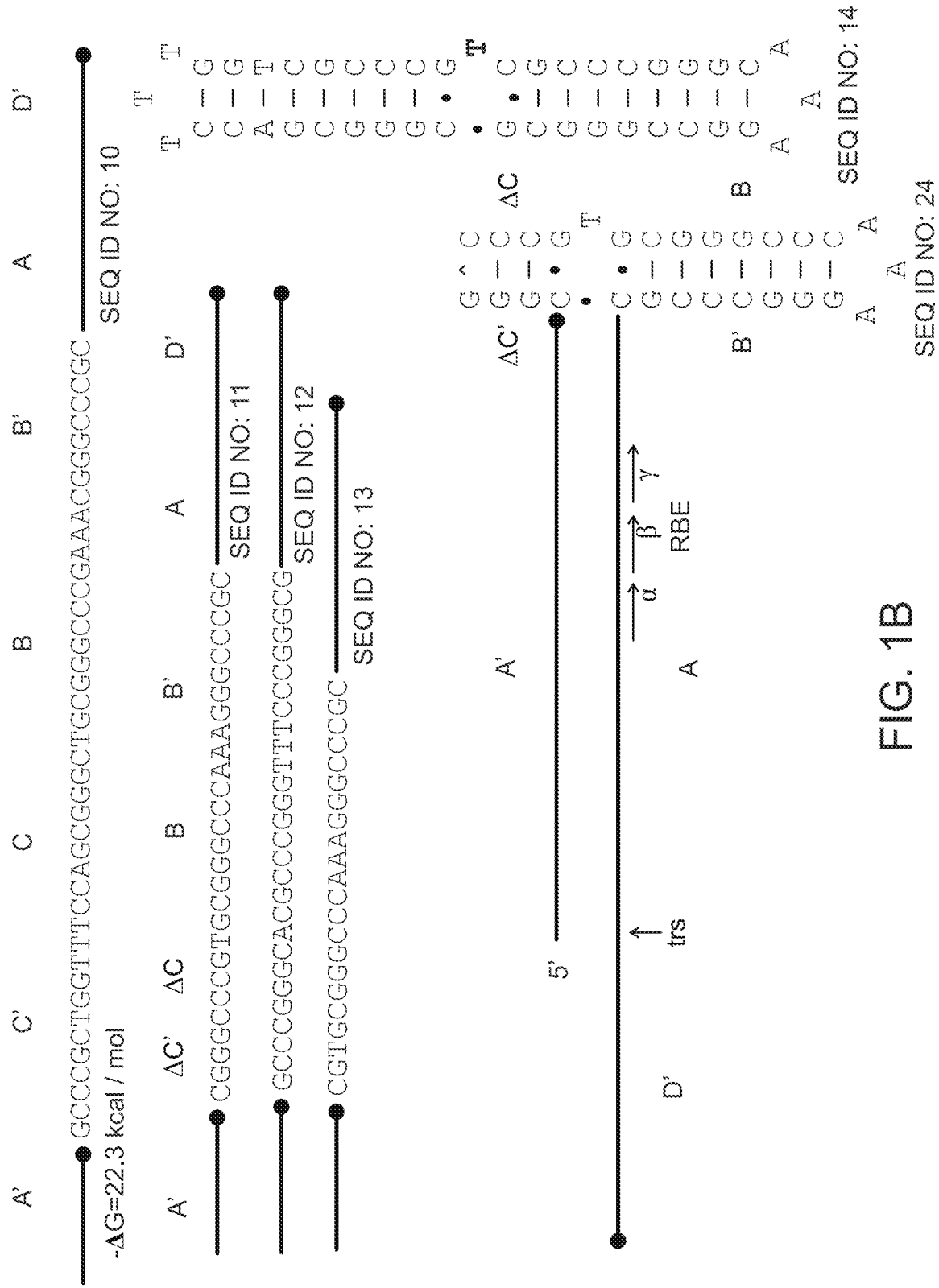
FIG. 1B shows several non-limiting examples of truncations in the stem-region of the AAV2 ITR that result in a nucleic acid molecule having asymmetric termini.

The disclosure relates in some aspects to compositions and methods for delivery of a transgene to a subject (e.g., a cell of a subject, or a tissue of a subject). The disclosure relates, in part, to the discovery that replication of nucleic acids encoding a heterologous nucleic acid insert flanked by certain types of asymmetric terminal sequences (e.g., asymmetric interrupted self-complementary sequences) results in covalent linkage of the asymmetric terminal sequences and leads to the production of a novel conformation of closed-ended linear duplex DNA (ceDNA). In some embodiments, nucleic acids having asymmetric interrupted self-complementary sequences may have improved expression, replication (e.g., production yield) in a subject compared to currently used gene therapy vectors. In some embodiments, improved expression of nucleic acids comprising asymmetric interrupted self-complementary sequences is related to a preference of RecQ helicases (e.g., RecQ1) to interact with nucleic acids comprising symmetric interrupted self-complementary sequences compared to nucleic acids having asymmetric interrupted self-complementary sequences.

In some embodiments, nucleic acids having asymmetric interrupted self-complementary sequences (e.g., are derived from a different organism or viral serotype, or are derived from the same organism or viral serotype but have different lengths, or a combination of the foregoing) may have reduced likelihood of insertional mutagenesis in a subject compared to currently used gene therapy vectors. In some embodiments, administration of nucleic acids having asymmetric interrupted self-complementary sequences induce a reduced immune response, or do not induce a detectable immune response, in a subject relative to plasmid DNA vectors.

A "nucleic acid" sequence refers to a DNA or RNA sequence. In some embodiments, proteins and nucleic acids of the disclosure are isolated. As used herein, the term "isolated" means artificially produced. In some embodiments, with respect to nucleic acids, the term "isolated" refers to a nucleic acid that is: (i) amplified in vitro by, for example, polymerase chain reaction (PCR); (ii) recombinantly produced by molecular cloning; (iii) purified, as by restriction endonuclease cleavage and gel electrophoretic fractionation, or column chromatography; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. For example, in some embodiments, conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of proteins and polypeptides disclosed herein.

Interrupted Self-Complementary Sequences

The disclosure is based, in part, on the discovery that nucleic acids having asymmetric terminal sequences (e.g., asymmetric interrupted self-complementary sequences) form closed-ended linear duplex DNA structures (e.g., ceDNA) that, in some embodiments, exhibit reduced immunogenicity compared to currently available gene delivery vectors. In some embodiments, ceDNA behaves as linear duplex DNA under native conditions and transforms into single-stranded circular DNA under denaturing conditions. Without wishing to be bound by any particular theory, nucleic acids described by the disclosure (e.g., ceDNA) are useful, in some embodiments, for the delivery of heterologous nucleic acid inserts (e.g., transgenes) to a subject.

In some aspects, the disclosure provides a nucleic acid comprising a heterologous nucleic acid insert flanked by interrupted self-complementary sequences, each self-complementary sequence having an operative terminal resolution site and a rolling circle replication protein binding element, wherein one self-complementary sequence is interrupted by a cross-arm sequence forming two opposing, lengthwise-symmetric stem-loops, each of the opposing lengthwise-symmetric stem-loops having a stem portion and a loop portion, wherein the other of the self-complementary sequences is interrupted by a truncated cross-arm sequence.

As used herein, the term "flanked" refers to the positioning of a first interrupted self-complementary sequence upstream (e.g., 5') relative to a heterologous nucleic acid insert and a second interrupted self-complementary sequence downstream (e.g., 3') relative to the heterologous nucleic acid insert. For example, an adeno-associated virus genome comprises open reading frames of the rep and cap genes "flanked" by inverted terminal repeats (ITRs).

As used herein, the term "interrupted self-complementary sequence" refers to a polynucleotide sequence encoding a nucleic acid having palindromic (e.g., a contiguous stretch of polynucleotides that is identical to its complementary strand, if both are "read" in the same 5' to 3' direction) terminal sequences that are interrupted by one or more stretches of non-palindromic polynucleotides. Generally, a polynucleotide encoding one or more interrupted palindromic sequences will fold back upon itself, forming a stem-loop structure (e.g., a hairpin loop, a "T"-shaped loop, or a "Y"-shaped loop), for example as shown in the AAV2 ITR structure depicted in FIG. 1A and the exemplary structures depicted in FIG. 2A.

In some embodiments, an interrupted self-complementary sequence forms a "T"-shaped structure having a stem sequence and a cross-arm sequence. In some embodiments, the "cross-arm sequence" forms two opposing (e.g., relative to the stem sequence), lengthwise-symmetric stem-loops, each of the opposing lengthwise-symmetric stem-loops having a stem portion and a loop portion. For example, in some embodiments, the stem sequence is formed by hybridization of the complementary (e.g., palindromic) 5'- and 3'-ends of a polynucleotide sequence (referred to as "A-A'"), where the A-A' palindrome is interrupted by the cross-arm polynucleotide sequence formed by a pair of loop-forming interrupted palindromic sequences denoted "B-B'" and "C-C'", respectively, as shown in FIG. 1A. In some embodiments, the loop portion of each cross arm (e.g., loops formed by interrupted palindromic sequences B-B' and C-C') is formed from unpaired nucleotides (e.g., unpaired deoxyribonucleotides). It should be appreciated that an interrupted self-complementary sequence described by the disclosure may comprise more than two (e.g., 3, 4, or more) cross-arm sequences.

An interrupted self-complementary sequence can be of any size, provided that the sequence forms a hairpin loop and functions as a primer for nucleic acid replication (e.g., DNA replication). For example, an interrupted self-complementary sequence can range from about 20 to about 2000 nucleotides in length. In some embodiments, an interrupted self-complementary sequence ranges from about 40 to 1000 nucleotides in length. In some embodiments, an interrupted self-complementary sequence is at least 40, at least 50, at least 60, at least 70, at least 80, at least 90, at least 100, at least 200, at least 300, at least 400, at least 500, at least 600, at least 700, at least 800, at least 900, or up to 1000 nucleotides in length. In some embodiments, an interrupted self-complementary sequence is more than 1000 nucleotides in length. In some embodiments, an interrupted self-complementary sequence ranges from about 100 to 160 nucleotides in length. In some embodiments, an interrupted self-complementary nucleotide ranges from about 115 to about 150 nucleotides in length.

In some aspects, the disclosure relates to nucleic acid having an interrupted self-complementary sequence that forms opposing lengthwise-symmetric stem-loops. In some embodiments, each of the opposing lengthwise-symmetric stem-loops have a stem portion in the range of 3 to 15 base pairs in length. In some embodiments, each of the opposing lengthwise-symmetric stem-loops have a stem portion in the range of 8 to 10 base pairs in length. In some embodiments, each of the opposing lengthwise-symmetric stem-loops have a stem portion that is 3, 4, 5, 6, 7, 8, 9, 10, 11, 12, 13, 14, or 15 nucleotides in length.

Generally, a loop portion of a stem-loop structure comprises at least 2 unpaired nucleotides. In some embodiments, each loop portion has 2 to 5 unpaired deoxyribonucleotides (e.g., 2, 3, 4, or 5 unpaired deoxyribonucleotides). In some embodiments, each loop portion of a cross-arm sequence described by the disclosure has three deoxyribonucleotides. In some embodiments, one loop portion of a cross-arm sequence described by the disclosure has three deoxythymidines and the other loop portion has three deoxyadenosines.

In some aspects, the disclosure relates to interrupted self-complementary sequences flanking a nucleic acid insert, where the interrupted self-complementary sequences are asymmetric with respect to one another (e.g., are derived from a different organism or viral serotype, or are derived from the same organism or viral serotype but have different lengths, or a combination of the foregoing). In some embodiments, one of a pair of asymmetric self-complementary sequences comprises a truncated cross-arm sequence. As used herein, "truncated cross-arm sequence" refers to a cross-arm sequence that has a shorter length relative to the corresponding self-complementary sequence flanking a heterologous nucleic acid sequence. A truncated cross-arm sequence can have between 1 and 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) nucleotide deletions relative to a full-length cross-arm sequence. In some embodiments, a truncated cross-arm sequence has between 1 and 30 nucleotide deletions relative to a full-length cross-arm sequence. In some embodiments, a truncated cross-arm sequence contains between 2 and 20 nucleotide deletions relative to a full-length cross-arm sequence.

In some embodiments, a truncated cross-arm sequence forms two opposing, lengthwise-asymmetric stem-loops. In some embodiments, one of the opposing, lengthwise-asymmetric stem-loops of the truncated cross-arm sequence has a stem portion in the range of 8 to 10 base pairs in length and a loop portion having 2 to 5 unpaired deoxyribonucleotides. In some embodiments, a one lengthwise-asymmetric stem-loop of a truncated cross-arm sequence has a stem portion less than 8 base pairs in length and a loop portion having 2 to 5 deoxyribonucleotides. In some embodiments, the one lengthwise-asymmetric stem-loop has a stem portion less than 3 base pairs in length. In some embodiments, the one lengthwise-asymmetric stem-loops has a loop portion having 3 or fewer deoxyribonucleotides.

Generally, a truncated cross-arm sequence does not contain any nucleotide deletions (e.g., relative to a non-truncated cross-arm sequence) in the A or A' regions, so as not to interfere with DNA replication (e.g., binding to a RBE by Rep protein, or nicking at a terminal resolution site). In some embodiments, a truncated cross-arm sequence has one or more deletions in the B, B', C, and/or C' region. Several non-limiting examples of truncated cross-arm sequences are shown below:

---

AAV2 ITR Δ C-region indicated by parenthesis; all or partial deletions within the square brackets can be used to create asymmetric interrupted self-complementary sequences; below, "RBE'" refers to "Rep-binding element".

---

| C-Region | B-Region |
|---|---|
| Δ | RBE' |

5'cggg(cgaccaaaggtc)gcccg-a-cgcccgggctttgcccgggc (SEQ ID NO: 2)

5'cggg(cgaccaaaggtcg)cccg-a-cgcccgggctttgcccgggc (SEQ ID NO: 2)

5'gccc(gggcaaagccc)gggcg-t-cgggcgacctttggtcgcccg (SEQ ID NO: 3)

5'gccc(gggcaaagccc)gggcg-t-cgggcgacctttggtcgcccg (SEQ ID NO: 3)

5'[cgggcgaccaaaggtcgcccg]-a-cgcccgggctttgcccgggc (SEQ ID NO: 2)

5'[cgggcgaccaaaggtcgcccg]-a-cgcccgggctttgcccgggc (SEQ ID NO: 2)

5'[gcccgggcaaagcccgggcg]-t-cgggcgacctttggtcgcccg (SEQ ID NO: 3)

5'[gcccgggcaaagcccgggcg]-t-cgggcgacctttggtcgcccg (SEQ ID NO: 3)

Generally, the thermodynamic properties of a nucleic acid (e.g., Gibbs free energy (ΔG), G+C composition, A+T composition, melting temperature, base composition of each strand, length of complementary sequence, unpaired bases within the duplex region, and unpaired bases constituting the loop) required for hairpin formation are known in the art, for example as disclosed in Bosco et al., *Nucl. Acids Res.* (2013) doi: 10.1093/nar/gkt1089; First published online: Nov. 12, 2013.

In some embodiments, the cross-arm sequence has a Gibbs free energy (ΔG) of unfolding under physiological conditions in the range of −12 kcal/mol to −30 kcal/mol. In some embodiments, the cross-arm sequence has a Gibbs free energy (ΔG) of unfolding under physiological conditions in the range of −20 kcal/mol to −25 kcal/mol. In some embodiments, the thermodynamic properties of a truncated cross-arm sequence can be the same (e.g., identical) relative to a full-length cross-arm sequence even though they may have sequence differences that render them asymmetric. In some embodiments, the thermodynamic properties of a truncated cross-arm sequence can be the different than those of a full-length cross-arm sequence. For example, in some embodiments, a truncated cross-arm sequence has a Gibbs free energy (ΔG) of unfolding under physiological conditions in the range of 0 kcal/mol to greater than −22 kcal/mol.

As used herein, the term "operative" refers to the ability of a nucleic acid sequence to perform its intended function. For example, an "operative binding region" is a nucleic acid sequence that retains binding function for its intended target (e.g., a protein or nucleic acid). In another example, an "operative cleavage site" is a nucleic acid sequence that retains its ability to be specifically cleaved by a particular enzyme or enzymes.

Aspects of the disclosure relate to the discovery that self-complementary nucleic acid sequences comprising an operative rolling circle replication protein binding element is required for the formation of closed-ended linear duplex DNA (ceDNA). As used here, "rolling circle replication protein binding element" refers to a conserved nucleic acid sequence (e.g., motif) that is recognized and bound by a rolling circle replication protein, which is a viral nonstructural protein (NS protein) that initiates rolling circle (e.g., rolling hairpin) replication. Rolling circle (e.g., rolling hairpin) replication is described by Tattersall et al. Nature 2009, 263, pp. 106-109. Examples of NS proteins include, but are not limited to AAV Rep proteins (e.g., Rep78, Rep68, Rep52, Rep40), parvovirus nonstructural proteins (e.g., NS2), rotavirus nonstructural proteins (e.g., NSP1), and densovirus nonstructural proteins (e.g., PfDNV NS1). In some embodiments, the rolling circle replication protein binding element is a Rep binding element (RBE). In some embodiments, the RBE comprises the sequence 5'-GCTCGCTCGCTC-3'.

In some embodiments, rolling circle replication proteins are from the dependoparvovirus genus of the Parvoviridae family of viruses with linear single-stranded DNA genomes. In some embodiments, the rolling circle replication proteins are from the genera of the autonomous Parvovirinae including mice minute virus, Aleutian mink disease virus, bovine parvovirus, canine parvovirus, chicken parvovirus, feline panleukopenia virus, feline parvovirus, goose parvovirus, HB parvovirus, H-1 parvovirus, Kilham rat virus, lapine parvovivirus, LUIII virus, mink enteritis virus, mouse parvovirus, porcine parvovirus, raccoon parvovivurs, RT parvovirus, Tumor virus X, rat parvovirus 1a, barbarie duck parvovirus, equine parvovirus, hamster parvovirus, and rheumatorid arthritis virus 1. In some embodiments, the genus is parvovirus. In some embodiments, the rolling circle replication proteins are from the genera of Densovirinae including brevidensovirus, densovirus, and iteravirus.

In some embodiments, a rolling circle replication protein is from the genera of the subfamily Parvovirinae. Examples of Parvovirinae genera include but are not limited to Amdoparvovirus, Aveparvovirus, Bocaparvovirus, Copiparvovirus, Dependoparvovirus, Erythroparvovirus, Protoparvovirus, Tetraparvovirus. In some embodiments, the rolling circle replication proteins are from the genera of the subfamily, Densovirinae. Examples of Densovirinae genera include but are not limited to Amdoparvovirus, Aveparvovirus, Bocaparvovirus, Copiparvovirus, Dependoparvovirus, Erythroparvovirus, Protoparvovirus, and Tetraparvovirus. In some embodiments, the rolling circle replication protein(s) is from a Dependovirus, such as Adeno-associated virus 2 (AAV2), Adeno-associated virus 3 (AAV3), Adeno-associated virus 4 (AAV4), or Adeno-associated virus 5 (AAV5), or any combination thereof.

In some embodiments, the rolling circle replication proteins are derived from the single-stranded DNA bacteriophage families. In some embodiments, the virus families are the Microviridae and the Inoviridae.

In some embodiments, the rolling circle replication proteins are derived from Gram positive bacteria.

Aspects of the disclosure relate to the discovery that interrupted self-complementary nucleic acid sequences comprising an operative terminal resolution site (trs) are required for the formation of closed-ended linear duplex DNA (ceDNA). Typically, replication of nucleic acids comprising interrupted self-complementary nucleic acid sequences (e.g., AAV ITRs) is initiated from the 3' end of the cross-arm (e.g., hairpin structure) and generates a duplex molecule in which one of the ends is covalently closed; the covalently closed ends of the duplex molecule are then cleaved by a process called terminal resolution to form a two separate single-stranded nucleic acid molecules. Without wishing to be bound by any particular theory, the process of terminal resolution is mediated by a site- and strand-specific endonuclease cleavage at a terminal resolution site (trs) (e.g., a rolling circle replication protein, such as AAV Rep protein). Examples of trs sequences include 3'-CCGGTTG-5 and 5'-AGTTGG-3' (recognized by AAV2 p5 protein). It has been hypothesized that Rep-mediated strand nicking takes place between the central di-thymidine ("TT") portion of the trs sequence. Therefore, in some embodiments, the operative terminal resolution site comprises a sequence 5'-TT-3'.

Aspects of the disclosure relate to the positioning of a terminal resolution site (trs) relative to a rolling circle replication protein binding element. Generally, a trs is positioned upstream (e.g., 5') relative to a rolling circle replication protein binding element. However, in some embodiments, a trs is positioned downstream (e.g., 3') relative to a rolling circle replication protein binding element. In some embodiments, the 3' end of the operative terminal resolution site is 15 to 25 nucleotides (e.g., 15, 16, 17, 18, 19, 20, 21, 22, 23, 24, or 25 nucleotides) from the 5' end of the rolling circle replication protein binding element.

In some embodiments, an interrupted self-complementary sequence is an AAV inverted terminal repeat sequence. The AAV ITR sequence can be of any AAV serotype, including but not limited to, AAV1, AAV2, AAV3, AAV4, AAV5, AAV6, AAV7, AAV8, AAV9, non-human primate AAV serotypes (e.g., AAVrh.10), and variants thereof. In some embodiments, an interrupted self-complementary sequence is an AAV2 ITR or a variant thereof (e.g., AAV2 ITR, or a truncated AAV2 ITR having a deletion in the "B arm" or "C arm"). In some embodiments, an interrupted self-complementary sequence is an AAV5 ITR or a variant thereof (e.g., AAV5 ITR, or a truncated AAV5 ITR having a deletion in the "B arm" or "C arm"). As used herein, a "variant" of an AAV ITR is a polynucleotide having between about 70% and about 99.9% similarity to a wild-type AAV ITR sequence. In some embodiments, an AAV ITR variant is about 70%, about 75%, about 80%, about 85%, about 90%, about 95%, or about 99% identical to a wild-type AAV ITR.

An AAV ITR can exist in two conformations: "flip" and "flop", which are a result of the rolling hairpin mechanism of AAV replication. A non-limiting example of an interrupted self-complementary sequence (e.g., AAV2 ITR) in both "flip" and "flop" conformations is shown below:

element, wherein one self-complementary sequence is interrupted by a cross-arm sequence forming two opposing, lengthwise-symmetric stem-loops and the other of the self-complementary sequences is interrupted by a truncated cross-arm sequence. In some embodiments, the multimeric nucleic acid comprises two subunits (e.g., is a dimer). In some embodiments, each multimer has at least one, and in some cases only one, self-complementary terminal palindrome.

In some embodiments, the subunits of a multimeric nucleic acid form concatamers. As used herein, "concatamer" refers to a nucleic acid molecule comprising multiple copies of the same or substantially the same nucleic acid sequences (e.g., subunits) that are typically linked in a

```
GenBank (>gi|110645916|ref|NC_001401.2| Adeno-associated virus - 2, com-
plete genome)
Flop conformation
                                                                (SEQ ID NO: 4)
ttggccactccctctctgcgcgctcgctcgctcactgaggc_cgggcgaccaaaggtcgcccgacgcccgggctttg
|||||||||||||||||||||||||||||||||||||||| |||||||||||||||||||||||||||| | | |
aaccggtgagggagagacgcgcgagcgagcgagtgactccg_gcccgctggtttccagcgggctgcgggcccgaaac (SEQ ID NO: 5)
cccgggc_ggcctcagtgagcgagcgagcgcgcagagagggagtggccaactccatcactagggggttcct
||||||| |||||||||||||||||||||||||||||||||||||||||||||||||||||||||||||
gggcccg_ccggagtcactcgctcgctcgcgcgtctctccctcaccggttgaggtagtgatccccaagga Flip conformation
                                                                (SEQ ID NO: 6)
aggaaccccctagtgatggagttggccactccctctctgcgcgctcgctcgctcactgaggcc_gggcgaccaaaggt
||||||||||||||||||||||||||||||||||||||||||||||||||||||||||||| ||||||||||||||
tccttggggatcactacctcaaccggtgagggagagacgcgcgagcgagcgagtgactccgg_cccgctggtttcca (SEQ ID NO: 7)
cgcccgacgcccgggctttgcccgggcg_gcctcagtgagcgagcgagcgcgcagagagggagtggccaa
|||||||||||||||||||||||||||| |||||||||||||||||||||||||||||||||||||||
gcgggctgcgggcccgaaacgggcccgc_cggagtcactcgctcgctcgcgcgtctctccctcaccggtt
```

In some embodiments, a nucleic acid described by the disclosure (e.g., ceDNA) comprises an interrupted self-complementary sequence in the flip conformation. In some embodiments, a nucleic acid described by the disclosure (e.g., ceDNA) comprises an interrupted self-complementary sequence in the flop conformation.

Aspects of the disclosure relate to compositions comprising a population of nucleic acids described by the disclosure. Generally, the populations may be homogenous (e.g., comprising multiple copies of the same nucleic acid) or heterogeneous (e.g., comprising multiple different nucleic acids). For example, in some embodiments, a composition comprises a monomeric nucleic acid (e.g., a population of a single species of monomeric nucleic acid) comprising a single subunit. In some embodiments, the subunit comprises a heterologous nucleic acid insert flanked by interrupted self-complementary sequences, each self-complementary sequence having an operative terminal resolution site and a rolling circle replication protein binding element, wherein one self-complementary sequence is interrupted by a cross-arm sequence forming two opposing, lengthwise-symmetric stem-loops and the other of the self-complementary sequences is interrupted by a truncated cross-arm sequence.

In some embodiments, a composition comprises a multimeric nucleic acid comprising two or more subunits (e.g., 2, 3, 4, 5, 6, 7, 8, 9, 10, or more subunits). In some embodiments, each subunit of the multimeric nucleic acid comprises a heterologous nucleic acid insert flanked by interrupted self-complementary sequences, each self-complementary sequence having an operative terminal resolution site and a rolling circle replication protein binding series. In some embodiments, concatamers described by the disclosure can be orientated in either a head-to-head polarity, or a tail-to-tail polarity. In embodiments in which subunits contain a heterologous nucleic acid sequence configured to express an RNA transcript, "head-to-head" polarity refers to a concatamer in which the interrupted self-complementary sequences closest to the promoter sequence of each subunit are covalently linked (e.g., the subunits are linked 5'-end to 5'-end). In such embodiments, "tail-to-tail" polarity refers to a concatamer in which the interrupted self-complementary sequences distal to the promoter sequence of each subunit are covalently linked (e.g., the subunits are linked 5'-end to 5'-end). In some embodiments, the two subunits are linked in a tail-to-tail configuration (e.g., polarity).

In some embodiments, a composition comprises both monomeric and multimeric nucleic acids (e.g., comprises a heterogeneous population of nucleic acids).

Heterologous Nucleic Acid Inserts

The composition of the transgene sequence (e.g., heterologous nucleic acid insert) of the nucleic acid will depend upon the use to which the resulting nucleic acid will be put. For example, one type of transgene sequence includes a reporter sequence, which upon expression produces a detectable signal. In another example, the transgene encodes a therapeutic protein or therapeutic functional RNA. In another example, the transgene encodes a protein or functional RNA that is intended to be used for research purposes, e.g., to create a somatic transgenic animal model harboring the transgene, e.g., to study the function of the transgene product. In another example, the transgene encodes a protein or functional RNA that is intended to be used to create an animal model of disease. Appropriate transgene coding sequences will be apparent to the skilled artisan.

The disclosure is based, in part, on the discovery that unlike AAV vectors, nucleic acids described herein (e.g., ceDNA) are not limited with respect to the size of a heterologous nucleic acid insert (e.g., transgene sequence). In some embodiments, a transgene (e.g., heterologous nucleic acid insert) flanked by interrupted self-complementary sequences ranges from about 10 to about 5,000 base pairs, about 10 to about 10,000 base pairs, about 10 to about 50,000 base pairs in length. In some embodiments, a transgene (e.g., heterologous nucleic acid insert) flanked by interrupted self-complementary sequences ranges from about 10 to about 50 base pairs in length. In some embodiments, a transgene (e.g., heterologous nucleic acid insert) flanked by interrupted self-complementary sequences ranges from about 20 to about 100 base pairs in length. In some embodiments, a transgene (e.g., heterologous nucleic acid insert) flanked by interrupted self-complementary sequences ranges from about 500 to about 1500 base pairs in length. In some embodiments, a transgene (e.g., heterologous nucleic acid insert) flanked by interrupted self-complementary sequences ranges from about 1000 to about 5000 base pairs in length. In some embodiments, the size of a transgene (e.g., heterologous nucleic acid insert) exceeds the capacity of a traditional AAV vector (e.g., exceeds about 4.8 kb).

Reporter sequences that may be provided in a transgene include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer. Such reporters can, for example, be useful in verifying the tissue-specific targeting capabilities and tissue specific promoter regulatory activity of a nucleic acid.

In some aspects, the disclosure provides nucleic acids for use in methods of preventing or treating one or more genetic deficiencies or dysfunctions in a mammal, such as for example, a polypeptide deficiency or polypeptide excess in a mammal, and particularly for treating or reducing the severity or extent of deficiency in a human manifesting one or more of the disorders linked to a deficiency in such polypeptides in cells and tissues. The method involves administration of nucleic acid (e.g., a nucleic acid as described by the disclosure) that encodes one or more therapeutic peptides, polypeptides, siRNAs, microRNAs, antisense nucleotides, etc. in a pharmaceutically-acceptable carrier to the subject in an amount and for a period of time sufficient to treat the deficiency or disorder in the subject suffering from such a disorder.

Thus, the disclosure embraces the delivery of nucleic acids (e.g., nucleic acids as described by the disclosure) encoding one or more peptides, polypeptides, or proteins, which are useful for the treatment or prevention of disease states in a mammalian subject. Exemplary therapeutic proteins include one or more polypeptides selected from the group consisting of growth factors, interleukins, interferons, anti-apoptosis factors, cytokines, anti-diabetic factors, anti-apoptosis agents, coagulation factors, anti-tumor factors. Other non-limiting examples of therapeutic proteins include BDNF, CNTF, CSF, EGF, FGF, G-SCF, GM-CSF, gonadotropin, IFN, IFG-1, M-CSF, NGF, PDGF, PEDF, TGF, VEGF, TGF-B2, TNF, prolactin, somatotropin, XIAP1, IL-1, IL-2, IL-3, IL-4, IL-5, IL-6, IL-7, IL-8, IL-9, IL-10, IL-10(187A), viral IL-10, IL-11, IL-12, IL-13, IL-14, IL-15, IL-16 IL-17, and IL-18.

The nucleic acids (e.g., nucleic acids as described by the disclosure) may comprise a gene to be transferred (e.g., expressed in) to a subject to treat a disease associated with reduced expression, lack of expression or dysfunction of the gene. Exemplary genes and associated disease states include, but are not limited to: glucose-6-phosphatase, associated with glycogen storage deficiency type 1A; phosphoenolpyruvate-carboxykinase, associated with Pepck deficiency; galactose-1 phosphate uridyl transferase, associated with galactosemia; phenylalanine hydroxylase, associated with phenylketonuria; branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase, associated with ornithine transcarbamylase deficiency; argininosuccinic acid synthetase, associated with citrullinemia; low density lipoprotein receptor protein, associated with familial hypercholesterolemia; UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotinidase, associated with biotinidase deficiency; beta-glucocerebrosidase, associated with Gaucher disease; beta-glucuronidase, associated with Sly syndrome; peroxisome membrane protein 70 kDa, associated with Zellweger syndrome; porphobilinogen deaminase, associated with acute intermittent porphyria; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, anti-sense to, or a mutant form of, phospholamban, the sarco(endo)plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin for the treatment of diabetes.

In some embodiments, the disclosure relates to a heterologous nucleic acid insert encoding a protein or functional RNA useful for the treatment of a condition, disease or disorder associated with the central nervous system (CNS). The following is a non-limiting list of genes associated with CNS disease: DRD2, GRIA1, GRIA2, GRIN1, SLC1A1, SYP, SYT1, CHRNA7, 3Rtau/4rTUS, APP, BAX, BCL-2, GRIK1, GFAP, IL-1, AGER, associated with Alzheimer's Disease; UCH-L1, SKP1, EGLN1, Nurr-1, BDNF, TrkB, gstm1, S106β, associated with Parkinson's Disease; IT15, PRNP, JPH3, TBP, ATXN1, ATXN2, ATXN3, Atrophin 1, FTL, TITF-1, associated with Huntington's Disease; FXN, associated with Freidrich's ataxia; ASPA, associated with Canavan's Disease; DMD, associated with muscular dystrophy; and SMN1, UBE1, DYNC1H1 associated with spinal muscular atrophy. In some embodiments, the disclosure relates to a heterologous nucleic acid insert that expresses one or more of the foregoing genes or fragments thereof. In some embodiments, the disclosure relates to a heterologous nucleic acid insert that expresses one or more functional RNAs that inhibit expression of one or more of the foregoing genes.

In some embodiments, the disclosure relates to a heterologous nucleic acid insert encoding a protein or functional RNA useful for the treatment of a condition, disease or disorder associated with the cardiovascular system. The following is a non-limiting list of genes associated with cardiovascular disease: VEGF, FGF, SDF-1, connexin 40, connexin 43, SCN4a, HIF1α, SERCa2a, ADCY1, and ADCY6. In some embodiments, the disclosure relates to a heterologous nucleic acid insert that expresses one or more of the foregoing genes or fragments thereof. In some embodiments, the disclosure relates to a heterologous nucleic acid insert that expresses one or more functional RNAs that inhibit expression of one or more of the foregoing genes.

In some embodiments, the disclosure relates to a heterologous nucleic acid insert encoding a protein or functional RNA useful for the treatment of a condition, disease or disorder associated with the pulmonary system. The following is a non-limiting list of genes associated with pulmonary disease: CFTR, AAT, TNFα, TGFβ1, SFTPA1, SFTPA2, SFTPB, SFTPC, HPS1, HPS3, HPS4, ADTB3A, IL1A, IL1B, LTA, IL6, CXCR1, and CXCR2. In some embodiments, the disclosure relates to a heterologous nucleic acid insert that expresses one or more of the foregoing genes or fragments thereof. In some embodiments, the disclosure relates to a heterologous nucleic acid insert that expresses one or more functional RNAs that inhibit expression of one or more of the foregoing genes. Non-limiting examples of heterologous nucleic acid inserts encoding a protein or functional RNA useful for the treatment of a condition, disease or disorder associated with the pulmonary system are depicted in FIG. 10.

In some embodiments, the disclosure relates to a heterologous nucleic acid insert encoding a protein or functional RNA useful for the treatment of a condition, disease or disorder associated with the liver. The following is a non-limiting list of genes associated with liver disease: α1-AT, HFE, ATP7B, fumarylacetoacetate hydrolase (FAH), glucose-6-phosphatase, NCAN, GCKR, LYPLAL1, PNPLA3, lecithin cholesterol acetyltransferase, phenylalanine hydroxylase, and G6PC. In some embodiments, the disclosure relates to a heterologous nucleic acid insert that expresses one or more of the foregoing genes or fragments thereof. In some embodiments, the disclosure relates to a heterologous nucleic acid insert that expresses one or more functional RNAs that inhibit expression of one or more of the foregoing genes. Non-limiting examples of heterologous nucleic acid inserts encoding a protein or functional RNA useful for the treatment of a condition, disease or disorder associated with the liver are depicted in FIG. 9.

In some embodiments, the disclosure relates to a heterologous nucleic acid insert encoding a protein or functional RNA useful for the treatment of a condition, disease or disorder associated with the kidney. The following is a non-limiting list of genes associated with kidney disease: PKD1, PKD2, PKHD1, NPHS1, NPHS2, PLCE1, CD2AP, LAMB2, TRPC6, WT1, LMX1B, SMARCAL1, COQ2, PDSS2, SCARB3, FN1, COL4A5, COL4A6, COL4A3, COL4A4, FOX1C, RET, UPK3A, BMP4, SIX2, CDC5L, USF2, ROBO2, SLIT2, EYA1, MYOG, SIX1, SIX5, FRAS1, FREM2, GATA3, KAL1, PAX2, TCF2, and SALL1. In some embodiments, the disclosure relates to a heterologous nucleic acid insert that expresses one or more of the foregoing genes or fragments thereof. In some embodiments, the disclosure relates to a heterologous nucleic acid insert that expresses one or more functional RNAs that inhibit expression of one or more of the foregoing genes.

Figure 7:
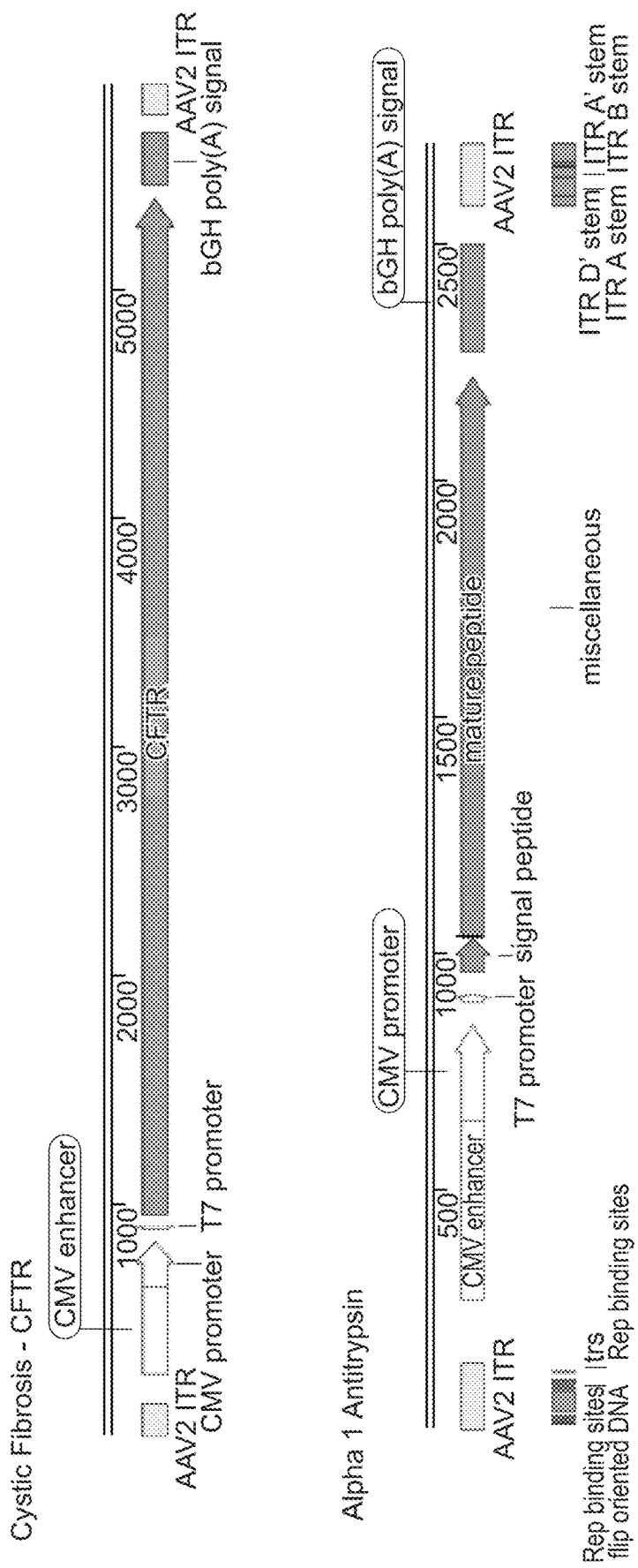
FIG. 7 shows non-limiting examples of nucleic acid constructs having asymmetric self-complementary nucleic acid sequences (e.g., AAV2 ITRs) and a transgene associated with lung disease.

In some embodiments, the disclosure relates to a heterologous nucleic acid insert encoding a protein or functional RNA useful for the treatment of a condition, disease or disorder associated with the eye. The following is a non-limiting list of genes associated with ocular disease: ABCA4, VEGF, CEP290, CFH, C3, MT-ND2, ARMS2, TIMP3, CAMK4, FMN1, RHO, USH2A, RPGR, RP2, TMCO, SIX1, SIX6, LRP12, ZFPM2, TBK1, GALC, myocilin, CYP1B1, CAV1, CAV2, optineurin and CDKN2B. In some embodiments, the disclosure relates to a heterologous nucleic acid insert that expresses one or more of the foregoing genes or fragments thereof. In some embodiments, the disclosure relates to a heterologous nucleic acid insert that expresses one or more functional RNAs that inhibit expression of one or more of the foregoing genes. Non-limiting examples of heterologous nucleic acid inserts encoding a protein or functional RNA useful for the treatment of a condition, disease or disorder associated with the eye are depicted in FIG. 7.

In some embodiments, the disclosure relates to a heterologous nucleic acid insert encoding a protein or functional RNA useful for the treatment of a condition, disease or disorder associated with the blood (e.g., red blood cells). The following is a non-limiting list of genes associated with diseases and disorders of the blood: Factor VIII (FVIII), Factor IX (FIX), von Willebrand factor (VWF). In some embodiments, the disclosure relates to a heterologous nucleic acid insert that expresses one or more of the foregoing genes or fragments thereof. In some embodiments, the disclosure relates to a heterologous nucleic acid insert that expresses one or more functional RNAs that inhibit expression of one or more of the foregoing genes. Non-limiting examples of heterologous nucleic acid inserts encoding a protein or functional RNA useful for the treatment of a condition, disease or disorder associated with the blood are depicted in FIG. 8.

The nucleic acids of the disclosure (e.g., nucleic acid having a heterologous nucleic acid insert) can be used to restore the expression of genes that are reduced in expression, silenced, or otherwise dysfunctional in a subject (e.g., a tumor suppressor that has been silenced in a subject having cancer). The nucleic acids of the disclosure can also be used to knockdown the expression of genes that are aberrantly expressed in a subject (e.g., an oncogene that is expressed in a subject having cancer). In some embodiments, a heterologous nucleic acid insert encoding a gene product associated with cancer (e.g., tumor suppressors) may be used to treat the cancer, by administering nucleic acid comprising the heterologous nucleic acid insert to a subject having the cancer. In some embodiments, a nucleic acid comprising a heterologous nucleic acid insert encoding a small interfering nucleic acid (e.g., shRNAs, miRNAs) that inhibits the expression of a gene product associated with cancer (e.g., oncogenes) may be used to treat the cancer, by administering nucleic acid comprising the heterologous nucleic acid insert to a subject having the cancer. In some embodiments, nucleic comprising a heterologous nucleic acid insert encoding a gene product associated with cancer (or a functional RNA that inhibits the expression of a gene associated with cancer) may be used for research purposes, e.g., to study the cancer or to identify therapeutics that treat the cancer. The following is a non-limiting list of exemplary genes known to be associated with the development of cancer (e.g., oncogenes and tumor suppressors): AARS, ABCB1, ABCC4, ABI2, ABL1, ABL2, ACK1, ACP2, ACY1, ADSL, AK1, AKR1C2, AKT1, ALB, ANPEP, ANXA5, ANXA7, AP2M1, APC, ARHGAP5, ARHGEF5, ARID4A, ASNS, ATF4, ATM, ATP5B, ATP5O, AXL, BARD1, BAX, BCL2, BHLHB2, BLMH, BRAF, BRCA1, BRCA2, BTK, CANX, CAP1, CAPN1, CAPNS1, CAV1, CBFB, CBLB, CCL2, CCND1, CCND2, CCND3, CCNE1, CCT5, CCYR61, CD24, CD44, CD59, CDC20, CDC25, CDC25A, CDC25B, CDC2L5, CDK10, CDK4, CDK5, CDK9, CDKL1, CDKN1A, CDKN1B, CDKN1C, CDKN2A, CDKN2B, CDKN2D, CEBPG, CENPC1, CGRRF1, CHAF1A, CIB1, CKMT1, CLK1, CLK2, CLK3, CLNS1A, CLTC, COL1A1, COL6A3, COX6C, COX7A2, CRAT, CRHR1, CSF1R, CSK, CSNK1G2, CTNNA1, CTNNB1, CTPS, CTSC, CTSD, CUL1, CYR61, DCC, DCN, DDX10, DEK, DHCR7, DHRS2, DHX8, DLG3, DVL1, DVL3, E2F1, E2F3, E2F5, EGFR, EGR1, EIF5, EPHA2, ERBB2, ERBB3, ERBB4, ERCC3, ETV1, ETV3, ETV6, F2R, FASTK, FBN1, FBN2, FES, FGFR1, FGR, FKBP8, FN1, FOS, FOSL1, FOSL2, FOXG1A, FOXO1A, FRAP1, FRZB, FTL, FZD2, FZD5, FZD9, G22P1, GAS6, GCN5L2, GDF15, GNA13, GNAS, GNB2, GNB2L1, GPR39, GRB2, GSK3A, GSPT1, GTF2I, HDAC1, HDGF, HMMR, HPRT1, HRB, HSPA4, HSPA5, HSPA8, HSPB1, HSPH1, HYAL1, HYOU1, ICAM1, ID1, ID2, IDUA, IER3, IFITM1, IGF1R, IGF2R, IGFBP3, IGFBP4, IGFBP5, IL1B, ILK, ING1, IRF3, ITGA3, ITGA6, ITGB4, JAK1, JARID1A, JUN, JUNB, JUND, K-ALPHA-1, KIT, KITLG, KLK10, KPNA2, KRAS2, KRT18, KRT2A, KRT9, LAMB1, LAMP2, LCK, LCN2, LEP, LITAF, LRPAP1, LTF, LYN, LZTR1, MADH1, MAP2K2, MAP3K8, MAPK12, MAPK13, MAPKAPK3, MAPRE1, MARS, MAS1, MCC, MCM2, MCM4, MDM2, MDM4, MET, MGST1, MICB, MLLT3, MME, MMP1, MMP14, MMP17, MMP2, MNDA, MSH2, MSH6, MT3, MYB, MYBL1, MYBL2, MYC, MYCL1, MYCN, MYD88, MYL9, MYLK, NEO1, NF1, NF2, NFKB1, NFKB2, NFSF7, NID, NINJ1, NMBR, NME1, NME2, NME3, NOTCH1, NOTCH2, NOTCH4, NPM1, NQO1, NR1D1, NR2F1, NR2F6, NRAS, NRG1, NSEP1, OSM, PA2G4, PABPC1, PCNA, PCTK1, PCTK2, PCTK3, PDGFA, PDGFB, PDGFRA, PDPK1, PEA15, PFDN4, PFDN5, PGAM1, PHB, PIK3CA, PIK3CB, PIK3CG, PIM1, PKM2, PKMYT1, PLK2, PPARD, PPARG, PPIH, PPP1CA, PPP2R5A, PRDX2, PRDX4, PRKAR1A, PRKCBP1, PRNP, PRSS15, PSMA1, PTCH, PTEN, PTGS1, PTMA, PTN, PTPRN, RAB5A, RAC1, RAD50, RAF1, RALBP1, RAP1A, RARA, RARB, RASGRF1, RB1, RBBP4, RBL2, REA, REL, RELA, RELB, RET, RFC2, RGS19, RHOA, RHOB, RHOC, RHOD, RIPK1, RPN2, RPS6KB1, RRM1, SARS, SELENBP1, SEMA3C, SEMA4D, SEPP1, SERPINH1, SFN, SFPQ, SFRS7, SHB, SHH, SIAH2, SIVA, SIVA TP53, SKI, SKIL, SLC16A1, SLC1A4, SLC20A1, SMO, SMPD1, SNAI2, SND1, SNRPB2, SOCS1, SOCS3, SOD1, SORT1, SPINT2, SPRY2, SRC, SRPX, STAT1, STAT2, STAT3, STAT5B, STC1, TAF1, TBL3, TBRG4, TCF1, TCF7L2, TFAP2C, TFDP1, TFDP2, TGFA, TGFB1, TGFBI, TGFBR2, TGFBR3, THBS1, TIE, TIMP1, TIMP3, TJP1, TK1, TLE1, TNF, TNFRSF10A, TNFRSF10B, TNFRSF1A, TNFRSF1B, TNFRSF6, TNFSF7, TNK1, TOB1, TP53, TP53BP2, TP53I3, TP73, TPBG, TPT1, TRADD, TRAM1, TRRAP, TSG101, TUFM, TXNRD1, TYRO3, UBC, UBE2L6, UCHL1, USP7, VDAC1, VEGF, VHL, VIL2, WEE1, WNT1, WNT2, WNT2B, WNT3, WNT5A, WT1, XRCC1, YES1, YWHAB, YWHAZ, ZAP70, and ZNF9.

In some embodiments, the instant disclosure relates to a heterologous nucleic acid insert encoding a gene product associated with a CNS-related disorder. The following is a non-limiting list of genes associated with a CNS-related disorder: DRD2, GRIA1, GRIA2, GRIN1, SLC1A1, SYP, SYT1, CHRNA7, 3Rtau/4rTUS, APP, BAX, BCL-2, GRIK1, GFAP, IL-1, AGER, associated with Alzheimer's Disease; UCH-L1, SKP1, EGLN1, Nurr-1, BDNF, TrkB, gstm1, S106β, associated with Parkinson's Disease; IT15, PRNP, JPH3, TBP, ATXN1, ATXN2, ATXN3, Atrophin 1, FTL, TITF-1, associated with Huntington's Disease; FXN, associated with Freidrich's ataxia; ASPA, associated with Canavan's Disease; DMD, associated with muscular dystrophy; and SMN1, UBE1, DYNC1H1 associated with spinal muscular atrophy.

A heterologous nucleic acid insert may comprise as a transgene, a nucleic acid encoding a protein or functional RNA that modulates apoptosis. The following is a non-limiting list of genes associated with apoptosis and nucleic acids encoding the products of these genes and their homologues and encoding small interfering nucleic acids (e.g., shRNAs, miRNAs) that inhibit the expression of these genes and their homologues are useful as transgenes in certain embodiments of the disclosure: RPS27A, ABL1, AKT1, APAF1, BAD, BAG1, BAG3, BAG4, BAK1, BAX, BCL10, BCL2, BCL2A1, BCL2L1, BCL2L10, BCL2L11, BCL2L12, BCL2L13, BCL2L2, BCLAF1, BFAR, BID, BIK, NAIP, BIRC2, BIRC3, XIAP, BRCS, BIRC6, BIRC7, BIRC8, BNIP1, BNIP2, BNIP3, BNIP3L, BOK, BRAF, CARD10, CARD11, NLRC4, CARD14, NOD2, NOD1, CARD6, CARDS, CARDS, CASP1, CASP10, CASP14, CASP2, CASP3, CASP4, CASP5, CASP6, CASP7, CASP8, CASP9, CFLAR, CIDEA, CIDEB, CRADD, DAPK1, DAPK2, DFFA, DFFB, FADD, GADD45A, GDNF, HRK, IGF1R, LTA, LTBR, MCL1, NOL3, PYCARD, RIPK1, RIPK2, TNF, TNFRSF10A, TNFRSF10B, TNFRSF10C, TNFRSF10D, TNFRSF11B, TNFRSF12A, TNFRSF14, TNFRSF19, TNFRSF1A, TNFRSF1B, TNFRSF21, TNFRSF25, CD40, FAS, TNFRSF6B, CD27, TNFRSF9, TNFSF10, TNFSF14, TNFSF18, CD40LG, FASLG, CD70, TNFSF8, TNFSF9, TP53, TP53BP2, TP73, TP63, TRADD, TRAF1, TRAF2, TRAF3, TRAF4, TRAF5 DRD2, GRIA1, GRIA2, GRIN1, SLC1A1, SYP, SYT1, CHRNA7, 3Rtau/4rTUS, APP, BAX, BCL-2, GRIK1, GFAP, IL-1, AGER, UCH-L1, SKP1, EGLN1, Nurr-1, BDNF, TrkB, gstm1, S106β, IT15, PRNP, JPH3, TBP, ATXN1, ATXN2, ATXN3, Atrophin 1, FTL, TITF-1, FXN, ASPA, DMD, and SMN1, UBE1, DYNC1H1.

The skilled artisan will also realize that in the case of transgenes encoding proteins or polypeptides, that mutations that results in conservative amino acid substitutions may be made in a transgene to provide functionally equivalent variants, or homologs of a protein or polypeptide. In some aspects the disclosure embraces sequence alterations that result in conservative amino acid substitution of a transgene. In some embodiments, the transgene comprises a gene having a dominant negative mutation. For example, a transgene may express a mutant protein that interacts with the same elements as a wild-type protein, and thereby blocks some aspect of the function of the wild-type protein.

Useful transgene products also include miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The following non-limiting list of miRNA genes, and their homologues, are useful as transgenes or as targets for small interfering nucleic acids encoded by transgenes (e.g., miRNA sponges, antisense oligonucleotides, TuD RNAs) in certain embodiments of the methods: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-7i, hsa-let-7i*, hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133a*, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a*, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-29b-1*, hsa-miR-29b-2*, hsa-miR-29c, hsa-miR-29c*, hsa-miR-300, hsa-miR-301a, hsa-miR-301b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsamiR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*, hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsa-miR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-548b-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548i, hsa-miR-548j, hsa-miR-548k, hsa-miR-548l, hsa-miR-548m, hsa-miR-548n, hsa-miR-548o, hsa-miR-548p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*.

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, an small interfering nucleic acid that is substantially complementary to a miRNA is one that is capable of hybridizing with a miRNA, and blocking the miRNA's activity. In some embodiments, an small interfering nucleic acid that is substantially complementary to a miRNA is an small interfering nucleic acid that is complementary with the miRNA at all but 1, 2, 3, 4, 5, 6, 7, 8, 9, 10, 11, 12, 13, 14, 15, 16, 17, or 18 bases. In some embodiments, an small interfering nucleic acid sequence that is substantially complementary to a miRNA, is an small interfering nucleic acid sequence that is complementary with the miRNA at, at least, one base.

A "miRNA Inhibitor" is an agent that blocks miRNA function, expression and/or processing. For instance, these molecules include but are not limited to microRNA specific antisense, microRNA sponges, tough decoy RNAs (TuD RNAs) and microRNA oligonucleotides (double-stranded, hairpin, short oligonucleotides) that inhibit miRNA interaction with a Drosha complex. MicroRNA inhibitors can be expressed in cells from a transgenes of a nucleic acid, as discussed above. MicroRNA sponges specifically inhibit miRNAs through a complementary heptameric seed sequence (Ebert, M. S. Nature Methods, Epub Aug. 12, 2007;). In some embodiments, an entire family of miRNAs can be silenced using a single sponge sequence. TuD RNAs achieve efficient and long-term-suppression of specific miRNAs in mammalian cells (See, e.g., Takeshi Haraguchi, et al., Nucleic Acids Research, 2009, Vol. 37, No. 6 e43, the contents of which relating to TuD RNAs are incorporated herein by reference). Other methods for silencing miRNA function (derepression of miRNA targets) in cells will be apparent to one of ordinary skill in the art.

In some aspects, nucleic acids described herein (e.g., ceDNA) may be useful for the treatment of CNS-related disorders. As used herein, a "CNS-related disorder" is a disease or condition of the central nervous system. A CNS-related disorder may affect the spinal cord (e.g., a myelopathy), brain (e.g., a encephalopathy) or tissues surrounding the brain and spinal cord. A CNS-related disorder may be of a genetic origin, either inherited or acquired through a somatic mutation. A CNS-related disorder may be a psychological condition or disorder, e.g., Attention Deficit Hyperactivity Disorder, Autism Spectrum Disorder, Mood Disorder, Schizophrenia, Depression, Rhett Syndrome, etc. A CNS-related disorder may be an autoimmune disorder. A CNS-related disorder may also be a cancer of the CNS, e.g., brain cancer. A CNS-related disorder that is a cancer may be a primary cancer of the CNS, e.g., an astrocytoma, glioblastomas, etc., or may be a cancer that has metastasized to CNS tissue, e.g., a lung cancer that has metastasized to the brain. Further non-limiting examples of CNS-related disorders, include Parkinson's Disease, Lysosomal Storage Disease, Ischemia, Neuropathic Pain, Amyotrophic lateral sclerosis (ALS), Multiple Sclerosis (MS), and Canavan disease (CD).

In some embodiments, nucleic acids (e.g., ceDNA) described herein may be useful for delivering gene therapy to cardiac cells (e.g., heart tissue). Accordingly, in some embodiments, nucleic acids (e.g., ceDNA) described herein may be useful for the treatment of cardiovascular disorders. As used herein, a "cardiovascular disorder" is a disease or condition of the cardiovascular system. A cardiovascular disease may affect the heart, circulatory system, arteries, veins, blood vessels and/or capillaries. A cardiovascular disorder may be of a genetic origin, either inherited or acquired through a somatic mutation. Non-limiting examples of cardiovascular disorders include rheumatic heart disease, valvular heart disease, hypertensive heart disease, aneurysm, atherosclerosis, hypertension (e.g., high blood pressure), peripheral arterial disease (PAD), ischemic heart disease, angina, coronary heart disease, coronary artery disease, myocardial infarction, cerebral vascular disease, transient ischemic attack, inflammatory heart disease, cardiomyopathy, pericardial disease, congenital heart disease, heart failure, stroke, and myocarditis due to Chagas disease.

In some embodiments, nucleic acids described herein (e.g., ceDNA) may target the lung and/or tissue of the pulmonary system. Accordingly, in some embodiments, nucleic acids (e.g., ceDNA) described herein may be useful for treatment of pulmonary disease. As used herein a "pulmonary disease" is a disease or condition of the pulmonary system. A pulmonary disease may affect the lungs or muscles involved in breathing. A pulmonary disease may be of a genetic origin, either inherited or acquired through a somatic mutation. A pulmonary disease may be a cancer of the lung, including but not limited to, non-small cell lung cancer, small cell lung cancer, and lung carcinoid tumor. Further non-limiting examples of pulmonary diseases include acute bronchitis, acute respiratory distress syndrome (ARDS), asbestosis, asthma, bronchiectasis, bronchiolitis, bronchiolitis obliterans organizing pneumonia (BOOP), bronchopulmonary dysplasia, byssinosis, chronic bronchitis, coccidioidomycosis (Cocci), chronic obstructive pulmonary disorder (COPD), cryptogenic organizing pneumonia (COP), cystic fibrosis, emphysema, Hantavirus Pulmonary Syndrome, histoplasmosis, Human Metapneumovirus, hypersensitivity pneumonitis, influenza, lymphangiomatosis, mesothelioma, Middle Eastern Respiratory Syndrome, non-tuberculosis *Mycobacterium*, Pertussis, Pneumoconiosis (Black Lung Disease), pneumonia, primary ciliary dyskinesia, primary pulmonary hypertension, pulmonary arterial hypertension, pulmonary fibrosis, pulmonary vascular disease, Respiratory Syncytial Virus (RSV), sarcoidosis, Severe Acute Respiratory Syndrome (SARS), silicosis, sleep apnea, Sudden Infant Death Syndrome (SIDS), and tuberculosis.

In some embodiments, nucleic acids described herein (e.g., ceDNA) may target liver tissue. Accordingly, in some embodiments, nucleic acids described herein (e.g., ceDNA) may be useful for treatment of hepatic disease. As used herein a "hepatic disease" is a disease or condition of the liver. A hepatic disease may be of a genetic origin, either inherited or acquired through a somatic mutation. A hepatic disease may be a cancer of the liver, including but not limited to hepatocellular carcinoma (HCC), fibrolamellar carcinoma, cholangiocarcinoma, angiosarcoma and hepatoblastoma. Further non-limiting examples of pulmonary diseases include Alagille Syndrome, Alpha 1 Anti-Trypsin Deficiency, autoimmune hepatitis, biliary atresia, cirrhosis, cystic disease of the liver, fatty liver disease, galactosemia, gallstones, Gilbert's Syndrome, hemochromatosis, liver disease in pregnancy, neonatal hepatitis, primary biliary cirrhosis, primary sclerosing cholangitis, porphyria, Reye's Syndrome, sarcoidosis, toxic hepatitis, Type 1 Glycogen Storage Disease, tyrosinemia, viral hepatitis A, B, C, Wilson Disease, and schistosomiasis.

In some embodiments, nucleic acids described herein (e.g., ceDNA) may target kidney tissue. Accordingly, in some embodiments, nucleic acids described herein (e.g., ceDNA) may be useful for treatment of kidney disease. As used herein a "kidney disease" is a disease or condition of the liver. A hepatic disease may be of a genetic origin, either inherited or acquired through a somatic mutation. A hepatic disease may be a cancer of the kidney, including but not limited to renal cell cancer, clear cell cancer, papillary cancer type 1, papillary cancer type 2, chromophobe cancer, oncocytic cell cancer, collecting duct cancer, transitional cell cancer of the renal pelvis and Wilm's tumor. Further non-limiting examples of kidney disease include Abderhalden-Kaufmann-Lignac syndrome (Nephropathic Cystinosis), Acute Kidney Failure/Acute Kidney Injury, Acute Lobar Nephronia, Acute Phosphate Nephropathy, Acute Tubular Necrosis, Adenine Phosphoribosyltransferase Deficiency, Adenovirus Nephritis, Alport Syndrome, Amyloidosis, Angiomyolipoma, Analgesic Nephropathy, Angiotensin Antibodies and Focal Segmental Glomerulosclerosis, Antiphospholipid Syndrome, Anti-TNF-α Therapy-related Glomerulonephritis, APOL1 Mutations, Apparent Mneralocorticoid Excess Syndrome, Aristolochic Acid Nephropathy, Balkan Endemic Nephropathy, Bartter Syndrome, Beeturia, β-Thalassemia Renal Disease, Bile Cast Nephropathy, BK Polyoma, C1q Nephropathy, Cardiorenal syndrome, CFHR5 nephropathy, Cholesterol Emboli, Churg-Strauss syndrome, Chyluria, Collapsing Glomerulopathy, Collapsing Glomerulopathy Related to CMV, Congenital Nephrotic Syndrome, Conorenal syndrome (Mainzer-Saldino Syndrome or Saldino-Mainzer Disease), Contrast Nephropathy, Copper Sulfate Intoxication, Cortical Necrosis, Cryogloβuinemia, Crystal-Induced Acute Kidney injury, Cystic Kidney Disease, Acquired, Cystinuria, Dense Deposit Disease (MPGN Type 2), Dent Disease (X-linked Recessive Nephrolithiasis), Dialysis Disequilibrium Syndrome, Diabetic Kidney Disease, Diabetes Insipidus, EAST syndrome, Ectopic Ureter, Edema, Erdheim-Chester Disease, Fabry's Disease, Familial Hypocalciuric Hypercalcemia, Fanconi Syndrome, Fraser syndrome, Fibronectin Glomerulopathy, Fibrillary Glomerulonephritis and Immunotactoid Glomerulopathy, Fraley syndrome, Focal Segmental Glomerulosclerosis, Focal Sclerosis, Focal Glomerulosclerosis, Galloway Mowat syndrome, Gitelman Syndrome, Glomerular Diseases, Glomerular Tubular Reflux, Glycosuria, Goodpasture Syndrome, Hemolytic Uremic Syndrome (HUS), Atypical Hemolytic Uremic Syndrome (aHUS), Hemophagocytic Syndrome, Hemorrhagic Cystitis, Hemosiderosis related to Paroxysmal Nocturnal Hemoglobinuria and Hemolytic Anemia, Hepatic Veno-Occlusive Disease, Sinusoidal Obstruction Syndrome, Hepatitis C-Associated Renal Disease, Hepatorenal Syndrome, HIV-Associated Nephropathy (HIVAN), Horseshoe Kidney (Renal Fusion), Hunner's Ulcer, Hyperaldosteronism, Hypercalcemia, Hyperkalemia, Hypermagnesemia, Hypernatremia, Hyperoxaluria, Hyperphosphatemia, Hypocalcemia, Hypokalemia, Hypokalemia-induced renal dysfunction, Hypomagnesemia, Hyponatremia, Hypophosphatemia, IgA Nephropathy, IgG4 Nephropathy, Interstitial Cystitis, Painful Bladder Syndrome, Interstitial Nephritis, Ivemark's syndrome, Kidney Stones, Nephrolithiasis, Leptospirosis Renal Disease, Light Chain Deposition Disease, Monoclonal Immunoglobulin Deposition Disease, Liddle Syndrome, Lightwood-Albright Syndrome, Lipoprotein Glomerulopathy, Lithium Nephrotoxicity, LMX1B Mutations Cause Hereditary FSGS, Loin Pain Hematuria, Lupus, Systemic Lupus Erythematosis, Lupus Kidney Disease, Lupus Nephritis, Lyme Disease-Associated Glomerulonephritis, Malarial Nephropathy, Malignant Hypertension, Malakoplakia, Meatal Stenosis, Medullary Cystic Kidney Disease, Medullary Sponge Kidney, Megaureter, Melamine Toxicity and the Kidney, Membranoproliferative Glomerulonephritis, Membranous Nephropathy, MesoAmerican Nephropathy, Metabolic Acidosis, Metabolic Alkalosis, Microscopic Polyangiitis, Milk-alkalai syndrome, Minimal Change Disease, Multicystic dysplastic kidney, Multiple Myeloma, Myeloproliferative Neoplasms and Glomerulopathy, Nail-patella Syndrome, Nephrocalcinosis, Nephrogenic Systemic Fibrosis, Nephroptosis (Floating Kidney, Renal Ptosis), Nephrotic Syndrome, Neurogenic Bladder, Nodular Glomerulosclerosis, Non-Gonococcal, Nutcracker syndrome, Orofaciodigital Syndrome, Orthostatic Hypotension, Orthostatic Proteinuria, Osmotic Diuresis, Page Kidney, Papillary Necrosis, Papillorenal Syndrome (Renal-Coloboma Syndrome, Isolated Renal Hypoplasia), The Peritoneal-Renal Syndrome, Posterior Urethral Valve, Post-infectious Glomerulonephritis, Post-streptococcal Glomerulonephritis, Polyarteritis Nodosa, Polycystic Kidney Disease, Posterior Urethral Valves, Preeclampsia, Proliferative Glomerulonephritis with Monoclonal IgG Deposits (Nasr Disease), Proteinuria (Protein in Urine), Pseudohyperaldosteronism, Pseudohypoparathyroidism, Pulmonary-Renal Syndrome, Pyelonephritis (Kidney Infection), Pyonephrosis, Radiation Nephropathy, Refeeding syndrome, Reflux Nephropathy, Rapidly Progressive Glomerulonephritis, Renal Abscess, Peripnephric Abscess, Renal Agenesis, Renal Artery Aneurysm, Renal Artery Stenosis, Renal Cell Cancer, Renal Cyst, Renal Hypouricemia with Exercise-induced Acute Renal Failure, Renal Infarction, Renal Osteodystrophy, Renal Tubular Acidosis, Reset Osmostat, Retrocaval Ureter, Retroperitoneal Fibrosis, Rhabdomyolysis, Rhabdomyolysis related to Bariatric Surgery, Rheumatoid Arthritis-Associated Renal Disease, Sarcoidosis Renal Disease, Salt Wasting, Renal and Cerebral, Schimke immuno-osseous dysplasia, Scleroderma Renal Crisis, Serpentine Fibula-Polycystic Kidney Syndrome, Exner Syndrome, Sickle Cell Nephropathy, Silica Exposure and Chronic Kidney Disease, Kidney Disease Following Hematopoietic Cell Transplantation, Kidney Disease Related to Stem Cell Transplantation, Thin Basement Membrane Disease, Benign Familial Hematuria, Trigonitis, Tuberous Sclerosis, Tubular Dysgenesis, Tumor Lysis Syndrome, Uremia, Uremic Optic Neuropathy, Ureterocele, Urethral Caruncle, Urethral Stricture, Urinary Incontinence, Urinary Tract Infection, Urinary Tract Obstruction, Vesicointestinal Fistula, Vesicoureteral Reflux, Von Hippel-Lindau Disease, Warfarin-Related Nephropathy, Wegener's Granulomatosis, Granulomatosis with Polyangiitis, and Wunderlich syndrome.

In some embodiments, nucleic acids described herein (e.g., ceDNA) may be useful for delivering gene therapy to ocular tissue. Accordingly, in some embodiments, nucleic acids described herein (e.g., ceDNA) may be useful for the treatment of ocular disorders. As used herein, an "ocular disorder" is a disease or condition of the eye. A cardiovascular disease may affect the eye, sclera, cornea, anterior chamber, posterior chamber, iris, pupil, lens, vitreous humor, retina, or optic nerve. An ocular disorder may be of a genetic origin, either inherited or acquired through a somatic mutation. Non-limiting examples of ocular diseases and disorders include but are not limited to: age-related macular degeneration, retinopathy, diabetic retinopathy, macula edema, glaucoma, retinitis pigmentosa, Stargardt's disease, Usher's disease and Leber's congenital amaurosis and eye cancer.

In some embodiments, nucleic acids described herein (e.g., ceDNA) may be useful for delivering gene therapy to blood tissue (e.g., blood cells). Accordingly, in some embodiments, nucleic acids described herein (e.g., ceDNA) may be useful for the treatment of blood disorders. As used herein, a "blood disorder" is a disease or condition of the blood. A blood disorder may be of a genetic origin, either inherited or acquired through a somatic mutation. Non-limiting examples of blood diseases and disorders include but are not limited to anemia (e.g., anemia in chronic kidney disease, aplastic anemia, myelodysplastic anemia, sickle cell anemia), deep vein thrombosis, hemophilia (e.g., hemophilia A, hemophilia B, hemophilia C), Henoch-Schönlein Purpura, pulmonary embolism, thalassemia, and Von Willebrand disease.

In some embodiments, nucleic acids described herein (e.g., ceDNA) may be useful for delivering gene editing molecules (e.g., nucleases) to a subject. In some embodiments a nucleic acid described by the disclosure comprises a heterologous nucleic acid insert encodes a nuclease. As used herein, the terms "endonuclease" and "nuclease" refer to an enzyme that cleaves a phosphodiester bond or bonds within a polynucleotide chain. Nucleases may be naturally occurring or genetically engineered. Genetically engineered nucleases are particularly useful for genome editing and are generally classified into four families: zinc finger nucleases (ZFNs), transcription activator-like effector nucleases (TALENs), engineered meganucleases and CRISPR-associated proteins (Cas nucleases). In some embodiments, the nuclease is a ZFN. In some embodiments, the ZFN comprises a FokI cleavage domain. In some embodiments, the ZFN comprises Cys2His2 fold group. In some embodiments, the nuclease is a TALEN. In some embodiments, the TALEN comprises a FokI cleavage domain. In some embodiments, the nuclease is an engineered meganuclease.

The term "CRISPR" refers to "clustered regularly interspaced short palindromic repeats", which are DNA loci containing short repetitions of base sequences. CRISPR loci form a portion of a prokaryotic adaptive immune system that confers resistance to foreign genetic material. Each CRISPR loci is flanked by short segments of "spacer DNA", which are derived from viral genomic material. In the Type II CRISPR system, spacer DNA hybridizes to transactivating RNA (tracrRNA) and is processed into CRISPR-RNA (crRNA) and subsequently associates with CRISPR-associated nucleases (Cas nucleases) to form complexes that recognize and degrade foreign DNA. In certain embodiments, the nuclease is a CRISPR-associated nuclease (Cas nuclease). Examples of CRISPR nucleases include, but are not limited to Cas9, Cas6 and dCas9. dCas9 is an engineered Cas protein that binds to a target locus but does not cleave said locus. In some embodiments, the nuclease is Cas9. In some embodiments, the Cas9 is derived from the bacteria *S. pyogenes* (SpCas9).

For the purpose of genome editing, the CRISPR system can be modified to combine the tracrRNA and crRNA in to a single guide RNA (sgRNA) or just (gRNA). As used herein, the term "guide RNA" or "gRNA" refers to a polynucleotide sequence that is complementary to a target sequence in a cell and associates with a Cas nuclease, thereby directing the Cas nuclease to the target sequence. In some embodiments, a nucleic acid described by the disclosure comprises a heterologous nucleic acid insert encoding a guide RNA (gRNA). In some embodiments, a gRNA ranges between 1 and 30 nucleotides in length. In some embodiments, a gRNA ranges between 5 and 25 nucleotides in length. In some embodiments, a gRNA ranges between 10 and 20 nucleotides in length. In some embodiments, a gRNA ranges between 14 and 18 nucleotides in length. In some embodiments, a nucleic acid described by the disclosure comprises a heterologous nucleic acid insert encoding a gRNA and a CRISPR nuclease.

In some aspects, the disclosure relates to a nucleic acid encoding a heterologous nucleic acid insert that does not encode a functional protein. For example, in the context of gene therapy, transgene promoter integration may cause oncogene activation. Accordingly, in some embodiments, the disclosure relates to a heterologous nucleic acid insert encoding a promoterless construct. Without wishing to be bound by any particular theory, a promoterless expression construct is useful, in some embodiments, as a substrate for gene editing.

As used herein, "genome editing" refers to adding, disrupting or changing genomic sequences (e.g., a gene sequence). In some embodiments, genome editing is performed using engineered proteins and related molecules. In some aspects, genome editing comprises the use of engineered nucleases to cleave a target genomic locus. In some embodiments, genome editing further comprises inserting, deleting, mutating or substituting nucleic acid residues at a cleaved locus. In some embodiments, inserting, deleting, mutating or substituting nucleic acid residues at a cleaved locus is accomplished through endogenous cellular mechanisms such as homologous recombination (HR) and non-homologous end joining (NHEJ). Exemplary genome editing technologies include, but are not limited to Transcription Activator-like Effector Nucleases (TALENs), Zinc Finger Nucleases (ZFNs), engineered meganuclease re-engineered homing endonucleases, the CRISPR/Cas system. In some embodiments, the gene editing technologies are proteins or molecules related to TALENs, including but not limited to transcription activator-like effectors (TALEs) and restriction endonucleases (e.g., FokI). In some embodiments, the gene editing technologies are proteins or molecules related to ZFNs, including but not limited to proteins comprising the Cys2His2 fold group (for example Zif268 (EGR1)), and restriction endonucleases (e.g., FokI). In some embodiments, the gene editing technologies are proteins or molecules related to the CRISPR/Cas system, including but not limited to Cas9, Cas6, dCas9, CRISPR RNA (crRNA) and trans-activating crRNA (tracrRNA). In some embodiments, the promoterless construct provides a substrate for TALENS, zinc finger nucleases (ZFNs), meganucleases, Cas9, and other gene editing proteins.

In some aspects, the disclosure relates to a nucleic acid encoding a heterologous nucleic acid insert that encodes a DNA vaccine. As used herein, "DNA vaccine" refers to a nucleic acid encoding an antigen that stimulates an immune response (e.g., a cellular immune response or a humoral immune response) against that antigen in a host. In some embodiments, the immune response is a protective response that protects against a future infection or condition. However, in some embodiments, the immune response treats (e.g., eradicates or attenuates) an existing infection or condition. Examples of DNA vaccines include HL chain Ig, scFv, single-domain Ig derived from camelidae (VhH) or cartilaginous fish (Vnar), nanobody, and other paratope recognitions peptides and fusion peptides collectively referred to as Ig (or Ig-like) molecules.

In some embodiments, a heterologous nucleic acid insert encodes an Ig or Ig-like molecule. In some embodiments, the Ig (or Ig-like) molecules are unmodified protein sequences derived from monoclonal antibody sequences. In some embodiments, the Ig (or Ig-like) molecules are unmodified protein sequences derived from murine or other mammalian monoclonal antibody sequences.

In some embodiments, the Ig (or Ig-like) molecules are unmodified protein sequences derived from synthetic randomly generated peptide libraries. In some embodiments, the libraries were derived from complimentary DNA obtained from naïve vertebrate species. The species include, but are not limited to mammals, such as primates (e.g., humans and non-human primates), rodents (e.g., mouse, rats), ungulates, camelids, equines, canines, felines, marsupials, and animals of agricultural interest; Avian species, including chickens, ducks, and geese; piscine species including cartlilaginous fish, lamprey eels, and jawed fish species.

In some embodiments, the heterologous nucleic acid encodes the heavy and light chains for an immunoglobulin (Ig), such that when administered to a permissive cell, an assembled Ig is secreted into the circulatory system. In some embodiments, the Ig molecule is not secreted and acts internally as a so-called "intra-body".

In some embodiments, a heterologous nucleic acid insert encodes an Ig molecule that is an engineered single-chain antibody consisting of the heavy and light chain variable regions in one polypeptide (scFv). The scFv retains avidity and specificity for the target antigen.

In some embodiments, a heterologous nucleic acid insert encodes an Ig molecule that binds to microbial agents and affects the infectivity of the microbe. In some embodiments, the microbial agents are prokaryotic organisms. In some embodiments, the microbial agents are rickettsia, mycoplasma, or other intracellular life forms.

In some embodiments, a heterologous nucleic acid insert encodes an Ig molecule that binds to viral structural protein(s) of human pathogenic viruses, including but not limited an Ebola virus viral protein, a human immune deficiency viral protein, a papilloma viral protein, a herpes simplex 1 viral protein, a herpes simplex 2 viral protein, a HCV A viral protein, a HCV B viral protein, a HCV C viral protein, a HCV non-A viral protein, a HCV non-B viral protein, or a dengue hemorrhagic fever viral protein. In some embodiments, a heterologous nucleic acid insert encodes an Ig molecule that binds to viral structural protein(s) of a zoonotic pathogen, including, but not limited to foot and mouth disease virus and rabies virus.

In some aspects, nucleic acids described by the disclosure are useful for the production of modified cells, such as ex vivo modified cells. As used herein, "ex vivo modified cell" refers to a cell (e.g., a mammalian cell) that is removed from a subject, genetically modified (e.g., transfected or transduced with exogenous nucleic acids, or genetically reprogrammed), cultured or expanded, and optionally, returned to a subject (e.g., either the same subject, or a different subject). Generally, ex vivo modified cells are useful for autologous cell therapy, or allogeneic cell therapy. For example, cells may be removed from a subject having a disease associated with a particular genetic defect (e.g., overexpression of a particular protein), transfected with a nucleic acid that corrects the genetic defect (e.g. reduces expression of the protein), and reintroduced into the subject. In another non-limiting example, cells are removed from a subject, genetically reprogrammed (e.g., dedifferentiated or transdifferentiated into stem cells), expanded, and reintroduced into the subject. In some embodiments, ex vivo modified cells produced by transfection with a nucleic acid as described by the disclosure have an improved safety profile compared to ex vivo cells produced by currently available gene therapy vectors.

In some aspects, nucleic acids described by the disclosure are useful for the production of chimeric antigen T-cells (CARTs). Chimeric Antigen Receptors (CARs) are engineered T cell receptors displaying specificity against target antigens based on a single chain FV (scFv) antibody moiety. Generally, CARTs are produced by transduction of T-cells with lentiviral vectors comprising DNA encoding CARs. Lentiviral transduction, in some embodiments, raises the risk of insertional mutagenesis leading to cancer. As described by the disclosure, nucleic acids having asymmetric interrupted self-complementary sequences exhibit reduced likelihood of insertional mutagenesis compared to other gene therapy modalities. Accordingly, in some embodiments a nucleic acid described by the disclosure comprises a heterologous nucleic acid insert (e.g., a transgene) encoding a CAR. In some embodiments, a CART produced by transduction with a nucleic acid described by the disclosure exhibits an improved safety profile compared to a CART produced by lentiviral transduction.

Additional Components

In addition to the major elements identified above for the nucleic acid, the nucleic acid also includes conventional control elements necessary which are operably linked to the heterologous nucleic acid insert (e.g., transgene) in a manner which permits its transcription, translation and/or expression in a cell transfected with a nucleic acid described by the disclosure. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

In some embodiments, a heterologous nucleic acid insert (e.g., transgene) comprises a protein coding sequence that is operably linked to one or more regulatory sequences. As used herein, a nucleic acid coding sequence and regulatory sequences are said to be "operably" linked when they are covalently linked in such a way as to place the expression or transcription of the nucleic acid sequence (e.g., transgene) under the influence or control of the regulatory sequences. If it is desired that the nucleic acid sequence (e.g., transgene) be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., gRNA).

For nucleic acids (e.g., transgenes) encoding proteins, a polyadenylation sequence generally is inserted following the transgene sequences and before the 3' AAV ITR sequence. A heterologous nucleic acid insert (e.g., transgene) useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al, and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the disclosure may optionally include 5' leader or signal sequences. The choice and design of an appropriate vector is within the ability and discretion of one of ordinary skill in the art.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al, Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (a-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

Production of Closed-Ended Linear Duplex DNA (ceDNA)

In some aspects, the disclosure provides a method of producing a nucleic acid as described by the disclosure (e.g., ceDNA), comprising: (i) introducing into a permissive cell a nucleic acid encoding a heterologous nucleic acid insert flanked by at least one interrupted self-complementary sequence, each self-complementary sequence having an operative terminal resolution site and a rolling circle replication protein binding element, wherein the self-complementary sequence is interrupted by a cross-arm sequence forming two opposing, lengthwise-symmetric stem-loops, each of the opposing lengthwise-symmetric stem-loops having a stem portion in the range of 5 to 15 base pairs in length and a loop portion having 2 to 5 unpaired deoxyribonucleotides; and, (ii) maintaining the permissive cell under conditions in which a rolling circle replication protein in the permissive cell initiates production of multiple copies of the nucleic acid.

The number of copies resulting from production of a nucleic acid can be expressed as a multiple of the original number of copies of the nucleic acid (e.g., 1, 2, 10, 100, or more original copies) introduced into the permissive cell. In some embodiments, production of multiple copies of the nucleic acid results in between 2-fold and 10,000-fold increase in the number of copies of the nucleic acid in the permissive cell. In some embodiments, production of multiple copies of the nucleic acid results in greater than 10,000-fold increase in the number of copies of the nucleic acid in the permissive cell.

In some aspects, the disclosure provides transfected cells (e.g., transfected permissive cells). The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable cells (e.g., permissive cells).

A "permissive cell" refers to any cell in which a nucleic acid as described by the disclosure replicates, or is capable of supporting replication of a nucleic acid as described by the disclosure. In some embodiments, the permissive cell does not express viral capsid proteins capable of packaging replicative copies of the nucleic acid into a viral particle. Aspects of the disclosure relate, in part, to the surprising discovery that, in some embodiments, mammalian cells are not permissive for replication of nucleic acids described by the disclosure. Accordingly, in some embodiments, a permissive cell is a non-mammalian cell (e.g., the permissive cell is not a mammalian cell). In some embodiments, the permissive cell is an insect cell line, yeast cell line, or bacterial cell line.

Examples of permissive insect cells include but are not limited to *Spodoptera frugiperda* (e.g., Sf9, Sf21), *Spodoptera exigua, Heliothis virescens, Helicoverpa zea, Heliothis subflexa, Anticarsia gemmatalis, Trichoplusia ni* (e.g., High-Five cells), *Drosophila melanogaster* (e.g., S2, S3), *Antheraea eucalypti, Bombyx mori, Aedes alpopictus, Aedes aegyptii*, and others.

Examples of permissive bacterial cells include, but are not limited to *Escherichia coli, Corynebacterium glutamicum*, and *Pseudomonas fluorescens*.

Examples of permissive yeast cells include but are not limited to *Saccharomyces cerevisiae, Saccharomyces pombe, Pichia pastoris, Bacillus* sp., *Aspergillus* sp., *Trichoderma* sp., and *Myceliophthora thermophila* C1.

Examples of permissive plant cells include but are not limited to *Nicotiana* sp., *Arabidopsis thaliana, Mays zea, Solanum* sp., or *Lemna* sp.

In some embodiments, a permissive cell is a mammalian cell. Examples of permissive mammalian cells include Henrietta Lacks tumor (HeLa) cells and baby hamster kidney (BHK-21) cells.

In some embodiments, a nucleic acid as described by the disclosure is contained within a vector and delivered to a permissive cell. As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter.

In some embodiments, the method comprises expressing a rolling circle replication protein (e.g., a viral nonstructural protein, such as an AAV Rep protein) in the permissive cell. In some embodiments more than one (e.g., 2, 3, 4, or more) rolling circle replication proteins are expressed in a permissive cell. Without wishing to be bound by any particular theory, viral nonstructural protein(s) expressed in the permissive cell mediate(s) replication of a nucleic acid described by the disclosure. For example, in some embodiments, AAV Rep78 and Rep52 are expressed in a permissive cell comprising a nucleic acid having AAV2 ITR-based asymmetric interrupted self-complementary sequences. In some embodiments, the nonstructural viral protein is selected from the group consisting of AAV78, AAV52, AAV Rep68, and AAV Rep 40.

In some embodiments a rolling circle replication protein (e.g., a viral nonstructural protein, such as an AAV Rep protein) expressed in a permissive cell is encoded by a helper virus vector. As used here, "helper virus vector" refers to a viral vector that expresses molecule(s) (e.g., one or more proteins) required for the replication of a nucleic acid as described by the disclosure. For example, in some embodiments a helper virus vector expresses one or more rolling circle replication proteins which bind to the RBE of an interrupted self-complementary nucleic acid sequence and initiate replication of the nucleic acid comprising the interrupted self-complementary nucleic acid sequence. Helper virus vectors are generally known and include, for example baculovirus, adenovirus, herpesvirus, cytomegalovirus, Epstein-Barr virus, and vaccinia virus vectors. In some embodiments, a helper virus vector is a baculovirus expression vector (BEV). Baculovirus expression vectors are generally known in the art, for example as disclosed in Passer et al. Methods Mol Biol. 2007; 388:55-76. Examples of baculovirus vectors include but are not limited to *Autograph californica* multiple nucleopolyhedrosis virus (AcMNPV) vector, BmNPV, and *Spodoptera exigua* multiple nucleopolyhedrovirus. In some embodiments, the helper virus vector is *Autograph californica* multiple nucleopolyhedrosis virus (AcMNPV) vector.

In some embodiments, methods of producing nucleic acids described by the disclosure further comprise a step of purifying the multiple copies of the nucleic acid from a cell (e.g., a permissive cell). Generally, any suitable nucleic acid purification method can be used. For example, in some embodiments, the multiple copies of the nucleic acid described by the disclosure are purified by plasmid purification kits, such as Qiagen MiniPrep kit, ethanol precipitation, phenol-chloroform purification, etc. However, the disclosure relates, in part, to the discovery that nucleic acids comprising interrupted self-complementary sequences exhibit poor binding efficiency to weak cation exchange chromatography media (e.g., diethylaminoethyl media, DEAE) and that purification using silica gel media produce well-resolved molecular species while reducing the formation of high molecular weight complexes. Thus, in some embodiments, the purification comprises contacting the nucleic acid with a silica gel resin.

In some embodiments, nucleic acids provided herein may be used to deliver a heterologous insert to a cell, e.g., for therapeutic purposes. Furthermore, in some aspects, the disclosure relates to the delivery of nucleic acids containing heterologous inserts that encoded therapeutic products (e.g., therapeutic proteins, therapeutic RNAs) to a subject. In order to avoid administration of impure or contaminated nucleic acids or to otherwise characterize the extent or purity, quality or make up of a nucleic acid preparation, such preparations may be subject to a quality control (QC) or other analysis procedure prior to use, e.g., prior to administration to a cell or subject. For example, methods of analyzing a nucleic acid, in some embodiments, comprise obtaining a nucleic acid preparation described by the disclosure and determining a physiochemical property of one or more nucleic acid components in the preparation, e.g., nucleic acid replication products.

Examples of physiochemical properties that may be determined include but are not limited to solubility, stability, structure (e.g., primary structure, secondary structure, tertiary structure, quaternary structure, etc.), hydrophobicity, GC content, molecular weight (e.g., molecular weight of one or more fragments or portions of a nucleic acid, for example following restriction digest), etc. In some embodiments, the physiochemical property is the nucleotide sequence of one or each self-complementary sequence (e.g., determining if a nucleic acid described by the disclosure comprises a truncated cross-arm sequence).

In some embodiments, the physiochemical property is the extent of multimerization (e.g., monomer, dimer, trimer, 4-mer, or other multimer or concatamer) of a nucleic acid as described by the disclosure. In some embodiments, the physiochemical property is the stoichiometry of monomeric and/or multimeric forms of the replication product in the nucleic acid preparation.

In some embodiments, the physiochemical property is the susceptibility of one or more replication products (e.g., obtained from a nucleic acid preparation) to digestion with a restriction endonuclease. For example, in some embodiments, a nucleic acid as described by the disclosure is digested with one or more restriction enzymes and the fragments of the nucleic acid are analyzed to determine the size of each fragment. Thus, in some embodiments, the physiochemical property is the molecular weight of one or more replication products or of a fragment of a replication product. In some embodiments, the molecular weight is of a fragment of the one or more replication products that comprises one or more self-complementary sequences. In some embodiments, the molecular weight is determined based on electrophoretic mobility. In some embodiments, the molecular weight is determined based on mass spectroscopy.

In some embodiments, the molecular weight is of a fragment of the one or more replication products. In some embodiments, the molecular weight is of fragment of a replication product that is amplified by a reaction comprising primer extension by a polymerase. Examples of polymerase-based extension methods include but are not limited to polymerase chain reaction (PCR), recombinase polymerase amplification, loop mediated isothermal amplification (LAMP), etc.

In some embodiments, the physiochemical property is the polarity of monomers in a dimeric form of the replication product, wherein the polarity is head-to-head, head-to-tail or tail-to-tail.

Generally, suitable assays for determining physiochemical properties may be used. Suitable assays may include restriction digestion analysis, gel electrophoresis (e.g., native gel electrophoresis, denaturing gel electrophoresis, high resolution gel electrophoresis), spectrometry (e.g., mass spectrometry, such as LC/MS, HPLC/MS, ESI-MS, MALDI-TOF, etc.), and nucleic acid sequencing (e.g., Maxam-Gilbert sequencing, pyrosequencing, chain-termination sequencing, massively parallel signature sequencing, single-molecule sequencing, nanopore sequencing, Illumina sequencing, etc.).

Compositions

In some aspects, the disclosure relates to compositions comprising a nucleic acid as described by the disclosure. In some embodiments, compositions comprising nucleic acids as described herein are delivered to a subject in need thereof. The nucleic acids may be delivered to a subject in compositions according to any appropriate methods known in the art. It should be appreciated that compositions may comprise one or more (e.g., a plurality) of nucleic acids as described by the disclosure. In some embodiments, a plurality of nucleic acids is 2, 3, 4, 5, 6, 7, 8, 9, 10, or more nucleic acids. In some embodiments, each of the one or more nucleic acids of a plurality is covalently linked (e.g., linked end-to-end). In some embodiments, the composition further comprises a pharmaceutically acceptable carrier.

The nucleic acid, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of the nucleic acids (e.g., ceDNA) to a mammalian subject may be by, for example, intramuscular injection or by administration into the bloodstream of the mammalian subject. Administration into the bloodstream may be by injection into a vein, an artery, or any other vascular conduit. In some embodiments, the nucleic acids are administered into the bloodstream by way of isolated limb perfusion, a technique well known in the surgical arts, the method essentially enabling the artisan to isolate a limb from the systemic circulation prior to administration of the nucleic acid. A variant of the isolated limb perfusion technique, described in U.S. Pat. No. 6,177,403, can also be employed by the skilled artisan to administer the nucleic acid(s) into the vasculature of an isolated limb to potentially enhance transfection of muscle cells or tissue. Moreover, in certain instances, it may be desirable to deliver the nucleic acid(s) to the CNS of a subject. By "CNS" is meant all cells and tissue of the brain and spinal cord of a vertebrate. Thus, the term includes, but is not limited to, neuronal cells, glial cells, astrocytes, cereobrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

Suitable carriers may be readily selected by one of skill in the art in view of the indication for which the nucleic acid(s) is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the nucleic acid(s) and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The nucleic acid(s) are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), oral, inhalation (including intranasal and intratracheal delivery), intraocular, intravenous, intramuscular, subcutaneous, intradermal, intratumoral, and other parental routes of administration. Routes of administration may be combined, if desired.

The dose of nucleic acid(s) required to achieve a particular "therapeutic effect," will vary based on several factors including, but not limited to: the route of nucleic acid administration, the level of gene or RNA expression required to achieve a therapeutic effect, the specific disease or disorder being treated, and the stability of the gene or RNA product. One of skill in the art can readily determine a nucleic acid dose range to treat a patient having a particular disease or disorder based on the aforementioned factors, as well as other factors that are well known in the art.

Dosage regime may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver the nucleic acid-based therapeutic constructs in suitably formulated pharmaceutical compositions disclosed herein either subcutaneously, intraopancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver nucleic acids. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the nucleic acid in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The nucleic acid compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the nucleic acids may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 ANG, containing an aqueous solution in the core.

In some embodiments, a liposome comprises cationic lipids. The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In some embodiments, cationic lipids include saturated and unsaturated alkyl and alicyclic ethers and esters of amines, amides, or derivatives thereof. In some embodiments, cationic lipids comprise straight-chain, branched alkyl, alkenyl groups, or any combination of the foregoing. In some embodiments, cationic lipids contain from 1 to about 25 carbon atoms (e.g., 1, 2, 3, 4, 5, 6, 7, 8, 9, 10, 11, 12, 13, 14, 15, 16, 17, 18, 19, 20, 21, 22, 23, 24, or 25 carbon atoms. In some embodiments, cationic lipids contain more than 25 carbon atoms. In some embodiments, straight chain or branched alkyl or alkene groups have six or more carbon atoms. A cationic lipid may also comprise, in some embodiments, one or more alicyclic groups. Non-limiting examples of alicyclic groups include cholesterol and other steroid groups. In some embodiments, cationic lipids are prepared with a one or more counterions. Examples of counterions (anions) include but are not limited to $Cl^-$, $Br^-$, $I^-$, $F^-$, acetate, trifluoroacetate, sulfate, nitrite, and nitrate.

Non-limiting examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPO-FECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N-(N′,N′-dimethylaminoethane)carbamoyl]cholesterol (DC-Chol), 2,3,-dioleyloxy-N-[2(sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). Nucleic acids (e.g., ceDNA) can also be complexed with, e.g., poly (L-lysine) or avidin and lipids may, or may not, be included in this mixture, e.g., steryl-poly (L-lysine).

In some embodiments, a nucleic acid described by the disclosure is delivered using a cationic lipid described in U.S. Pat. No. 8,158,601, or a polyamine compound or lipid as described in U.S. Pat. No. 8,034,376, the contents of each of which are incorporated herein by reference.

In some embodiments, a nucleic acid described by the disclosure is conjugated (e.g., covalently bound to an agent that increases cellular uptake. An "agent that increases cellular uptake" is a molecule that facilitates transport of a nucleic acid across a lipid membrane. For example, a nucleic acid may be conjugated to a lipophilic compound (e.g., cholesterol, tocopherol, etc.), a cell penetrating peptide (CPP) (e.g., penetratin, TAT, Syn1B, etc.), and polyamines (e.g., spermine). Further examples of agents that increase cellular uptake are disclosed, for example, in Winkler (2013). *Oligonucleotide conjugates for therapeutic applications*. Ther. Deliv. 4(7); 791-809, the contents of which are incorporated herein by reference.

In some embodiments, a nucleic acid described by the disclosure is conjugated to a polymer (e.g., a polymeric molecule) or a folate molecule (e.g., folic acid molecule). Generally, delivery of nucleic acids conjugated to polymers is known in the art, for example as described in WO2000/34343 and WO2008/022309, the contents of which are incorporated herein by reference. In some embodiments, a nucleic acid described by the disclosure is conjugated to a poly(amide) polymer, for example as described by U.S. Pat. No. 8,987,377. In some embodiments, a nucleic acid described by the disclosure is conjugated to a folic acid molecule as described in U.S. Pat. No. 8,507,455, the contents of which are incorporated herein by reference.

In some embodiments, a nucleic acid described by the disclosure is conjugated to a carbohydrate, for example as described in U.S. Pat. No. 8,450,467, the contents of which are incorporated herein by reference.

Alternatively, nanocapsule formulations of the nucleic acid may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

In some embodiments, a nucleic acid described by the disclosure is delivered by a lipid nanoparticle. Generally, lipid nanoparticles comprise an ionizable amino lipid (e.g., heptatriaconta-6,9,28,31-tetraen-19-yl 4-(dimethylamino) butanoate, DLin-MC3-DMA, a phosphatidylcholine (1,2-distearoyl-sn-glycero-3-phosphocholine, DSPC), cholesterol and a coat lipid (polyethylene glycol-dimyristolglycerol, PEG-DMG), for example as disclosed by Tam et al. (2013). *Advances in Lipid Nanoparticles for siRNA delivery*. Pharmaceuticals 5(3): 498-507. In some embodiments, a lipid nanoparticle has a mean diameter between about 10 and about 1000 nm. In some embodiments, a lipid nanoparticle has a diameter that is less than 300 nm. In some embodiments, a lipid nanoparticle has a diameter between about 10 and about 300 nm. In some embodiments, a lipid nanoparticle has a diameter that is less than 200 nm. In some embodiments, a lipid nanoparticle has a diameter between about 25 and about 200 nm. In some embodiments, a lipid nanoparticle preparation (e.g., composition comprising a plurality of lipid nanoparticles) has a size distribution in which the mean size (e.g., diameter) is about 70 nm to about 200 nm, and more typically the mean size is about 100 nm or less.

In some embodiments, a nucleic acid described by the disclosure is delivered by a gold nanoparticle. Generally, a nucleic acid can be covalently bound to a gold nanoparticle or non-covalently bound to a gold nanoparticle (e.g., bound by a charge-charge interaction), for example as described by Ding et al. (2014). *Gold Nanoparticles for Nucleic Acid Delivery*. Mol. Ther. 22(6); 1075-1083. In some embodiments, gold nanoparticle-nucleic acid conjugates are produced using methods described, for example, in U.S. Pat. No. 6,812,334, the contents of which are incorporated herein by reference.

In addition to the methods of delivery described above, the following techniques are also contemplated as alternative methods of delivering the nucleic acid compositions to a host. Sonophoresis (e.g., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Delivery/Administration

In some embodiments, the disclosure provides a method of delivering a heterologous nucleic acid to a cell (e.g., a host cell), the method comprising delivering to the cell a nucleic acid as described by the disclosure.

In some aspects, the disclosure provides transfected host cells. A "host cell" refers to any cell that harbors, or is capable of harboring, a substance of interest. A host cell may be used as a recipient of a nucleic acid as described by the disclosure. The term includes the progeny of the original cell which has been transfected. Thus, a "host cell" as used herein may refer to a cell which has been transfected with an exogenous DNA sequence (e.g., a nucleic acid as described by the disclosure). It is understood that the progeny of a single parental cell may not necessarily be completely identical in morphology or in genomic or total DNA complement as the original parent, due to natural, accidental, or deliberate mutation.

In some embodiments, a host cell is a permissive cell. In some embodiments, a host cell is not a permissive cell. Often a host cell is a mammalian cell. In some aspects, the disclosure provides a method of delivering a heterologous nucleic acid to a subject comprising administering a host cell having a nucleic acid as described by the disclosure to the subject. For example, in some embodiments, a host cell is a blood cell, such as a human blood cell, comprising a nucleic acid as described by the disclosure (e.g., a nucleic acid having a heterologous nucleic acid insert encoding a blood disease-associated transgene). Without wishing to be bound by any particular theory, delivery of such a host cell is useful, in some embodiments, for treatment of a disease or disorder of the blood.

Aspects of the disclosure relate to the discovery that nucleic acids as described herein elicit a reduced immune response (e.g., do not elicit an immune response) in a host relative to currently used viral and bacterially-derived gene therapy vectors. In some aspects, the disclosure provides a method of delivering a heterologous nucleic acid to a subject, the method comprising delivering to the subject a nucleic acid as described by the disclosure, wherein the delivery of the nucleic acid does not result in an immune response against the nucleic acid in the subject. In some embodiments, the immune response is a humoral response. Humoral immune response refers to production of antigen-specific antibodies by B lymphocytes. In some embodiments, the immune response is a cellular response. A cellular immune response refers to an immune response that does not involve antibodies but rather activation of immune cells (e.g., phagocytes, antigen-specific T-cells, macrophages, natural killer cells, etc.) by an antigen (e.g., an exogenous nucleic acid).

Without wishing to be bound by any particular theory, the lack of immune response elicited by administration of nucleic acids as described by the disclosure allows the nucleic acids to be administered to a host on multiple occasions. In some embodiments, the number of occasions in which a heterologous nucleic acid is delivered to a subject is in a range of 2 to 10 times (e.g., 2, 3, 4, 5, 6, 7, 8, 9, or 10 times). In some embodiments, a heterologous nucleic acid is delivered to a subject more than 10 times.

In some embodiments, a dose of nucleic acid (e.g., ceDNA) is administered to a subject no more than once per calendar day (e.g., a 24-hour period). In some embodiments, a dose of nucleic acid (e.g., ceDNA) is administered to a subject no more than once per 2, 3, 4, 5, 6, or 7 calendar days. In some embodiments, a dose of nucleic acid (e.g., ceDNA) is administered to a subject no more than once per calendar week (e.g., 7 calendar days). In some embodiments, a dose of nucleic acid (e.g., ceDNA) is administered to a subject no more than bi-weekly (e.g., once in a two calendar week period). In some embodiments, a dose of nucleic acid (e.g., ceDNA) is administered to a subject no more than once per calendar month (e.g., once in 30 calendar days). In some embodiments, a dose of nucleic acid (e.g., ceDNA) is administered to a subject no more than once per six calendar months. In some embodiments, a dose of nucleic acid (e.g., ceDNA) is administered to a subject no more than once per calendar year (e.g., 365 days or 366 days in a leap year).

As disclosed herein nucleic acids (including DNA expression constructs that may be used to express them) may be administered by any suitable route. For use in therapy, an effective amount of the nucleic acid (e.g., oligonucleotide) and/or other therapeutic agent can be administered to a subject by any mode that delivers the agent to the desired tissue, e.g., muscle tissue. In some embodiments, agents (e.g., nucleic acids) are administered intramuscularly. Other suitable routes of administration include but are not limited to oral, parenteral, intravenous, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the agents can be formulated readily by combining the active compound(s) with pharmaceutically acceptable carriers well known in the art. Such carriers enable the agents of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally oral formulations may also be formulated in saline or buffers for neutralizing internal acid conditions or may be administered without any carriers.

Pharmaceutical preparations that can be used orally include push fit capsules made of gelatin, as well as soft, sealed capsules made of gelatin and a plasticizer, such as glycerol or sorbitol. The push fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. Formulations for oral administration are typically in dosages suitable for such administration.

For buccal administration, the compositions may take the form of tablets or lozenges formulated in conventional manner.

For administration by inhalation, agents (e.g., nucleic acids) for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The agents (e.g., nucleic acids), when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of agents (e.g., antisense nucleic acids) in water-soluble form. Additionally, suspensions of agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the agents to allow for the preparation of highly concentrated solutions. Alternatively, agents (e.g., nucleic acids) may be in powder form for constitution with a suitable vehicle, e.g., sterile pyrogen-free water, before use. Agents (e.g., nucleic acids) may also be formulated in rectal or vaginal compositions such as suppositories or retention enemas, e.g., containing conventional suppository bases such as cocoa butter or other glycerides.

Other delivery systems can include time-release, delayed release or sustained release delivery systems. Such systems can avoid repeated administrations of the agents (e.g., antisense nucleic acids), increasing convenience to the subject and the physician. Many types of release delivery systems are available. They include polymer base systems such as poly(lactide glycolide), copolyoxalates, polycaprolactones, polyesteramides, polyorthoesters, polyhydroxybutyric acid, and polyanhydrides. Delivery systems also include non-polymer systems that are: lipids including sterols such as cholesterol, cholesterol esters and fatty acids or neutral fats such as mono, di, and tri glycerides; hydrogel release systems; silastic systems; peptide-based systems; wax coatings; compressed tablets using conventional binders and excipients; partially fused implants; and others disclosed herein.

EXAMPLES

Example 1: Interrupted Self-Complementary Nucleic Acid Sequences

Figure 3:
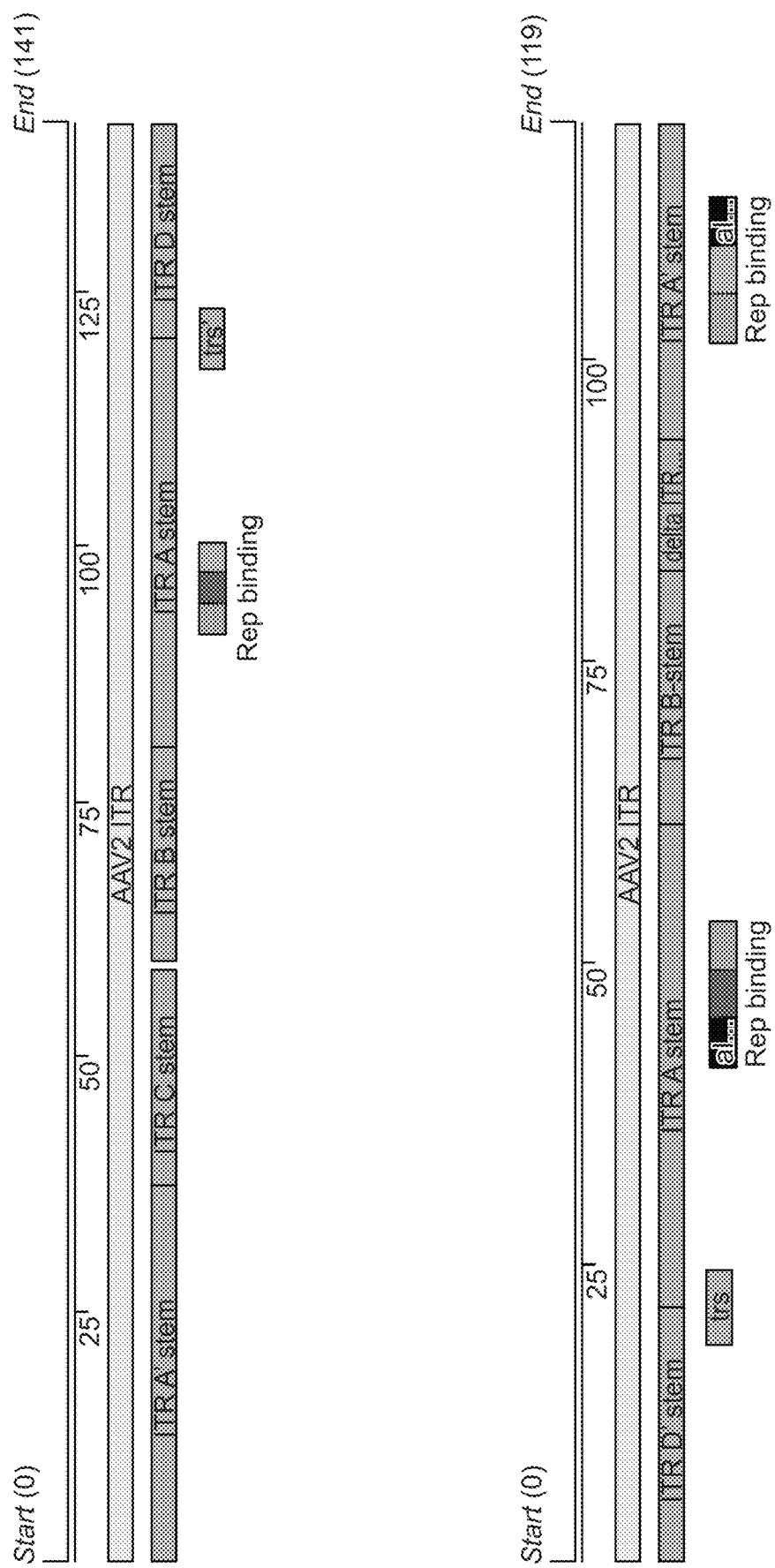
FIG. 3 is a graphic depiction of a pair of asymmetric ITRs. A full length AAV2 ITR is shown on top, and an AAV2 ITR having a truncation in the C-stem is depicted on the bottom. Both the full-length and the truncated ITR comprise an operative Rep-binding element (RBE) and an operative terminal resolution site (trs).

FIG. 1A shows a non-limiting example of an interrupted self-complementary nucleic acid sequence (which is an AAV2 ITR). As shown in the FIG. 1A, the nucleic acid forms a T-shaped hairpin structure having a stem portion (D-A-A') and a cross-arm sequence having opposing lengthwise stem-loops (B-B' and C-C'). The trs and RBE of the interrupted self-complementary nucleic acid sequence are also depicted. FIG. 1B shows several non-limiting examples of truncations in the "C-arm" of an interrupted self-complementary nucleic acid sequence. A graphic depiction of one example of asymmetric AAV2 ITRs is shown in FIG. 3.

Replication of ceDNA from Asymmetric AAV ITRs

Figure 2A:
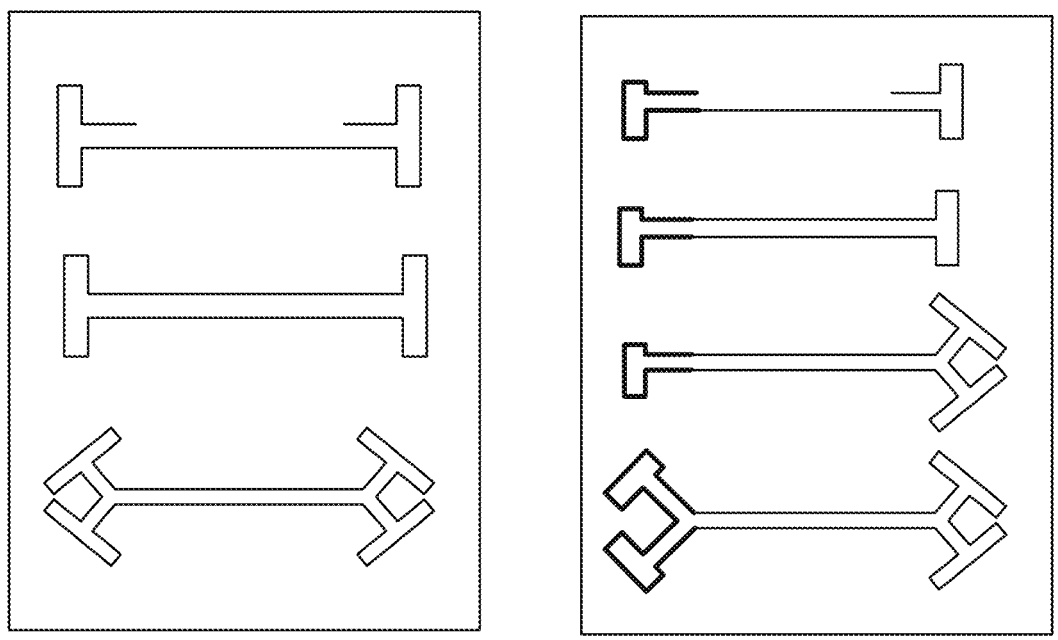
FIGS. 2A-2B show representations of symmetric and asymmetric open and closed-ended duplex DNA (ceDNA) molecules.
Figure 2B:
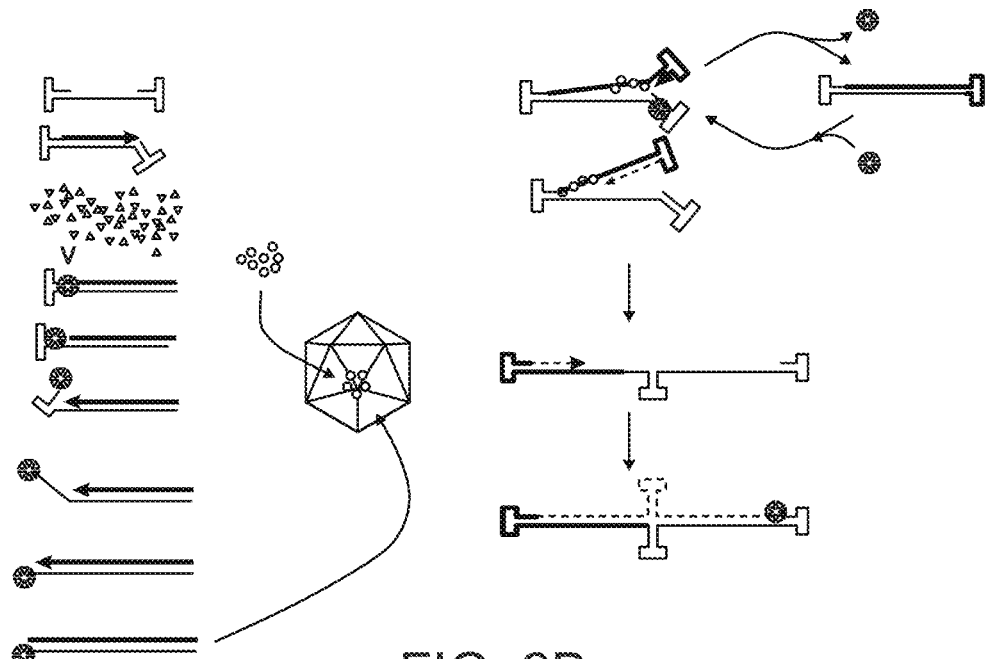

Adeno-associated virus (AAV) genomes are linear single-stranded DNA flanked by terminal palindromes typically referred to as inverted terminal repeats (ITRs) (FIG. 2A, left side). Except for 7 unpaired bases, the 145 nt ITR sequence is self-complementary and forms an energetically stable "T" shaped hairpin ($\Delta G \approx -72.4$ kcal per mol, Tm>80° C.) (FIG. 1A). During virus DNA replication, the cellular DNA polymerase complex initiates synthesis at the 3'-terminus of the template strand where the partial duplex formed by the ITR serves as the primer for primer extension. The replicative intermediate formed is an intramolecular duplex with the template and nascent strands covalently connected by the ITR. During a productive infection, a process called terminal resolution resolves the intra-strand ITR resulting in two full-length, complementary virus genomes (FIG. 2B, left side).

In the absence of AAV cap gene expression, an AAV vector genome having asymmetrical ITRs undergoes inefficient replication, and the replication products accumulate in a novel conformation of closed-ended linear duplex DNA (ceDNA). Due to inefficient replication (e.g., incomplete terminal resolution), the complementary strands of the intramolecular intermediate are now covalently linked through the ITRs on both ends of the genome (FIG. 2B, right side). Thus, in native conditions, ceDNA behaves as linear duplex DNA, however, in denaturing conditions, ceDNA strands melt apart, but remain linked, therefore transforming the linear duplex molecule into single-stranded circular DNA.

In some embodiments, ceDNA production from asymmetric AAV ITRs is dependent on a truncated ITR at one end and an operative (e.g., functional), wild-type (wt) or wt-like ITR on the opposite end of the transgene cassette. In some embodiments, the truncated ITR is inefficiently processed during the replication cycles of ceDNA in the Sf9 cells leading to an accumulation of replication intermediates, duplex monomer, duplex dimers, etc. In the absence of structural (capsid) protein expression, Rep 78 (or Rep 68) assembles on the intact ITRs and catalyze the site-specific nicking at the terminal resolution site. The reaction results in the formation of a transient tyrosine-phosphodiester (Y156 for AAV2 Rep 78 covalently linked to the 5' thymidine of the terminal resolution site 5'AGTTGG). The transient nucleoprotein complex then transfers the donor strand to the free 3'-terminus of the complementary strand. The ceDNA conformation therefore, results from the defective ITR on one end of the vector genome, an intact or operative ITR on the opposite end, and the co-expression of the p5 and p19 Rep proteins, where at least one p5 and one p19 Rep are expressed. Other parvovirus "small" Rep or NS proteins can substitute for AAV p19 Rep protein (Rep 52 and Rep 40). Since these small Rep proteins are non-processive, monomeric helicases, it is feasible that non-parvoviridae super family 2 (SF2) helicases can substitute for the AAV Rep proteins.

The dependovirinae have existed relatively unchanged for tens of millions (and likely, hundreds of millions) of years. It is hypothesized that they have developed a homeostatic or symbiotic relationship with their hosts in which the provirus in latently infected cells often localizes to the AAVS1 locus on human chromosome 19q, which appears to have no adverse effect on the host cell. While in latency, AAV gene expression is repressed by cellular factors, e.g., YY1, and by the p5 Rep proteins that acting servomechanistically, negatively regulate expression from the p5 and p40 promoters. Thus, latently infected cells have little or no detectable AAV proteins and limit the acquired immune response to cells that are synthesizing virus proteins.

Example 2: Purification of ceDNA

Plasmid purification protocols typically utilize silica gels for small plasmid quantities preparations or anion exchange chromatography diethylaminoethyl sepharose, (DEAE-sepharose, for example) for larger quantities. For large-scale pDNA purification, the *Escherichia coli* bacteria are lysed with sodium dodecyl sulfate (SDS) and the cell proteins and genomic DNA are precipitated by denaturation/neutralization cycle retaining the plasmid in solution. The renatured double-stranded pDNA binds to the positively charged DEAE group and following washing steps, the pDNA is displaced and eluted with a high salt buffer solution. Alternatively, silica gel membranes may be used for selective pDNA adsorption from the clarified bacterial lysate under high salt conditions and eluted in low or no iconicity buffer.

It was observed that ceDNA can be readily purified with the small scale silica gel-based process. Using the large-scale anion exchange protocol, ceDNA recovery was very inefficient and resulted in low yields.

A method for large-scale ceDNA purification from invertebrate Sf9 cells using silica gel membranes is described. Increasing the surface area of modified silica gel membrane (or chromatography medium) is one approach to improve the flow rate, adsorption, and recovery of ceDNA. Standard filter capsules are available in a wide-range of configurations ranging in size from 0.5 cm diameter to 20 cm diameter or more. The capsule may contain a single layer of silica gel membrane on a chemically inert support, or stacks of membranes separated by inert supports, or pleated membranes utilizing horizontal flow design. Tangential flow filtration (TFF) and hollow fiber filtration (HFF) are alternatives for the coaxial flow capsule filtration.

Example 3: ceDNA Constructs for Treatment of Disease

Figure 4:
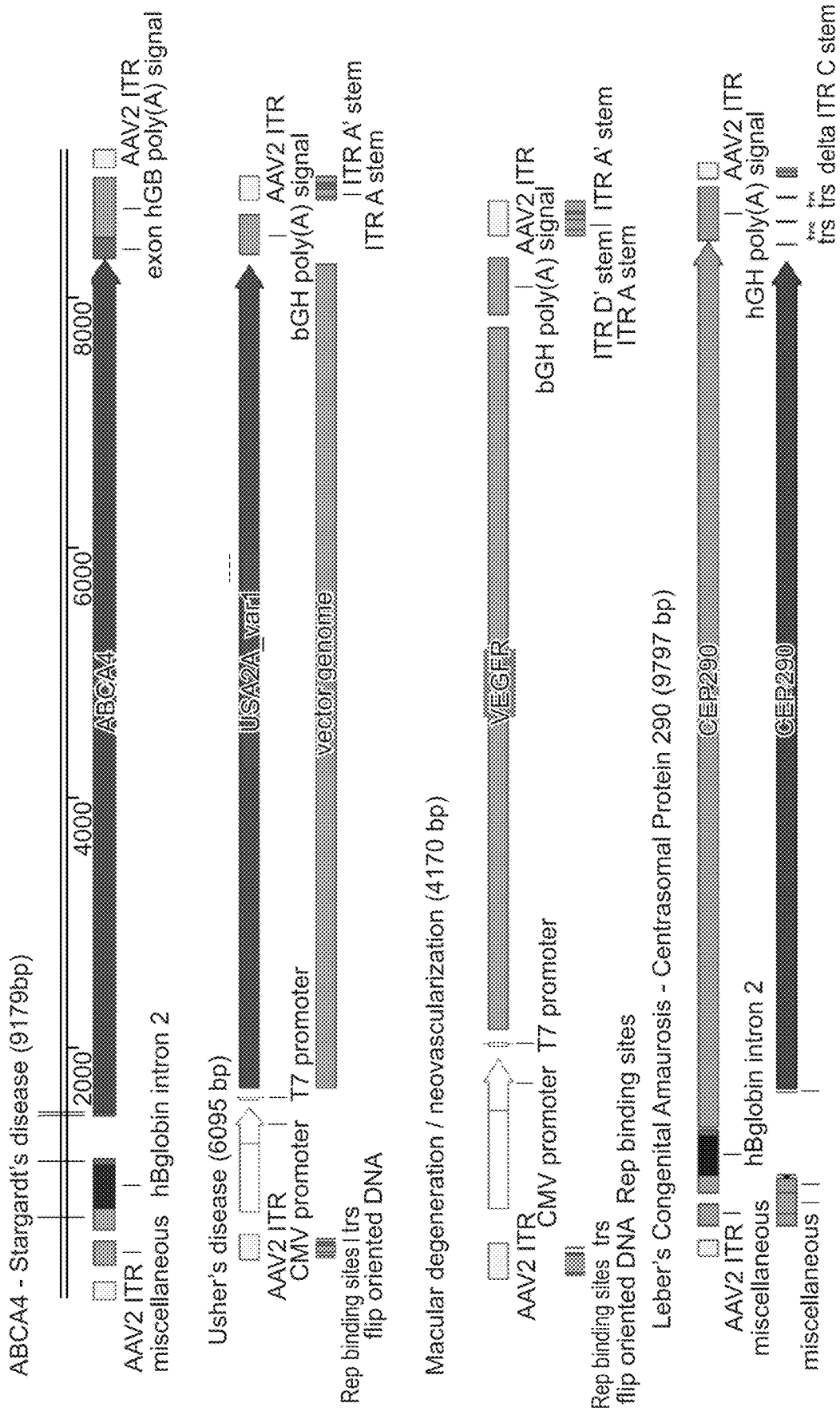
FIG. 4 shows non-limiting examples of nucleic acid constructs having asymmetric self-complementary nucleic acid sequences (e.g., AAV2 ITRs) and a transgene associated with ocular disease.

FIG. 4 shows non-limiting examples of nucleic acid constructs having asymmetric self-complementary nucleic acid sequences (e.g., AAV2 ITRs) and a transgene associated with ocular disease. The first nucleic acid construct of FIG. 4 depicts a non-limiting example of a nucleic acid molecule for treatment of Stargardt's disease. The nucleic acid comprises a pair of asymmetrical interrupted self-complementary nucleic acid sequences (e.g., asymmetric AAV2 ITRs) flanking a heterologous nucleic acid insert encoding the ATP-Binding Cassette, Sub-Family A (ABC1), Member 4 (ABCA4) protein. The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a hBglobin intron 2 positioned 5' to the heterologous nucleic acid insert, and a hGH poly(A) signal positioned 3' to the heterologous nucleic acid insert.

The second nucleic acid construct in FIG. 4 depicts a non-limiting example of a nucleic acid molecule for treatment of Usher's disease. The nucleic acid comprises a pair of asymmetrical interrupted self-complementary nucleic acid sequences (e.g., asymmetric AAV2 ITRs) flanking a heterologous nucleic acid insert encoding usherin protein (USH2A) variant 1. The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a CMV promoter and a T7 promoter positioned 5' to the heterologous nucleic acid insert, and a bGH poly(A) signal positioned 3' to the heterologous nucleic acid insert.

The third nucleic acid construct in FIG. 4 depicts a non-limiting example of a nucleic acid molecule for treatment of macular degeneration/neovascularization. The nucleic acid comprises a pair of asymmetrical interrupted self-complementary nucleic acid sequences (e.g., asymmetric AAV2 ITRs) flanking a heterologous nucleic acid insert encoding vascular endothelial growth factor receptor (VEGFR). The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a CMV promoter and a T7 promoter positioned 5' to the heterologous nucleic acid insert, and a bGH poly(A) signal positioned 3' to the heterologous nucleic acid insert.

The fourth nucleic acid construct in FIG. 4 depicts a non-limiting example of a nucleic acid molecule for treatment of Leber's congenital amaurosis. The nucleic acid comprises a pair of asymmetrical interrupted self-complementary nucleic acid sequences (e.g., asymmetric AAV2 ITRs) flanking a heterologous nucleic acid insert encoding centrosomal protein 290 (CEP290). The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a CMV promoter and a T7 promoter positioned 5' to the heterologous nucleic acid insert, and a bGH poly(A) signal positioned 3' to the heterologous nucleic acid insert.

Figure 5:
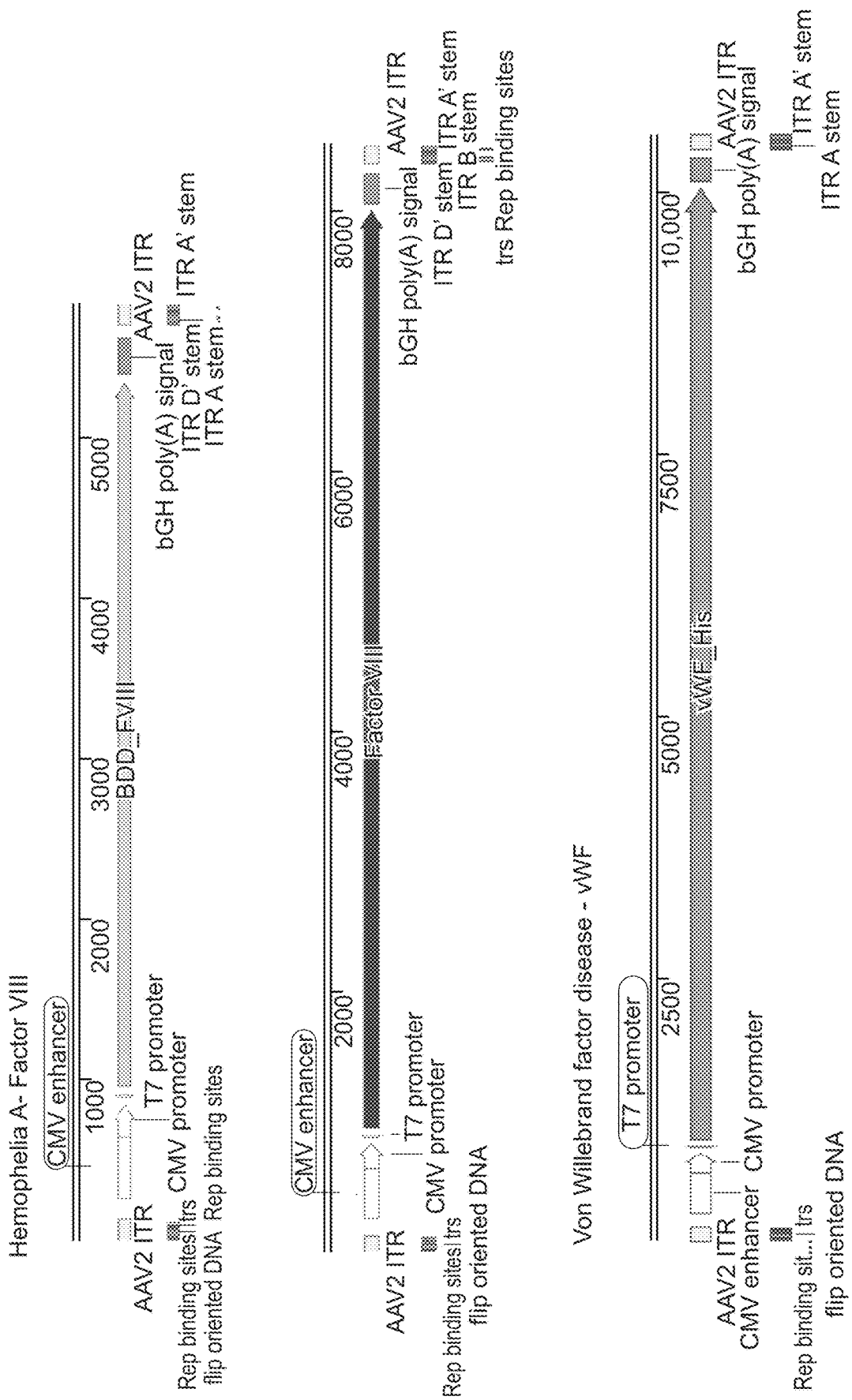
FIG. 5 shows non-limiting examples of nucleic acid constructs having asymmetric self-complementary nucleic acid sequences (e.g., AAV2 ITRs) and a transgene associated with blood disease.

FIG. 5 shows non-limiting examples of nucleic acid constructs having asymmetric self-complementary nucleic acid sequences (e.g., AAV2 ITRs) and a transgene associated with blood disease. The first nucleic acid construct in FIG. 5 depicts a non-limiting example of a nucleic acid molecule for treatment of Hemophilia A. The nucleic acid comprises a pair of asymmetrical interrupted self-complementary nucleic acid sequences (e.g., asymmetric AAV2 ITRs) flanking a heterologous nucleic acid insert encoding B-domain deleted factor VIII protein (BDD-FVIII). The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a CMV promoter/enhancer and a T7 promoter positioned 5' to the heterologous nucleic acid insert, and a bGH poly(A) signal positioned 3' to the heterologous nucleic acid insert.

The second nucleic acid construct in FIG. 5 depicts a non-limiting example of a nucleic acid molecule for treatment of Hemophilia A. The nucleic acid comprises a pair of asymmetrical interrupted self-complementary nucleic acid sequences (e.g., asymmetric AAV2 ITRs) flanking a heterologous nucleic acid insert encoding full-length factor VIII protein (FVIII), which exceeds the cloning capacity of traditional AAV vectors. The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a CMV promoter/enhancer and a T7 promoter positioned 5' to the heterologous nucleic acid insert, and a bGH poly(A) signal positioned 3' to the heterologous nucleic acid insert.

The third nucleic acid construct in FIG. 5 depicts a non-limiting example of a nucleic acid molecule for treatment of von Willebrand factor disease. The nucleic acid comprises a pair of asymmetrical interrupted self-complementary nucleic acid sequences (e.g., asymmetric AAV2 ITRs) flanking a heterologous nucleic acid insert encoding von Willebrand factor (vWF). The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a CMV promoter and a T7 promoter positioned 5' to the heterologous nucleic acid insert, and a bGH poly(A) signal positioned 3' to the heterologous nucleic acid insert.

Figure 6:
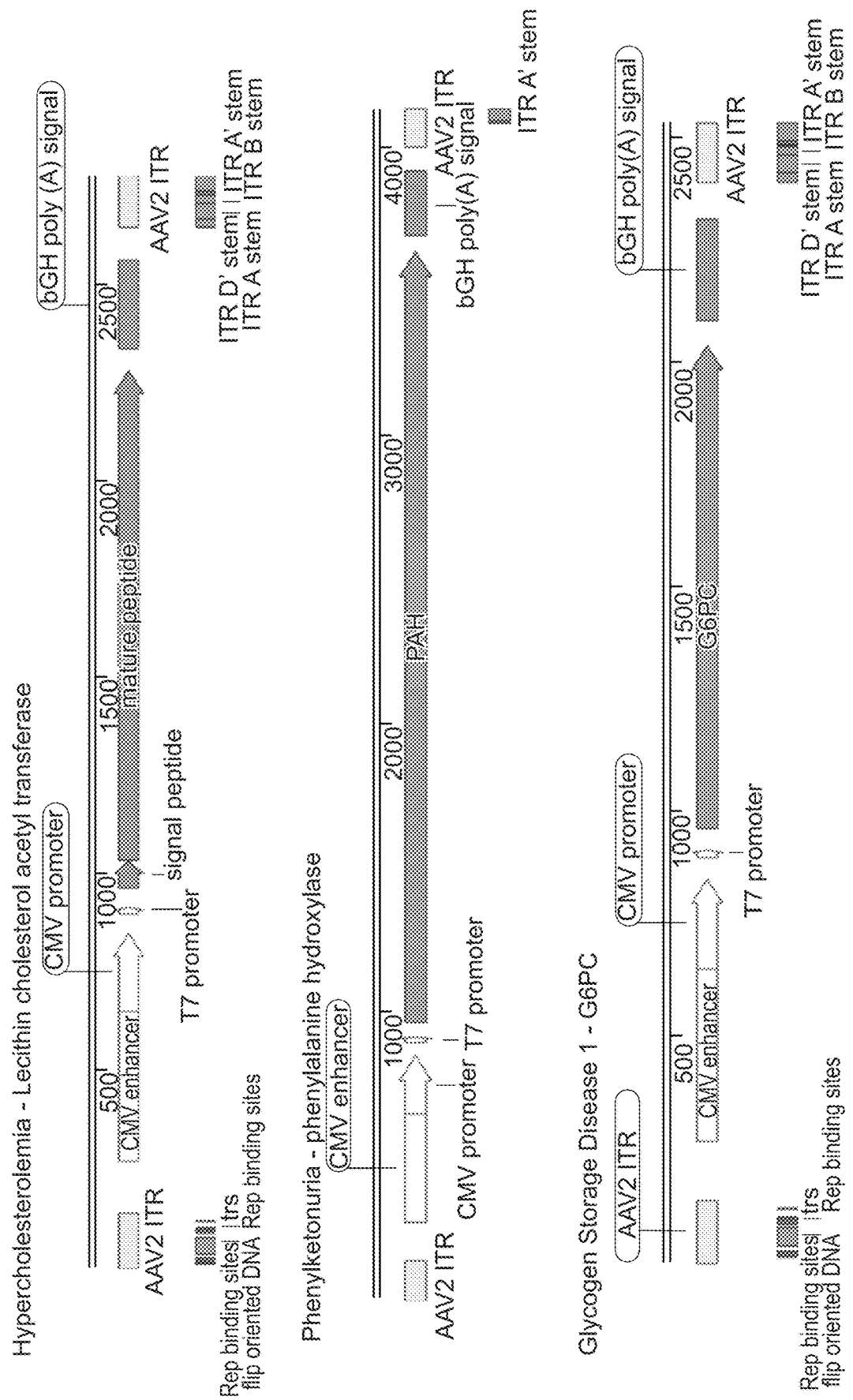
FIG. 6 shows non-limiting examples of nucleic acid constructs having asymmetric self-complementary nucleic acid sequences (e.g., AAV2 ITRs) and a transgene associated with liver disease.

FIG. 6 shows non-limiting examples of nucleic acid constructs having asymmetric self-complementary nucleic acid sequences (e.g., AAV2 ITRs) and a transgene associated with liver disease. The first nucleic acid construct in FIG. 6 depicts a non-limiting example of a nucleic acid molecule for treatment of hypercholesterolemia. The nucleic acid comprises a pair of asymmetrical interrupted self-complementary nucleic acid sequences (e.g., asymmetric AAV2 ITRs) flanking a heterologous nucleic acid insert encoding lecithin cholesterol acetyl transferase. The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a CMV promoter/enhancer and a T7 promoter positioned 5' to the heterologous nucleic acid insert, and a bGH poly(A) signal positioned 3' to the heterologous nucleic acid insert.

The second nucleic acid construct in FIG. 6 depicts a non-limiting example of a nucleic acid molecule for treatment of phenylketonuria (PKU). The nucleic acid comprises a pair of asymmetrical interrupted self-complementary nucleic acid sequences (e.g., asymmetric AAV2 ITRs) flanking a heterologous nucleic acid insert encoding phenylalanine hydroxylase (PAH). The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a CMV promoter/enhancer and a T7 promoter positioned 5' to the heterologous nucleic acid insert, and a bGH poly(A) signal positioned 3' to the heterologous nucleic acid insert.

The third nucleic acid construct in FIG. 6 depicts a non-limiting example of a nucleic acid molecule for treatment of Glycogen Storage Disease 1 (GSD1). The nucleic acid comprises a pair of asymmetrical interrupted self-complementary nucleic acid sequences (e.g., asymmetric AAV2 ITRs) flanking a heterologous nucleic acid insert encoding glucose 6-phosphatase catalytic subunit (G6PC). The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a CMV promoter/enhancer and a T7 promoter positioned 5' to the heterologous nucleic acid insert, and a bGH poly(A) signal positioned 3' to the heterologous nucleic acid insert.

FIG. 7 shows non-limiting examples of nucleic acid constructs having asymmetric self-complementary nucleic acid sequences (e.g., AAV2 ITRs) and a transgene associated with lung disease. The first nucleic acid construct in FIG. 7 depicts a non-limiting example of a nucleic acid molecule for treatment of cystic fibrosis. The nucleic acid comprises a pair of asymmetrical interrupted self-complementary nucleic acid sequences (e.g., asymmetric AAV2 ITRs) flanking a heterologous nucleic acid insert encoding cystic fibrosis transmembrane conductance regulator (CFTR). The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a CMV promoter/enhancer and a T7 promoter positioned 5' to the heterologous nucleic acid insert, and a bGH poly(A) signal positioned 3' to the heterologous nucleic acid insert.

The second nucleic acid construct in FIG. 7 depicts a non-limiting example of a nucleic acid molecule for treatment of alpha-1 antitrypsin deficiency. The nucleic acid comprises a pair of asymmetrical interrupted self-complementary nucleic acid sequences (e.g., asymmetric AAV2 ITRs) flanking a heterologous nucleic acid insert encoding alpha-1 antitrypsin (AAT). The AAV2 ITRs are asymmetric because one of the AAV2 ITRs (right side) contains a deletion in the C-stem region. Each interrupted self-complementary nucleic acid sequence includes an operative Rep-binding element (RBE) and an operative terminal resolution site (trs). The nucleic acid also encodes a CMV promoter/enhancer and a T7 promoter positioned 5' to the heterologous nucleic acid insert, and a bGH poly(A) signal positioned 3' to the heterologous nucleic acid insert.

Example 4: In Vivo Studies: Hydrodynamic Delivery of Naked DNA in Normal Male ICR Mice After infusing pDNA into mouse tail veins, lacZ expression decreased continuously between 24 hr and 5 weeks, corresponding to the quantity of pDNA per diploid genome. Mouse livers treated with ceDNA having asymmetric interrupted self-complementary sequences showed no change in lacZ activity between 24 hr and 1 week, however expression was substantially reduced at 5 wks. However, ceDNA in hepatocytes remained essentially unchanged at the 5 wk point. Similar results were obtained with thyroxine binding globulin promoter (TBG) GFP cassettes: little or no GFP expression and pDNA were detectable after 10 wks, whereas ceDNA TBG-GFP expression and DNA levels remained unchanged between 1 and 10 weeks.

Example 5: Ocular Delivery of ceDNA

Figure 8A:
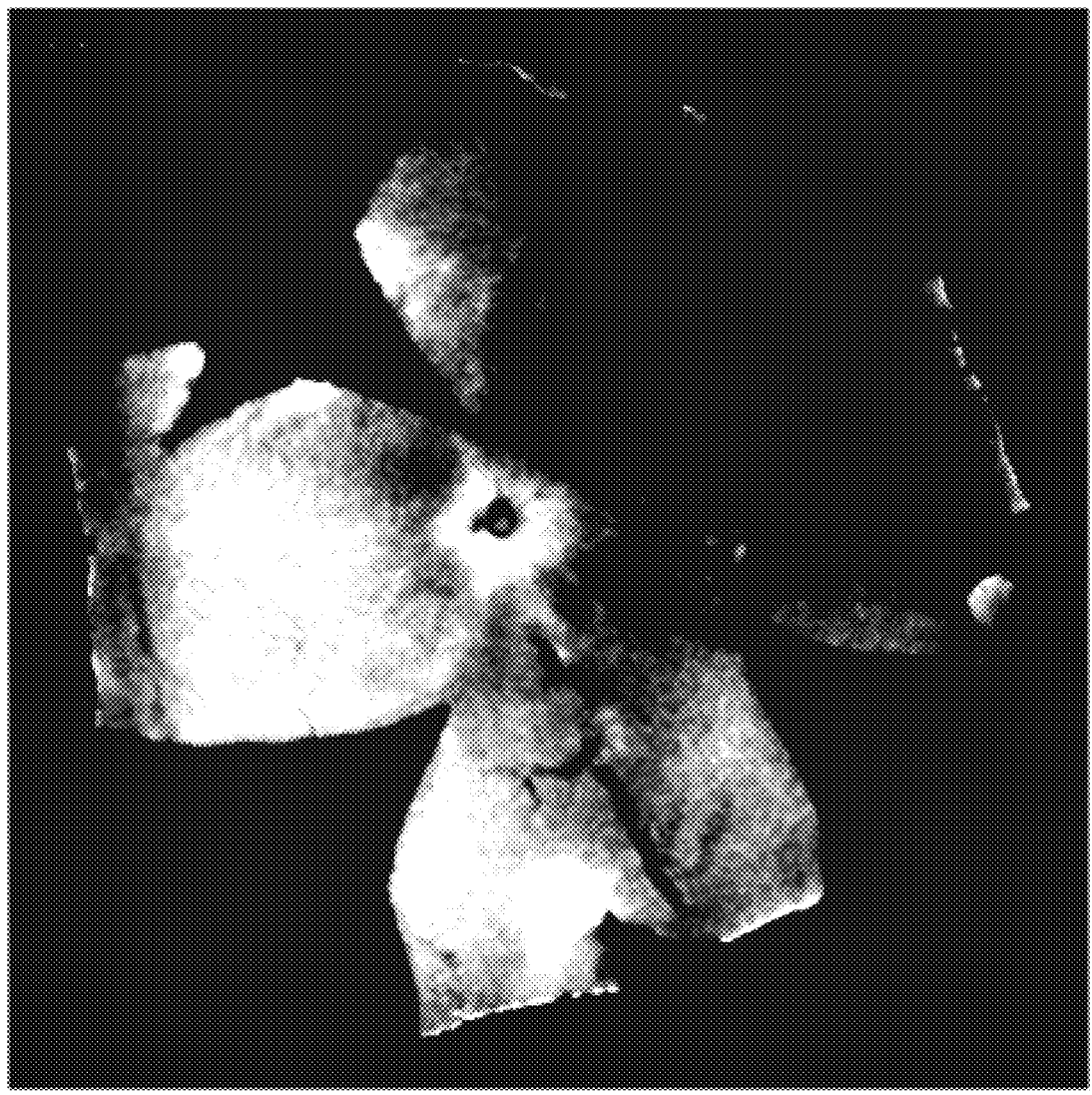
FIGS. 8A-8D show delivery of ceDNA to the eye. Adult mice were anesthetized by Ketamine/Xylazine (100/10 mg/kg) and the transfection agent was delivered intravitreally by a trans scleral injection of a volume of 1-2 µl. Antibiotic ointment was applied on cornea to prevent eye from drying while the mouse was recovering. Mouse was allowed to recover at 37 degree and then placed back into the mouse room for 2 weeks and the euthanized by $CO_2$ asphyxiation. Retina was dissected and processed for flat mount or section. No GFP antibody staining was necessary to detect transfected cells.
Figure 8B:
Figure 8C:
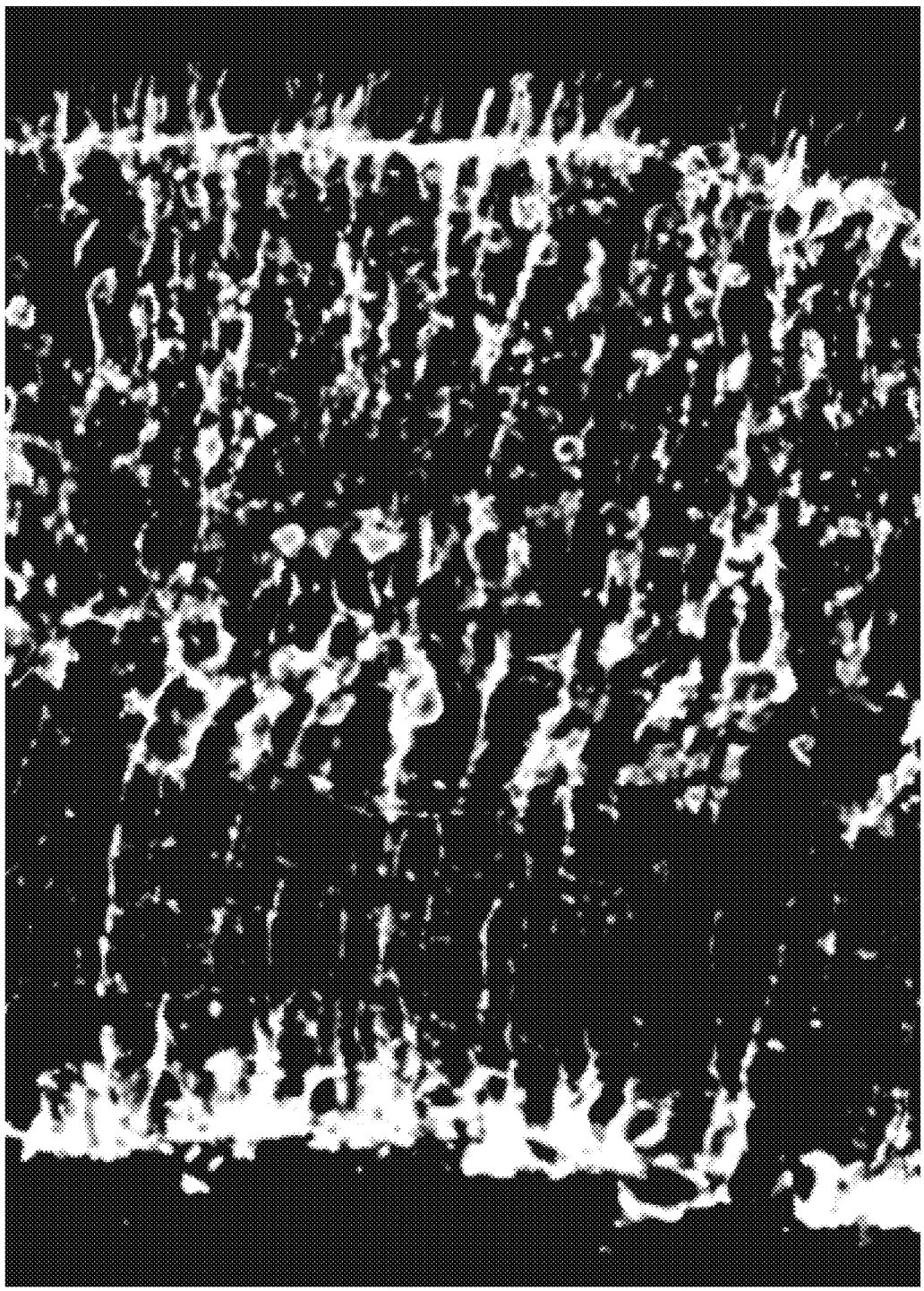
Figure 8D:
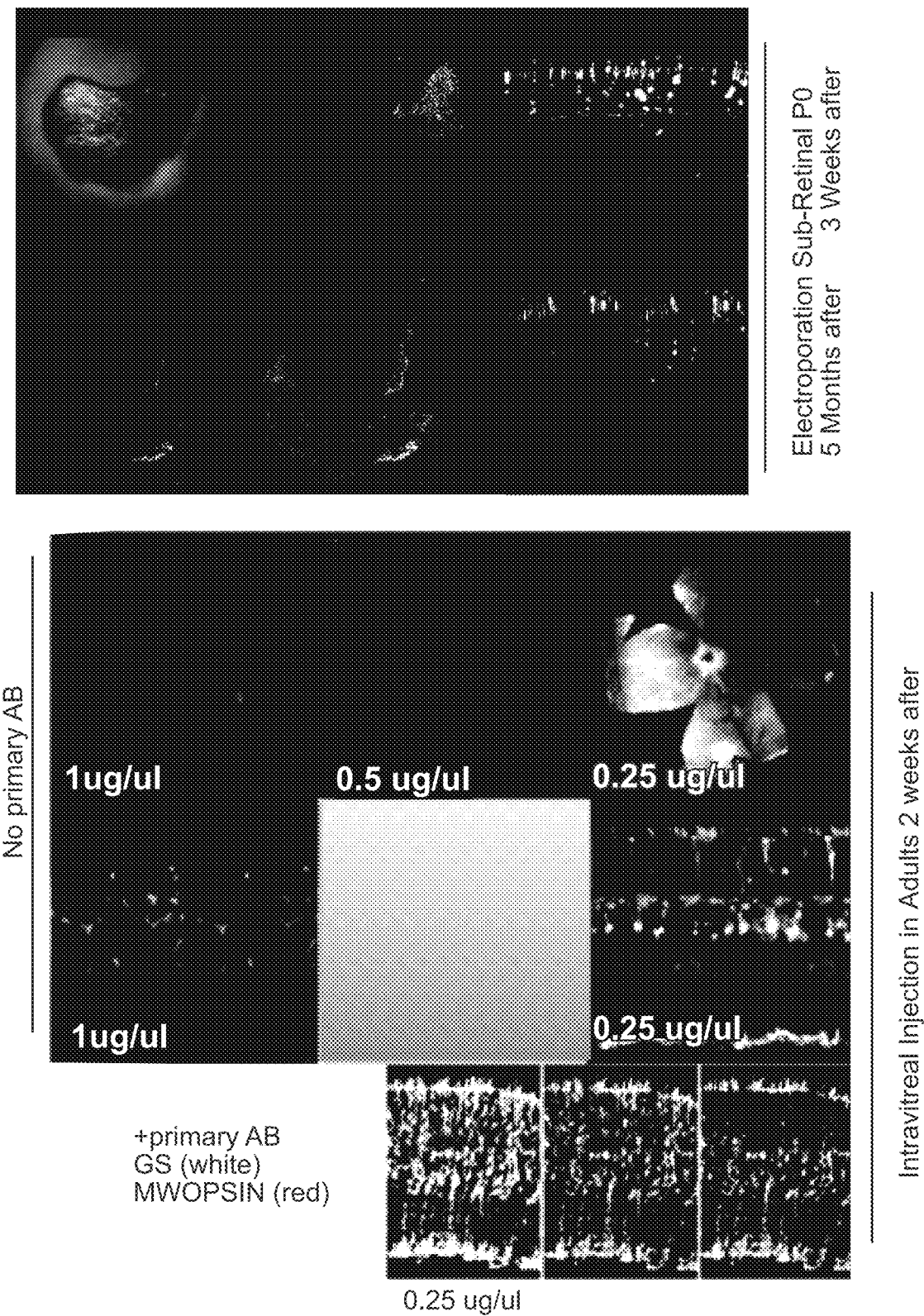

Direct GFP fluorescence was observed uniformly in cells spanning the width of the retina. FIGS. 8A-8D show delivery of ceDNA having asymmetric interrupted self-complementary sequences to the eye. Adult mice were anesthetized by Ketamine/Xylazine (100/10 mg/kg) and the transfection agent was delivered intravitreally by a trans scleral injection of a volume of 1-2 µl. Antibiotic ointment was applied on cornea to prevent eye from drying while the mouse was recovering. Mouse was allowed to recover at 37 degree and then placed back into the mouse room for 2 weeks and the euthanized by $CO_2$ asphyxiation. Retina was dissected and processed for flat mount or section. No GFP antibody staining was necessary to detect transfected cells. FIG. 8A shows a flat mount of GFP fluorescence on a mouse retina. FIG. 8B shows GFP fluorescence in a cross section of the retina. FIG. 8C shows GFP fluorescence and glial cell staining in a cross section of the retina. FIG. 8D shows GFP fluorescence in mouse retina after delivery of ceDNA by sub-retinal electroporation (top) and intravitreal injection (bottom).

Figure 9A:
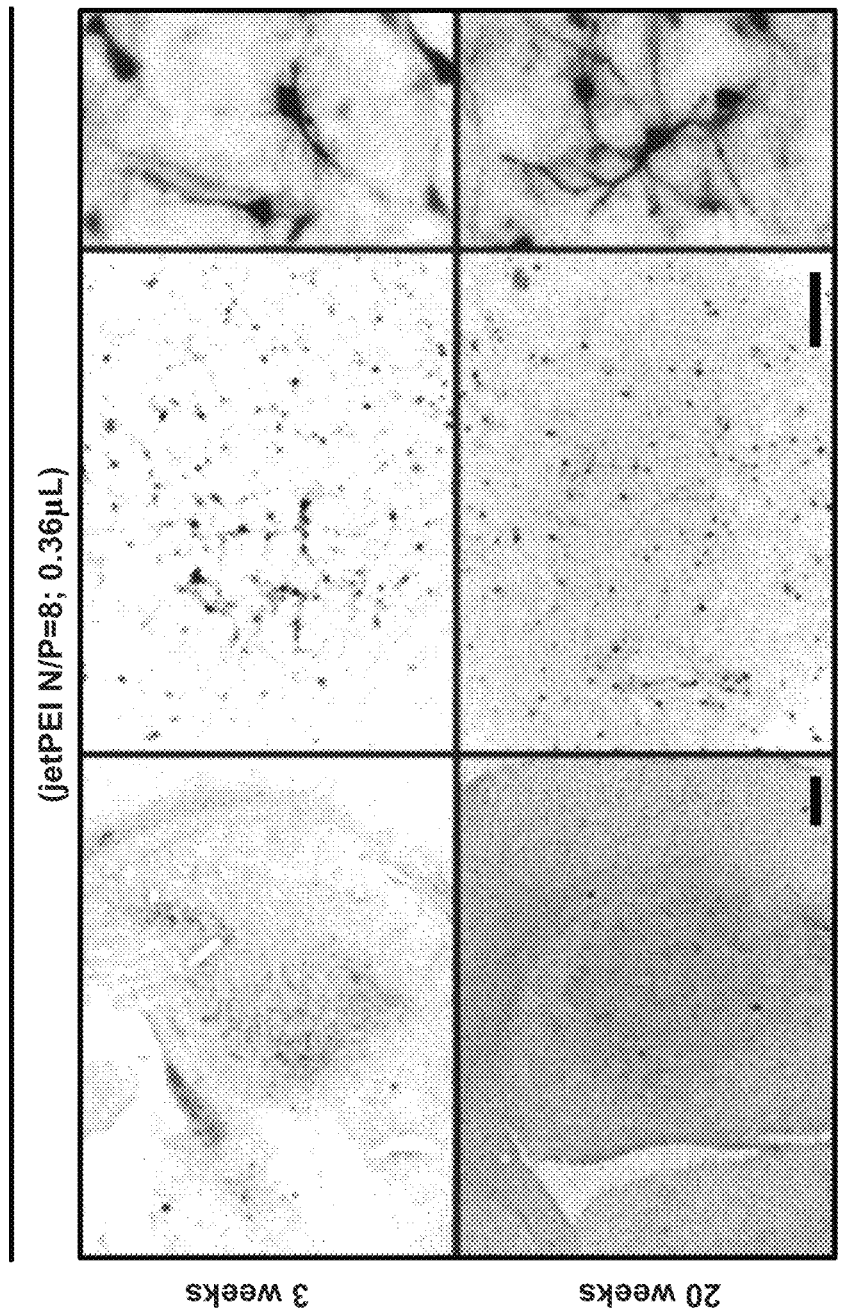
FIGS. 9A-9C show intracranial injection of ceDNA-GFP (e.g., ceDNA having asymmetric interrupted self-complementary sequences and encoding GFP) formulated with in vivo jetPEI, into rat striatum.
Figure 9B:
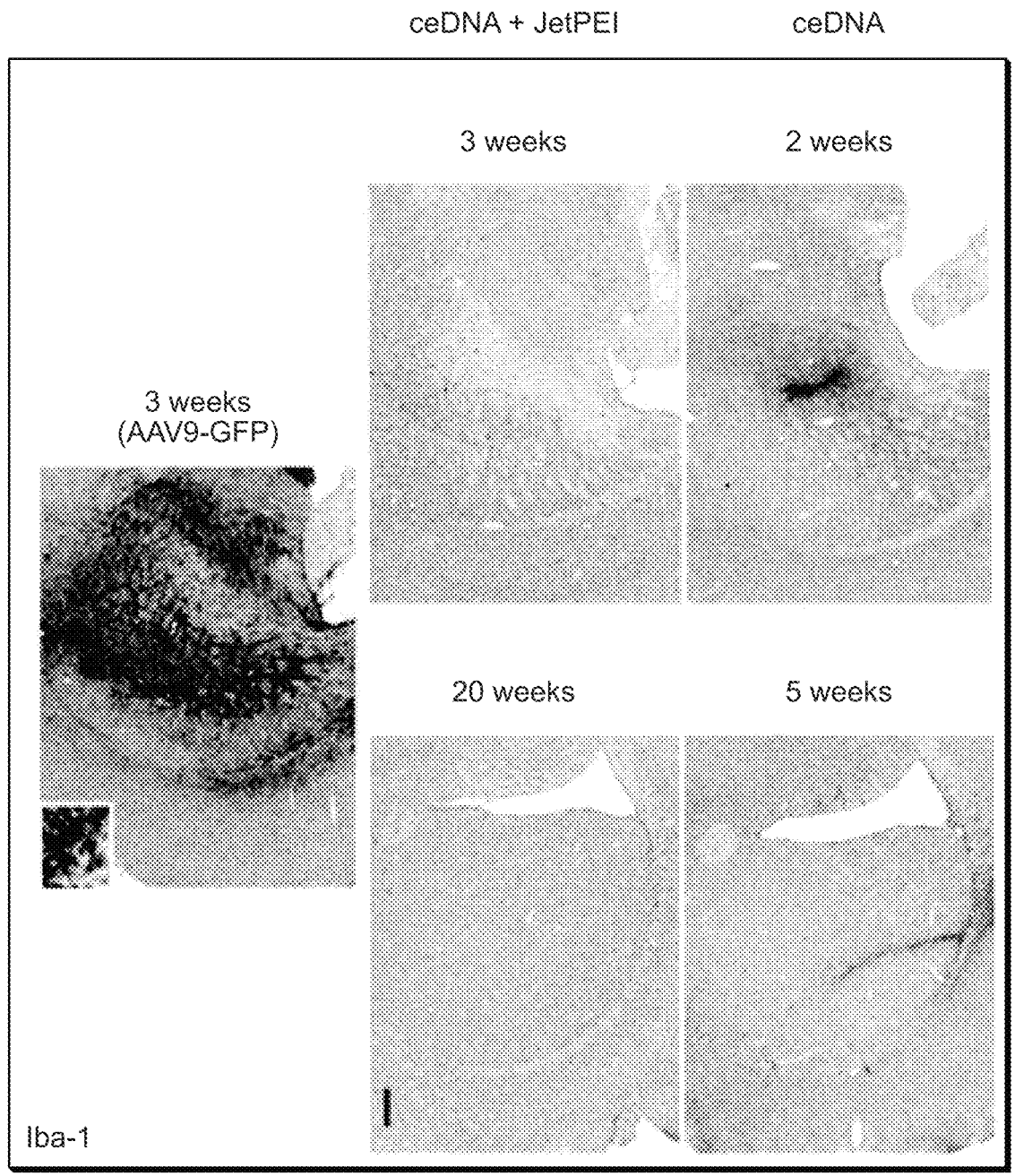
Figure 9C:
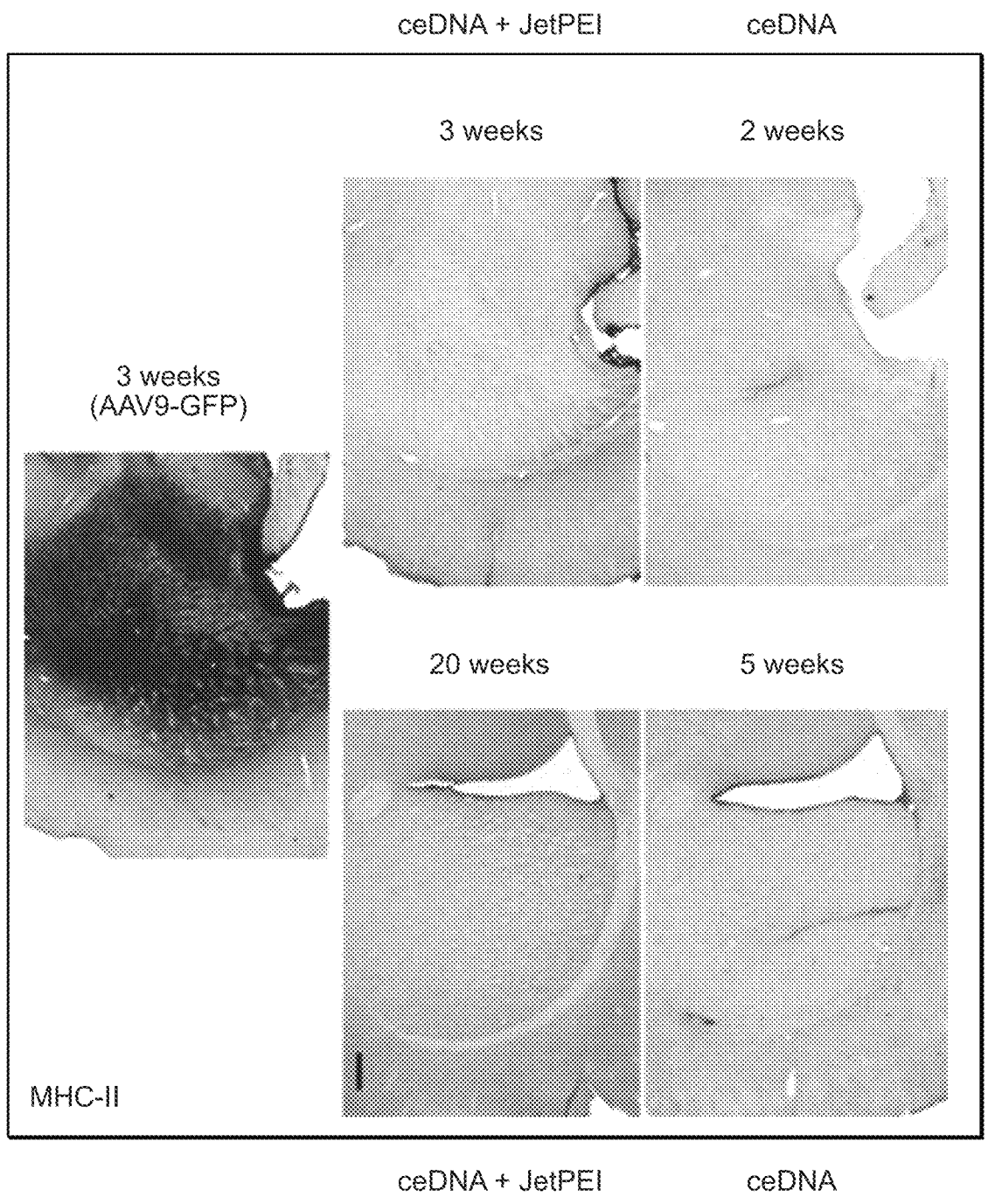

Example 6. In Vivo Studies: Intrastriatal Delivery in Rats ceDNA-GFP (ceDNA having asymmetric interrupted self-complementary sequences) was formulated with a commercially available transfection reagent, in vivo jetPEI, under an appropriate concentration (Polyplus Corp.) and injected into intracranially into rat striatum (FIG. 9A). Rats were sacrificed 3 wks and 20 wks post-injection and following processing, brain sections were examined using immunohistochemistry (IHC) with antibodies (Abs) against GFP, MHCII, and Iba1. Similar GFP expression was seen at 3 wks and 20 wks. At 3 wks, no MHCII or Iba1 antigen was detected in the brain sections, as shown in FIGS. 9B-9C.

Example 7: Sf9 Infection to Produce ceDNA

Transposition into Bacmid

DH10Bac competent cells (Invitrogen) were thawed on ice. 50 µl of cells were dispensed into 14 ml tubes, add 50 ng of plasmid DNA (e.g., a plasmid comprising a protein-encoding transgene flanked by asymmetric interrupted self-complementary sequences) and gently mix. The DNA sequence of the plasmid described in this example is represented by SEQ ID NO: 25. The DNA sequence of the region of the plasmid comprising a protein-encoding transgene flanked by asymmetric interrupted self-complementary sequences is represented by SEQ ID NO: 26

Figure 10A:
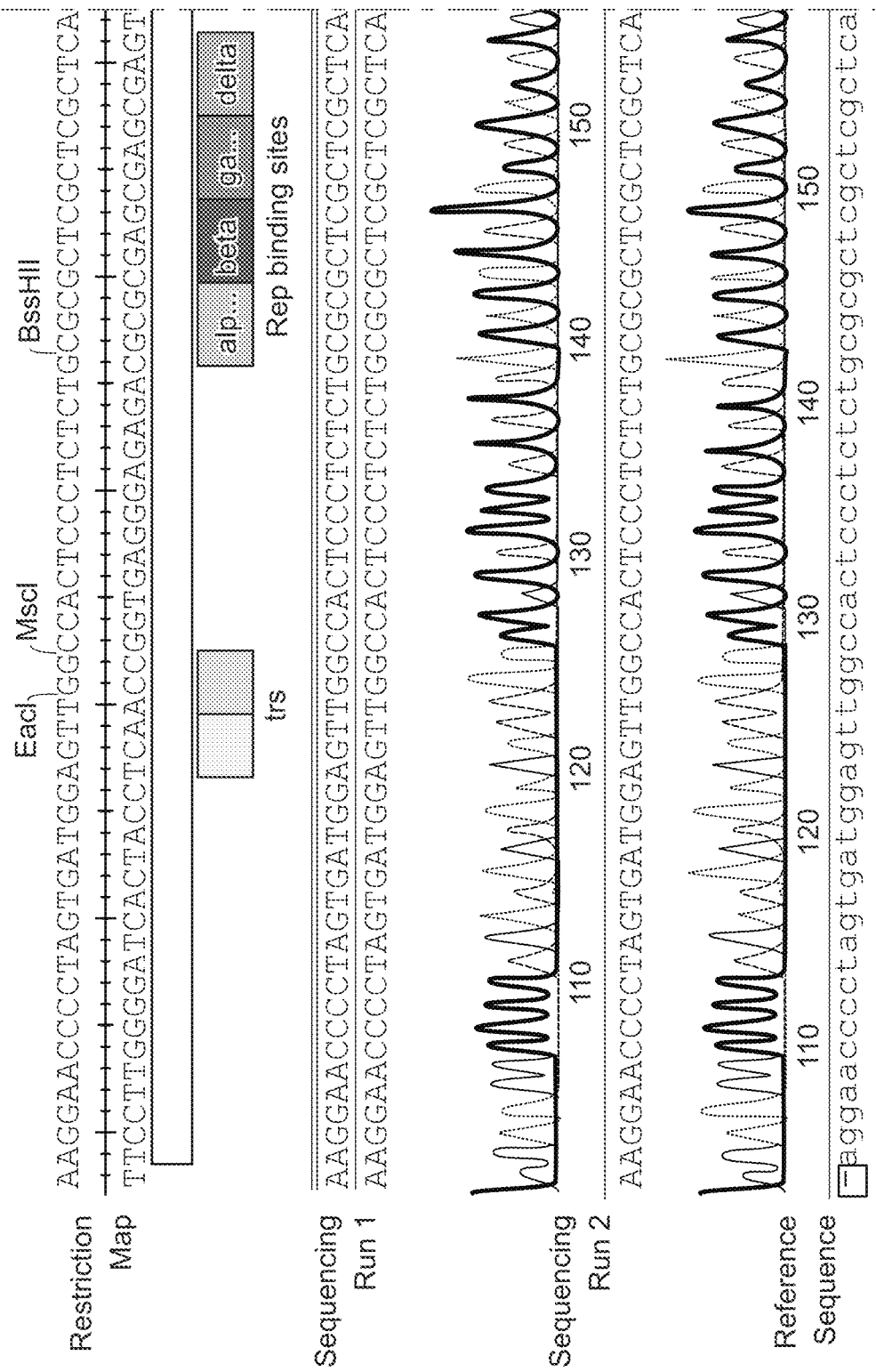
Figure 10A:
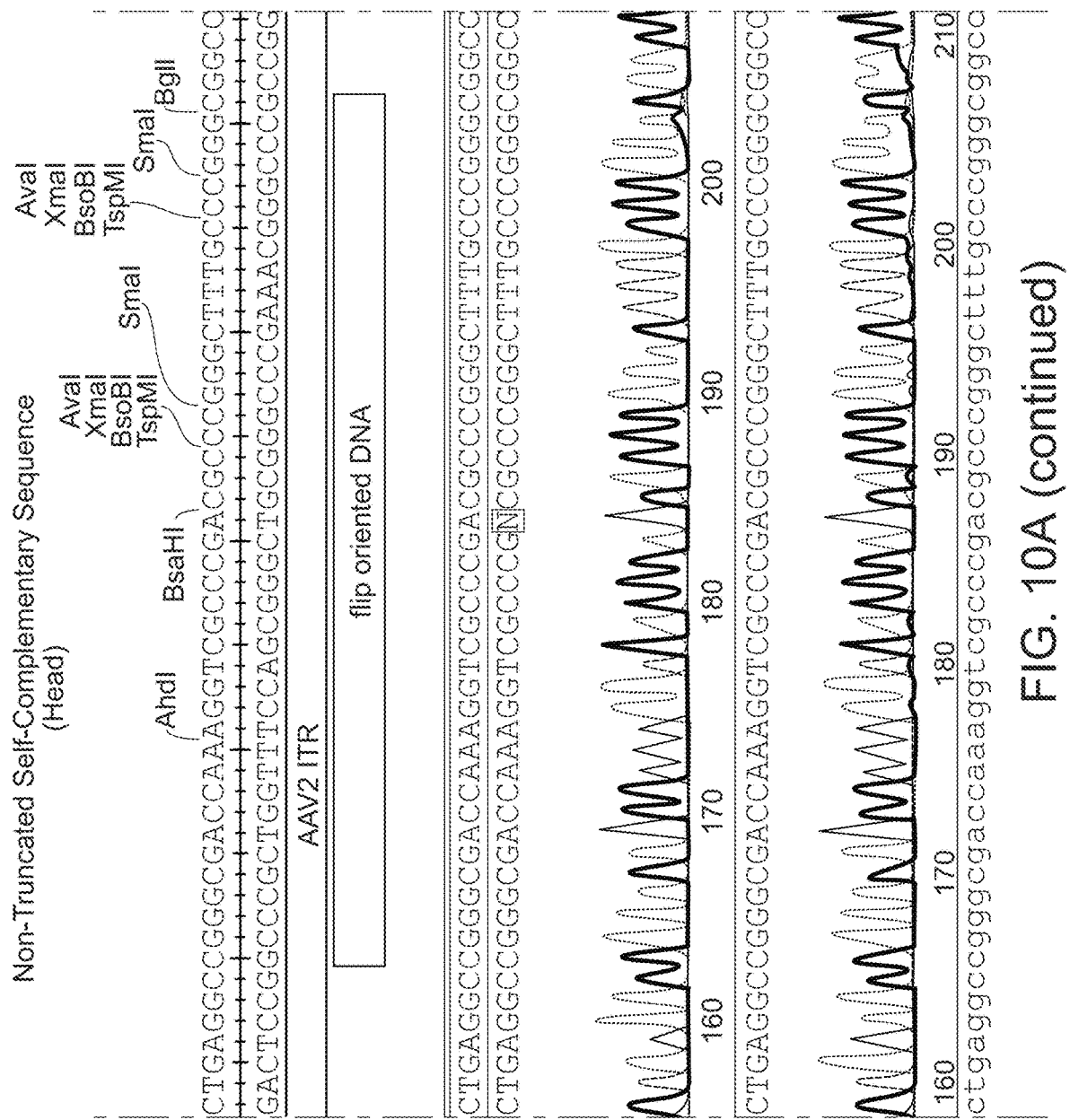
Figure 10A:
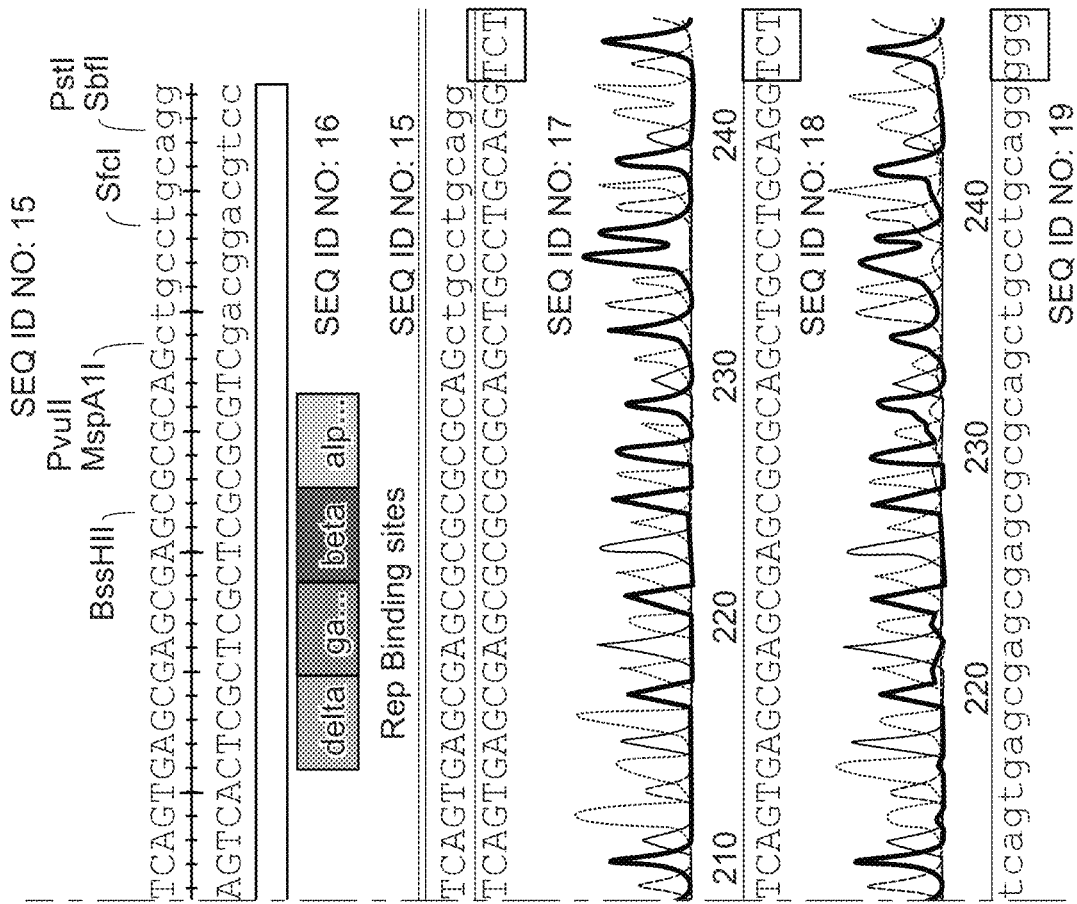
Figure 10B:
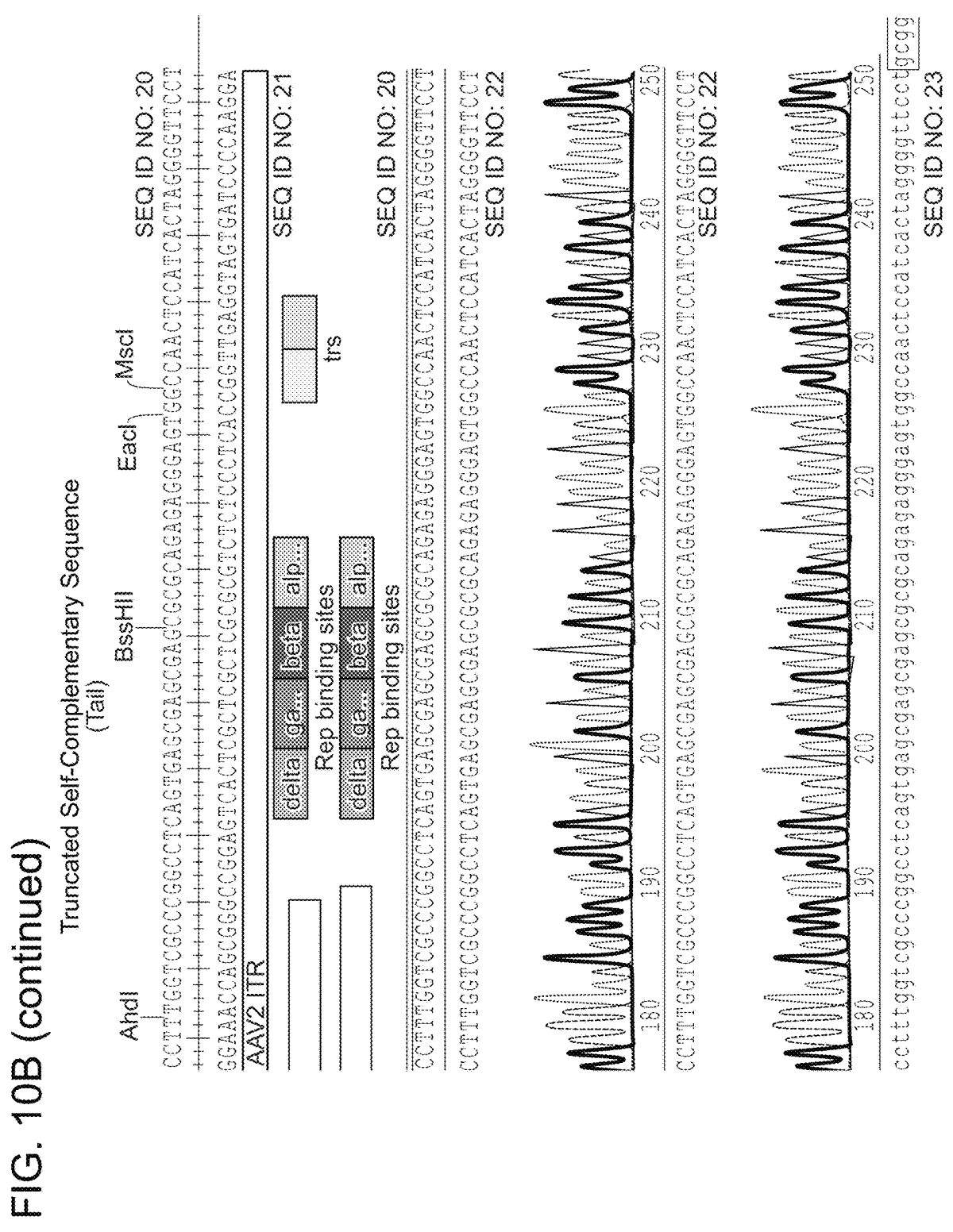

Sequence analysis of the plasmid DNA interrupted self-complementary sequences is shown in FIGS. 10A-10B. The 5' self-complementary sequence (referred to as the head portion, which is upstream of the coding sequence of the transgene) is shown in FIG. 10A. This was sequenced using a primer complementary with the CMV promoter of the plasmid construct. FIG. 10A shows a restriction map of the plasmid in the region of the 5' self-complementary sequence. Two runs of the plasmid sequence results are aligned with a reference sequence, which is a wild-type AAV2 ITR sequence.

The 3' self-complementary sequence (referred to as the tail portion, which is downstream of the coding sequence of the transgene) is shown in FIG. 10B. This was sequenced using a primer complementary with the SV40 promoter of the plasmid construct. FIG. 10B shows a restriction map of the plasmid in the region of the 3' self-complementary sequence. Two runs of the plasmid sequence results are aligned with a reference sequence, which is a wild-type AAV2 ITR sequence. The results show a truncation within the self-complementary sequence with corresponds to one arm of the cross-arm structure.

These results confirm that the plasmid DNA construct encodes a transgene flanked by asymmetric interrupted self-complementary sequences. The asymmetry arises because the 5' self-complementary sequence encodes a complete cross-arm; whereas the 3' self-complementary sequence encodes a truncated cross-arm.

The tubes were then incubated on ice for 30 min and then heat shocked in 42° C. water bath for 45 sec. Tubes were then chilled on ice for 2 min. 450 µl of SOC media was added to the tubes and they were shaken in a 37° C. incubator for 4 hrs. Aliquots were diluted 1:10 and 50 µl were plated on agar plates containing 50 µg/ml kanamycin, 7 µg/ml gentamicin, 10 µg/ml tetracycline, 100 µg/ml Bluo-gal and 40 µg/ml IPTG. Plates were incubated 48 hrs at 37° C. or 72 hrs at 30° C. A single white colony was picked, and struck on a fresh plate to make sure it was not contaminated with a blue colony, then incubated overnight. Glycerol stocks were created.

Prepare DNA from Bacmid

The bacmid was incubated into 10 ml LB media with 50 µg/ml kanamycin, 7 µg/ml gentamycin, 10 µg/ml tetracycline and grown in a 37° C. shaking incubator overnight. The culture was spun down at 8000 rpm for 10 min. The supernatant was removed and the pellet was resuspended in 1.5 ml of P1 buffer from a Qiagen extraction kit. 1.5 ml of Buffer 2 was added and the tube was inverted 4-6 times. 2.1 ml of Buffer P3 was added and the tube was inverted 4-6 times. The precipitants were passed through a Qiagen syringe filter and centrifuged 8000 rpm for 10 min. The clean lysis solution was transferred to a tube containing 5 ml of isopropanol and mixed well and centrifuged at 4° C. for 30 min at maximum speed. The supernatant was removed and 3 ml of 70% ethanol was added to wash the pellet. The pellet was then spun at 8000 rpm for 10 min. The pellet was then washed and air dried. The DNA was then resuspended in 200 µl TE buffer. An aliquot was removed and optical density (OD) at 260 nm was read to quantify DNA concentration.

Production of P1 Baculovirus Expression Vectors (BEV)

A total of $4 \times 10^6$ Sf9 cells were seeded in 5 ml of media in T25 TC flask. The flask was placed on a horizontal surface during cell attachment so that the cells will be uniformly distributed. Generally, cells attach within 15 min. 1 µg of Bacmid DNA was diluted in 75 µl of water. 6 µl of Promega Fugene HD was diluted into 69 µl of water in a separate tube. The diluted Fugene HD was mixed with diluted DNA by pipetting up and down several times. After 15 min, the DNA/lipid complexes were added to the Sf9 cells. P1 baculovirus expression vector (BEV) were harvested after 4 days. Briefly, all media was removed from the flask using a 5 ml pipette and transferred to 15 ml a polystyrene tube. The container was spun at 1200 g for 10 min to pellet any cells or debris that might have been picked up. BEV were decanted into a fresh 15 ml tube and virus was stored at 4° C.

Production of Baculovirus-Infected Insect Cells (Biics)

50 ml of Sf9 cells were infected at a concentration of $2.5 \times 10^6$ cells/ml with 1 ml of BEV (1:50). Cells were counted and their diameter was checked on day 1 (e.g., checked to see if the cell count reaches $2 \times 10^6$/ml and cells measure~15-16 µm in diameter) and day 2 (e.g., checked to see if the cell count reaches between $4-5 \times 10^6$ cells/ml and the diameter measures~18-19 µm). Cells were spun down when they look infected at 300×g for 5 min. The supernatant was removed and the pellet was resuspended in freezing media to have a final concentration of $20 \times 10^7$ cells/ml. Cells can be frozen at −80° C. in rack with isopropanol for storage.

Test Efficiency of Infectivity for Titerless Infected Baculovirus Stock (TIPS)

Four flasks of 20 ml at $2.5 \times 10^6$ cells/ml were prepared. Cells were infected with 4 different dilutions of titerless infected baculovirus stock (TIPS), for example 1/1,000, 1/10,000, 1/50,000, 1/100,000. Cells were grown and diameter, viability and cell counts were assessed for 3 days. To determine the efficiency of TIPS stock check which dilution reached the following criteria after 3 days: viable cells 4 to $5 \times 10^5$ cells/ml, viability 85 to 95%, diameter 18 to 20 µm.

Production of ceDNA:

$2.5 \times 10^6$ cells/ml Sf9 cells were co-infected with TIPS for Rep protein and transgene of interest (e.g., GFP). After 4-5 days cells were observed for diameter and viability. Cells in the pellet were collected by spinning down in a centrifuge at 4150 rpm for 30 min. Cells were then frozen or ceDNA was extracted, for example by Qiagen Midi Plus purification protocol.

Analysis of ceDNA ceDNA were analyzed by native gel electrophoresis and/or denaturing gel electrophoresis, with restriction digestion. For example a single cut restriction enzyme approximately ⅔ into the ceDNA sequence between ITRs was selected, and the resulting restriction digest products were run on an agarose gel.

Figure 10C:
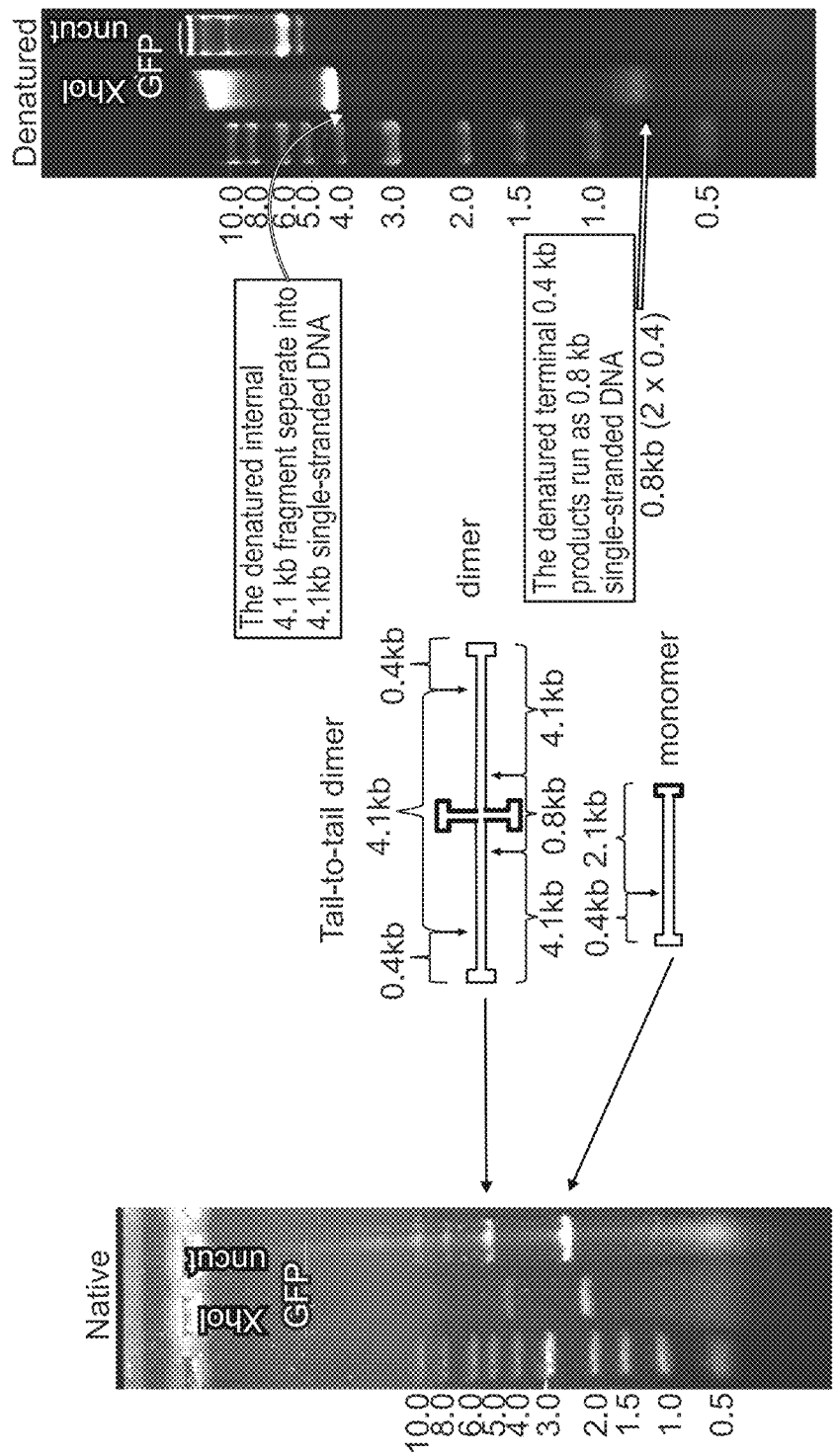
FIG. 10C shows agarose gel electrophoretic separation of ceDNA-GFP. The left side of the figure shows native gel electrophoresis of uncut ceDNA-GFP and ceDNA-GFP digested with XhoI. Monomeric (~2.1 kb) and dimeric (~4.1 kb) conformer products are observed in the native gel; the 0.4 terminal fragment is obscured by fluorescence of impurities at the bottom of the gel. The right side of the figure shows denaturing gel electrophoresis of uncut ceDNA-GFP and ceDNA-GFP digested with XhoI. The dimeric (~4.1 kb) conformer product is observed in the denaturing gel; denatured terminal 0.4 kb products that run as a single stranded DNA at 0.8 kb are also observed.

FIG. 10C shows the ~4.5 kb of a ceDNA comprising a GFP transgene (ceDNA-GFP) was electrophoretically separated into different conformers (e.g., monomer, dimer, trimer, etc.) under native (left) and denaturing (right) conditions, following digestion with the single-cutter, XhoI.

On a native gel (FIG. 10C, left), the monomers were resolved into two products: 2.1 kb and 0.4 kb. The dimers were resolved into either 4.1 kb/0.4 kb products, or 4.1 kb/0.8 kb products, depending upon the orientation (e.g., tail-to-tail, or head-to-head) of the dimer subunits. The products that result from tail-to-tail organization of the dimer were indicated by the downward pointing arrows. The 0.4 kb terminal fragment was obscured by the fluorescence of the impurities at the bottom of the gel. The upward facing arrows indicate the products resulting from the head-to-head dimer. Heavy weighted lines indicate the position of the truncated ITR. In the monomer, the deleted ITR was on the right side of the ceDNA molecule and in the tail-to-tail dimer, the truncated ITR was internal (at the mirror plane). In the head-to-head conformation, the truncated ITR would be at the ends of the molecule.

On a denaturing gel (FIG. 10C, right), the dimeric ceDNA-GFP produced a band at 4.1 kb and 0.8 kb (which correlates to the denatured 0.4 kb terminal products running on the gel as a 0.8 kb single-stranded DNA). As described above, the predicted products for head-to-head ceDNA-GFP dimers were 0.8 kb and 4.1 kb on native gels, and 0.8 kb and 8.2 kb on denaturing gels. The denaturing gel shows no band at 8.2 kb and therefore indicates that the predominant form of the ceDNA-GFP dimer was tail-to-tail.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. An isolated nucleic acid comprising a nucleic acid insert comprising a transgene;
  wherein the insert is flanked by at least two adeno-associated virus (AAV) inverted terminal repeat (ITR) sequences;
    wherein the at least two ITR sequences are asymmetric and covalently linked with respect to one another;
    wherein each of the at least two ITR sequences has an operative terminal resolution site and a rolling circle replication protein rep binding element (RBE);
      wherein a first ITR sequence is interrupted by a cross-arm sequence forming two opposing, lengthwise-symmetric stem-loops, each of the opposing lengthwise-symmetric stem-loops having a stem portion in the range of 5 to 15 base pairs in length and a loop portion having 2 to 5 unpaired deoxyribonucleotides;
      wherein a second ITR sequence is interrupted by a truncated cross-arm sequence having one or more deletions of between 11 and 20 nucleotides in a palindromic sequence region B-B' and/or a palindromic sequence region C-C'; and
  wherein the isolated nucleic acid is a closed-ended linear duplex DNA (ceDNA).

2. The isolated nucleic acid of claim 1, wherein the at least two ITRs are in the range of 40 to 1000 nucleotides in length.

3. The isolated nucleic acid of claim 1, wherein the truncated cross-arm sequence has a Gibbs free energy (ΔG) of unfolding under physiological conditions in the range of −12 kcal/mol to −30 kcal/mol.

4. The isolated nucleic acid of claim 1, wherein the RBE comprises the sequence 5'-GCTCGCTCGCTC-3' (SEQ ID NO: 1).

5. The isolated nucleic acid of claim 1, wherein the operative terminal resolution site comprises a sequence 5'-TT-3' or wherein the 3' end of the operative terminal resolution site is 15 to 25 nucleotides from the 5' end of the rolling circle replication protein binding element.

6. The isolated nucleic acid of claim 1, wherein the truncated cross-arm sequence forms two opposing, lengthwise-asymmetric stem-loops, optionally wherein one of the opposing, lengthwise-asymmetric stem-loops has a stem portion in the range of 8 to 10 base pairs in length and a loop portion having 2 to 5 unpaired deoxyribonucleotides or one lengthwise-asymmetric stem-loop has a stem portion less than 8 base pairs in length and a loop portion having 2 to 5 deoxyribonucleotides.

7. The isolated nucleic acid of claim 1, wherein the nucleic acid insert comprising a transgene is engineered to express a protein or functional RNA.

8. The isolated nucleic acid of claim 1, wherein the nucleic acid insert is in the range of 500 to 50,000 nucleotides in length and is a promoterless construct as a substrate for gene editing selected from the group consisting of a substrate for TALENS, a substrate for zinc finger nucleases (ZFNs), a substrate for meganucleases, a substrate for Cas9, and a substrate for another gene editing protein.

9. The isolated nucleic acid of claim 1, wherein the nucleic acid is contained within a vector.

10. A composition comprising a plurality of isolated nucleic acids as described in claim 1, optionally wherein the plurality of isolated nucleic acids are linked end-to-end.

11. An isolated host cell comprising the isolated nucleic acid of claim 1, optionally wherein the host cell further comprises a rolling circle replication protein that selectively binds to the RBE of the nucleic acid.

12. A method of delivering a heterologous nucleic acid to a cell, the method comprising delivering to the cell the isolated nucleic acid of claim 1.

13. A method of delivering a heterologous nucleic acid to a subject, the method comprising delivering to the subject the isolated nucleic acid claim 1, wherein the delivery of the nucleic acid does not result in an immune response against the isolated nucleic acid in the subject, wherein the immune response is a humoral response or a cellular response, and wherein the delivery is once or multiple times.

14. A method of delivering a heterologous nucleic acid to a subject, the method comprising delivering a host cell of claim 11 to the subject, wherein the host cell is delivered once or multiple times to the subject.

15. The isolated nucleic acid of claim 1, wherein the two opposing, lengthwise-symmetric stem-loops formed by interrupted palindromic sequences B-B' and C-C'.

16. The isolated nucleic acid of claim 1, wherein the one or more deletions in the truncated cross-arm sequence are between 11 and 20 nucleotides.

* * * * *